(12) United States Patent
DiNardo et al.

(10) Patent No.: US 11,642,134 B2
(45) Date of Patent: *May 9, 2023

(54) SURGICAL STAPLER WITH REVERSIBLE POLARITY

(71) Applicant: Cilag GmbH International, Zug (CH)

(72) Inventors: Brian F. DiNardo, Cincinnati, OH (US); Rodney V. Clingaman, Mason, OH (US); Charles J. Scheib, Loveland, OH (US); Frederick E. Shelton, IV, Hillsboro, OH (US); Richard F. Schwemberger, Cincinnati, OH (US); William R. Stager, Dayton, OH (US)

(73) Assignee: Cilag GmbH International, Zug (CH)

( * ) Notice: Subject to any disclaimer, the term of this patent is extended or adjusted under 35 U.S.C. 154(b) by 551 days.

This patent is subject to a terminal disclaimer.

(21) Appl. No.: 16/727,317

(22) Filed: Dec. 26, 2019

(65) Prior Publication Data
US 2020/0187948 A1    Jun. 18, 2020

Related U.S. Application Data

(63) Continuation of application No. 15/914,358, filed on Mar. 7, 2018, now Pat. No. 10,517,602, which is a (Continued)

(51) Int. Cl.
*A61B 17/115* (2006.01)
*A61B 17/11* (2006.01)
(Continued)

(52) U.S. Cl.
CPC ........ *A61B 17/1155* (2013.01); *A61B 17/068* (2013.01); *A61B 17/0644* (2013.01);
(Continued)

(58) Field of Classification Search
None
See application file for complete search history.

(56) References Cited

U.S. PATENT DOCUMENTS 5,205,459 A    4/1993   Brinkerhoff et al.
5,271,544 A    12/1993  Fox et al.
(Continued)

FOREIGN PATENT DOCUMENTS

CN    101502430 A    8/2009
CN    103908314 A    7/2014
(Continued)

OTHER PUBLICATIONS

European Search Report, Extended, and Written Opinion dated Oct. 7, 2016 for Application No. 16176142.4, 8 pages.
(Continued)

*Primary Examiner* — Shaun L David
(74) *Attorney, Agent, or Firm* — Frost Brown Todd LLP

(57) ABSTRACT

A method for resetting a stapling apparatus includes providing an apparatus with a cam member in a fired position. A circuit of the apparatus is then changed from a first polarity state to a second polarity state. A motor of the apparatus is then activated to rotate the cam member from a fired position back to a home position while the circuit is in the second polarity state.

20 Claims, 42 Drawing Sheets

Related U.S. Application Data continuation-in-part of application No. 14/751,231, filed on Jun. 26, 2015, now Pat. No. 10,456,134.

(51) Int. Cl.

| | | |
|---|---|---|
| *A61B 17/064* | (2006.01) | |
| *A61B 17/068* | (2006.01) | |
| *A61B 17/00* | (2006.01) | |
| *A61B 90/00* | (2016.01) | |
| *A61B 17/29* | (2006.01) | |

(52) U.S. Cl.
CPC .. *A61B 17/1114* (2013.01); *A61B 2017/00017* (2013.01); *A61B 2017/0042* (2013.01); *A61B 2017/00389* (2013.01); *A61B 2017/00393* (2013.01); *A61B 2017/00398* (2013.01); *A61B 2017/00734* (2013.01); *A61B 2017/2913* (2013.01); *A61B 2090/0811* (2016.02); *A61B 2090/0814* (2016.02)

(56) References Cited

U.S. PATENT DOCUMENTS

| | | | |
|---|---|---|---|
| 5,275,322 | A | 1/1994 | Wolf et al. |
| 5,285,945 | A | 2/1994 | Brinkerhoff et al. |
| 5,292,053 | A | 3/1994 | Smith et al. |
| 5,333,773 | A | 8/1994 | Main et al. |
| 5,350,104 | A | 9/1994 | Main et al. |
| 5,433,721 | A | 7/1995 | Hooven et al. |
| 5,533,661 | A | 7/1996 | Main et al. |
| 5,720,742 | A | 2/1998 | Zacharias |
| 6,120,462 | A | 9/2000 | Hibner et al. |
| 6,716,233 | B1 | 4/2004 | Whitman |
| 6,945,444 | B2 | 9/2005 | Gresham et al. |
| 7,794,475 | B2 | 9/2010 | Hess et al. |
| 8,028,885 | B2 | 10/2011 | Smith et al. |
| 8,408,439 | B2 | 4/2013 | Huang et al. |
| 8,453,914 | B2 | 6/2013 | Laurent et al. |
| 8,684,253 | B2 | 4/2014 | Giordano et al. |
| 8,910,847 | B2 | 12/2014 | Nalagatla et al. |
| 9,161,803 | B2 | 10/2015 | Yates et al. |
| 9,289,207 | B2 | 3/2016 | Shelton, IV |
| 9,463,022 | B2 | 10/2016 | Swayze et al. |
| 9,498,222 | B2 | 11/2016 | Schieb et al. |
| 9,532,783 | B2 | 1/2017 | Swayze et al. |
| 9,572,573 | B2 | 2/2017 | Scheib et al. |
| 9,597,081 | B2 | 3/2017 | Swayze et al. |
| 9,713,469 | B2 | 7/2017 | Leimbach et al. |
| 9,724,100 | B2 | 8/2017 | Scheib et al. |
| 9,907,552 | B2 | 3/2018 | Measamer et al. |
| 9,936,949 | B2 | 4/2018 | Measamer et al. |
| 10,456,134 | B2 | 10/2019 | DiNardo et al. |
| 10,517,602 | B2 | 12/2019 | DiNardo et al. |
| 10,888,318 | B2 | 1/2021 | Parihar |
| 2003/0066858 | A1 | 4/2003 | Holgersson |
| 2006/0278680 | A1 | 12/2006 | Viola et al. |
| 2007/0175953 | A1 | 8/2007 | Shelton, IV et al. |
| 2007/0270784 | A1* | 11/2007 | Smith ................ A61B 17/1155 606/1 |
| 2008/0185419 | A1 | 8/2008 | Smith et al. |
| 2010/0096431 | A1 | 4/2010 | Smith et al. |
| 2011/0290851 | A1 | 12/2011 | Shelton, IV |
| 2012/0055972 | A1 | 3/2012 | Marczyk |
| 2012/0223121 | A1 | 9/2012 | Viola et al. |
| 2013/0313304 | A1 | 11/2013 | Shelton, IV et al. |
| 2014/0158747 | A1 | 6/2014 | Measamer et al. |
| 2014/0166717 | A1 | 6/2014 | Swayze et al. |
| 2014/0246476 | A1 | 9/2014 | Hall et al. |
| 2015/0083772 | A1 | 3/2015 | Miller et al. |
| 2015/0083774 | A1* | 3/2015 | Measamer .......... A61B 17/068 227/175.1 |
| 2016/0374666 | A1 | 12/2016 | DiNardo et al. |
| 2016/0374672 | A1 | 12/2016 | Bear et al. |
| 2017/0258471 | A1 | 9/2017 | DiNardo et al. |
| 2017/0281173 | A1 | 10/2017 | Shelton, IV et al. |
| 2018/0168635 | A1 | 6/2018 | Shelton, IV et al. |
| 2019/0125455 | A1 | 5/2019 | Shelton, IV et al. |
| 2021/0068838 | A1 | 3/2021 | DiNardo et al. |
| 2021/0290238 | A1 | 9/2021 | DiNardo et al. |

FOREIGN PATENT DOCUMENTS

| | | |
|---|---|---|
| EP | 2742874 A2 | 6/2014 |
| EP | 2777539 A2 | 9/2014 |
| EP | 2792308 A2 | 10/2014 |
| JP | S62-77805 A | 4/1987 |
| JP | H02-107358 U | 8/1990 |
| JP | H04-224709 A | 8/1992 |
| JP | 2000-139617 A | 5/2000 |
| JP | 2006-119162 A | 5/2006 |
| JP | 2006-122297 A | 5/2006 |
| JP | 2008-279260 A | 11/2008 |
| JP | 2009-539420 A | 11/2009 |
| JP | 2011-067258 A | 4/2011 |
| JP | 2014-012130 A | 1/2014 |
| JP | 2016-124333 A | 7/2016 |
| JP | 2017-530841 A | 10/2017 |
| WO | WO 2015/026562 A1 | 2/2015 |
| WO | WO 2015/104676 A1 | 7/2015 |

OTHER PUBLICATIONS

European Examination Report dated Jul. 3, 2018 for Application No. 16176142.4, 6 pages.
Extended European Search Report dated Nov. 20, 2019 for Application No. 19162090.6, 7 pages.
Extended European Search Report dated Feb. 12, 2020 for Application No. 19210043.6, 10 pages.
International Search Report and Written Opinion dated Aug. 26, 2016 for International Application No. PCT/US2016/038870, 17 pages.
Japanese Notification of Reasons for Refusal dated Aug. 13, 2020 for Application No. 2017-567148, 4 pages.
U.S. Appl. No. 16/994,096, entitled "Surgical Stapler with Reversible Polarity," filed Aug. 14, 2020.
Chinese Office Action and Search Report dated Mar. 28, 2020, for Application No. 201680037782.3, 4 pages.
Indian Office Action dated Jul. 6, 2022, for Application No. 201914007029, 7 pages.
Japanese Notification of Reasons for Refusal dated Feb. 9, 2021, for Application No. 2017-043475, 5 pages.
Japanese Notification of Reasons for Refusal dated Mar. 23, 2021, for Application No. 2017-146858, 4 pages.
Japanese Notification of Reasons for Refusal dated Mar. 26, 2021, for Application No. 2017-567148, 2 pages.
U.S. Appl. No. 16/994,096.
U.S. Appl. No. 17/221,356.
Japanese Office Action and Search Report by Registered Search Organization, dated Jan. 31, 2023 for Application No. JP 2019-040277, 31 pgs.

* cited by examiner

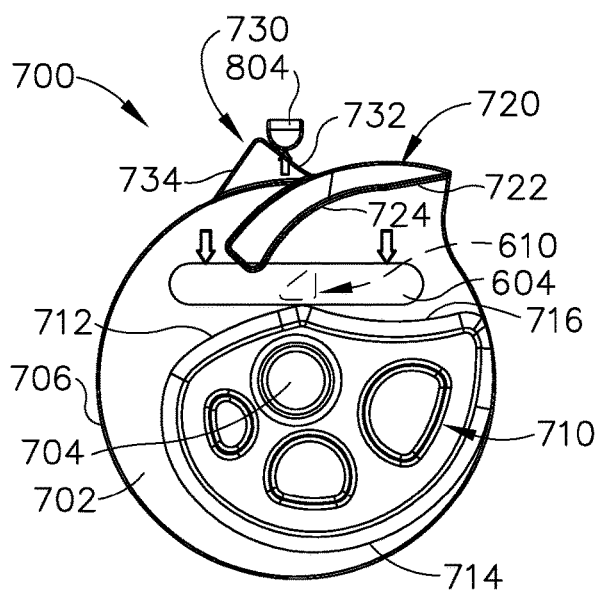
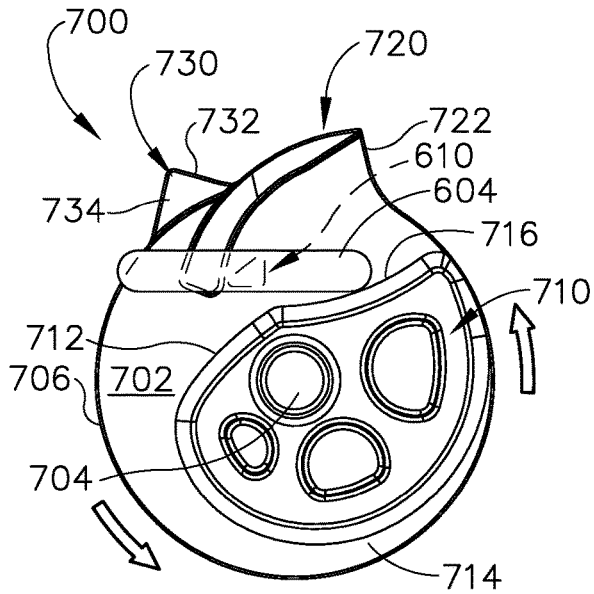
Fig.25A
Fig.25B
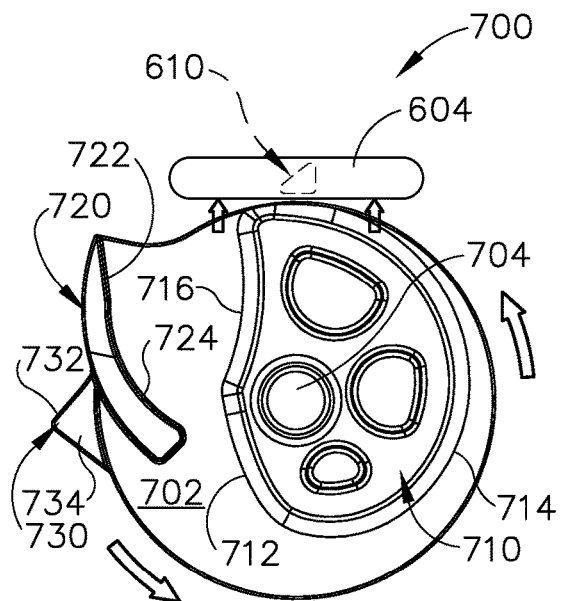
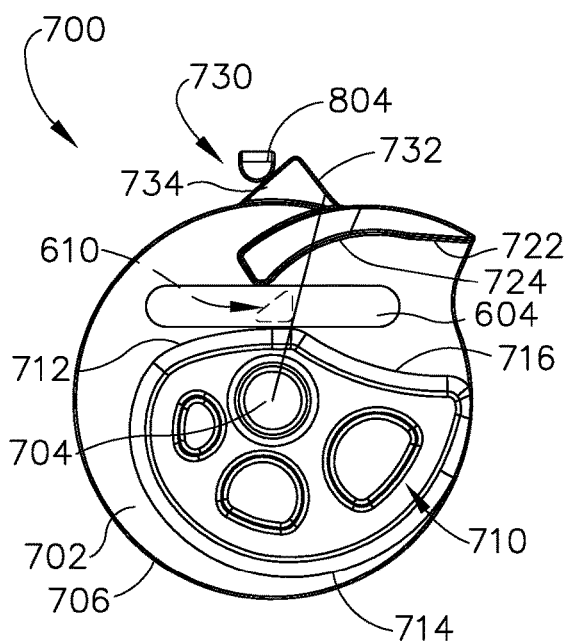
Fig.25C
Fig.25D

SURGICAL STAPLER WITH REVERSIBLE POLARITY

PRIORITY

This application is a continuation of U.S. patent application Ser. No. 15/914,358, entitled "Surgical Stapler with Reversible Polarity," filed Mar. 7, 2018, and issued as U.S. Pat. No. 10,517,602 on Dec. 31, 2019, which is a continuation-in-part of U.S. patent application Ser. No. 14/751,231, entitled "Surgical Stapler with Reversible Motor," filed Jun. 26, 2015, and issued as U.S. Pat. No. 10,456,134 on Oct. 29, 2019, the disclosure of which is incorporated by reference herein.

BACKGROUND

In some surgical procedures (e.g., colorectal, bariatric, thoracic, etc.), portions of a patient's digestive tract (e.g., the gastrointestinal tract and/or esophagus, etc.) may be cut and removed to eliminate undesirable tissue or for other reasons. Once the tissue is removed, the remaining portions of the digestive tract may be coupled together in an end-to-end anastomosis. The end-to-end anastomosis may provide a substantially unobstructed flow path from one portion of the digestive tract to the other portion of the digestive tract, without also providing any kind of leaking at the site of the anastomosis.

One example of an instrument that may be used to provide an end-to-end anastomosis is a circular stapler. Some such staplers are operable to clamp down on layers of tissue, cut through the clamped layers of tissue, and drive staples through the clamped layers of tissue to substantially seal the layers of tissue together near the severed ends of the tissue layers, thereby joining the two severed ends of the anatomical lumen together. The circular stapler may be configured to sever the tissue and seal the tissue substantially simultaneously. For instance, the circular stapler may sever excess tissue that is interior to an annular array of staples at an anastomosis, to provide a substantially smooth transition between the anatomical lumen sections that are joined at the anastomosis. Circular staplers may be used in open procedures or in endoscopic procedures. In some instances, a portion of the circular stapler is inserted through a patient's naturally occurring orifice.

Examples of circular staplers are described in U.S. Pat. No. 5,205,459, entitled "Surgical Anastomosis Stapling Instrument," issued Apr. 27, 1993; U.S. Pat. No. 5,271,544, entitled "Surgical Anastomosis Stapling Instrument," issued Dec. 21, 1993; U.S. Pat. No. 5,275,322, entitled "Surgical Anastomosis Stapling Instrument," issued Jan. 4, 1994; U.S. Pat. No. 5,285,945, entitled "Surgical Anastomosis Stapling Instrument," issued Feb. 15, 1994; U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996; and U.S. Pat. No. 8,910,847, entitled "Low Cost Anvil Assembly for a Circular Stapler," issued Dec. 16, 2014. The disclosure of each of the above-cited U.S. Patents is incorporated by reference herein.

Some circular staplers may include a motorized actuation mechanism. Examples of circular staplers with motorized actuation mechanisms are described in U.S. Pub. No. 2015/0083772, entitled "Surgical Stapler with Rotary Cam Drive and Return," published Mar. 26, 2015, now abandoned; U.S. Pub. No. 2015/0083773, entitled "Surgical Stapling Instrument with Drive Assembly Having Toggle Features," published Mar. 26, 2015, issued as U.S. Pat. No. 9,936,949 on Apr. 10, 2018; U.S. Pat. No. 9,907,552, entitled "Control Features for Motorized Surgical Stapling Instrument," issued Mar. 6, 2018; and U.S. Pat. No. 9,713,469, entitled "Surgical Stapler with Rotary Cam Drive," issued Jul. 25, 2017. The disclosure of each of the above-cited U.S. Patents and Patent Publications is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 25A depicts a schematic end view of the rotary cam of FIG. 16, the cam follower of FIG. 14, and the rocker member of FIG. 19A, with the rotary cam in the fourth angular position, the cam follower in the first pivotal position, and the rocker member in the second pivotal position;

FIG. 25B depicts a schematic end view of the rotary cam of FIG. 16 and the cam follower of FIG. 14, with the rotary cam in the third angular position, the cam follower transitioning toward the second pivotal position, and the rocker member of FIG. 19A in the first pivotal position;

FIG. 25C depicts a schematic end view of the rotary cam of FIG. 16 and the cam follower of FIG. 14, with the rotary cam in the second angular position, the cam follower in the second pivotal position, and the rocker member of FIG. 19A in the first pivotal position;

FIG. 25D depicts a schematic end view of the rotary cam of FIG. 16, the cam follower of FIG. 14, and the rocker member of FIG. 19A, with the rotary cam in the first angular position, the cam follower in the first pivotal position, and the rocker member in a second pivotal position;

Figure 1:
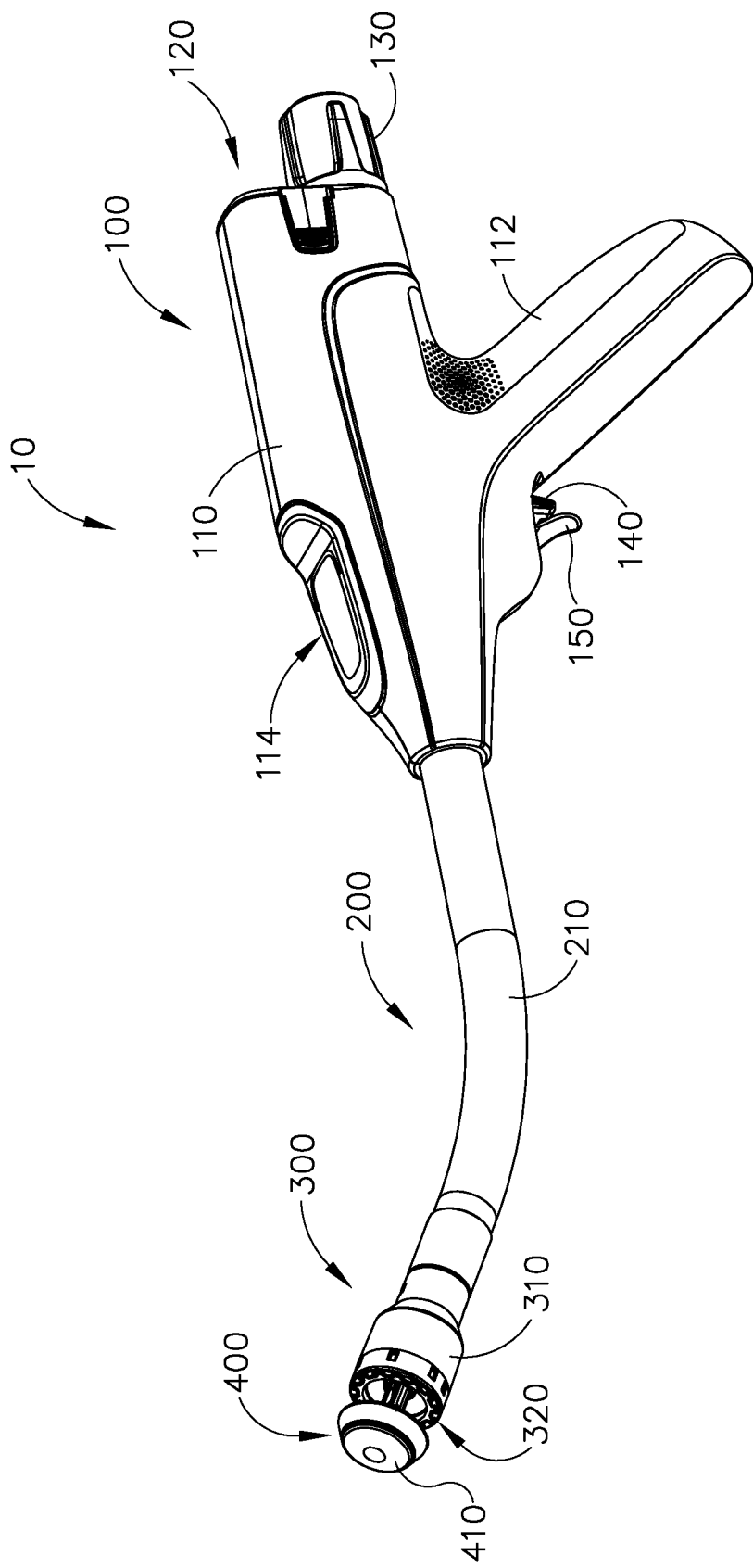
FIG. 1 depicts a perspective view of an exemplary circular stapler.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Circular Stapling Surgical Instrument

Figure 2:
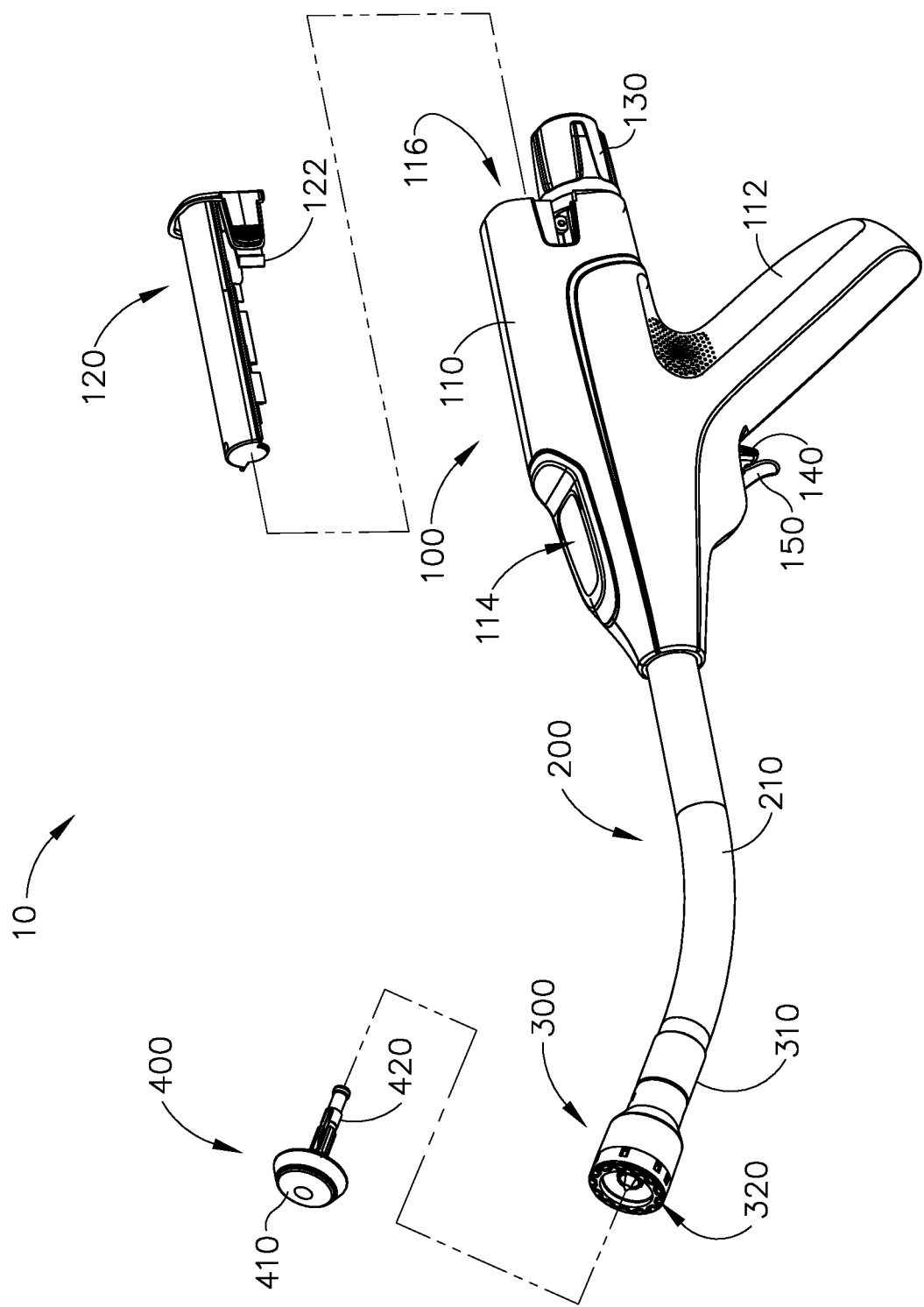
FIG. 2 depicts a perspective view of the circular stapler of FIG. 1, with a battery pack removed from a handle assembly and an anvil removed from a stapling head assembly.

FIGS. 1-2 depict an exemplary surgical circular stapling instrument (10) that may be used to provide an end-to-end anastomosis between two sections of an anatomical lumen such as a portion of a patient's digestive tract. Instrument (10) of this example comprises a handle assembly (100), a shaft assembly (200), a stapling head assembly (300), and an anvil (400). Handle assembly (100) comprises a casing (110) defining an obliquely oriented pistol grip (112). In some versions, pistol grip (112) is perpendicularly oriented. In some other versions, pistol grip (112) is omitted. Handle assembly (110) further includes a window (114) that permits viewing of a movable indicator needle (526) as will be described in greater detail below. In some versions, a series of hash marks, colored regions, and/or other fixed indicators are positioned adjacent to window (114) in order to provide a visual context for indicator needle (526), thereby facilitating operator evaluation of the position of needle (526) within window (114). Various suitable alternative features and configurations for handle assembly (112) will be apparent to those of ordinary skill in the art in view of the teachings herein.

Instrument (10) of the present example further includes a battery pack (120). Battery pack (120) is operable to provide electrical power to a motor (160) in pistol grip (112) as will be described in greater detail below. Battery pack (120) is removable from handle assembly (100). In particular, as shown in FIGS. 1-2, battery pack (120) may be inserted into a socket (116) defined by casing (110). Once battery pack (120) is fully inserted in socket (116), latches (122) of battery pack (120) may resiliently engage interior features of casing (110) to provide a snap fit. To remove battery pack (120), the operator may press latches (122) inwardly to disengage latches (122) from the interior features of casing (110) then pull battery pack (120) proximally from socket (116). It should be understood that battery pack (120) and handle assembly (100) may have complementary electrical contacts, pins and sockets, and/or other features that provide paths for electrical communication from battery pack (120) to electrically powered components in handle assembly (100) when battery pack (120) is inserted in socket (116). It should also be understood that, in some versions, battery pack (120) is unitarily incorporated within handle assembly (100) such that battery back (120) cannot be removed from handle assembly (100).

Shaft assembly (200) extends distally from handle assembly (100) and includes a preformed bend. In some versions, the preformed bend is configured to facilitate positioning of stapling head assembly (300) within a patient's colon. Various suitable bend angles or radii that may be used will be apparent to those of ordinary skill in the art in view of the teachings herein. In some other versions, shaft assembly (200) is straight, such that shaft assembly (200) lacks a preformed bend. Various exemplary components that may be incorporated into shaft assembly (100) will be described in greater detail below.

Stapling head assembly (300) is located at the distal end of shaft assembly (200). As shown in FIGS. 1-2 and as will be described in greater detail below, anvil (400) is configured to removably couple with shaft assembly (200), adjacent to stapling head assembly (300). As will also be described in greater detail below, anvil (400) and stapling head assembly (300) are configured to cooperate to manipulate tissue in three ways, including clamping the tissue, cutting the tissue, and stapling the tissue. A knob (130) at the proximal end of handle assembly (100) is rotatable relative to casing (110) to provide precise clamping of the tissue between anvil (400) and stapling head assembly (300). When a safety trigger (140) of handle assembly (100) is pivoted away from a firing trigger (150) of handle assembly (100), firing trigger (150) may be actuated to thereby provide cutting and stapling of the tissue.

A. Exemplary Anvil

In the following discussion of anvil (400), the terms "distal" and "proximal" (and variations thereof) will be used with reference to the orientation of anvil (400) when anvil (400) is coupled with shaft assembly (200) of instrument (10). Thus, proximal features of anvil (400) will be closer to the operator of instrument (10); while distal features of anvil (400) will be further from the operator of instrument (10).

Figure 3:
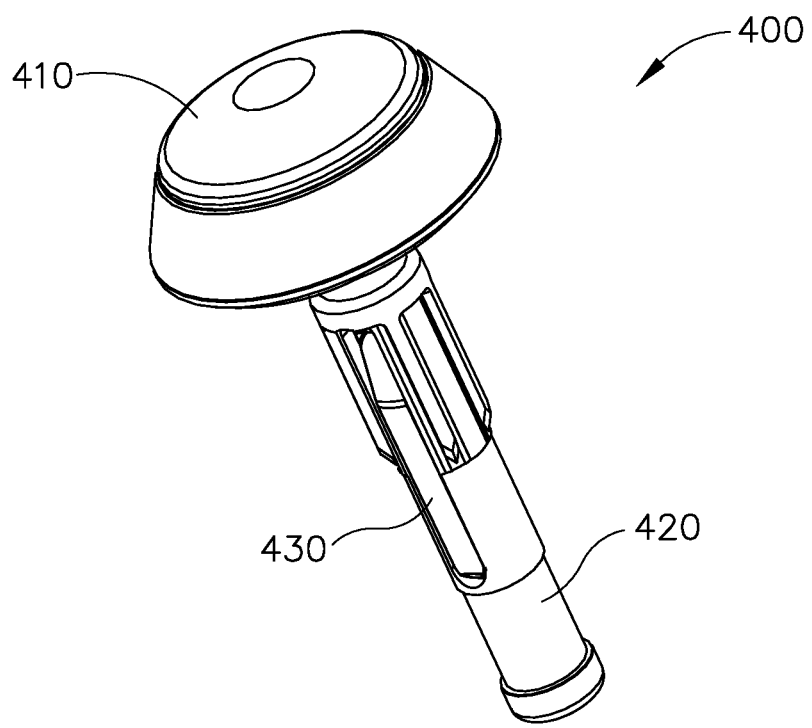
FIG. 3 depicts a perspective view of the anvil of the circular stapler of FIG. 1.
Figure 4:
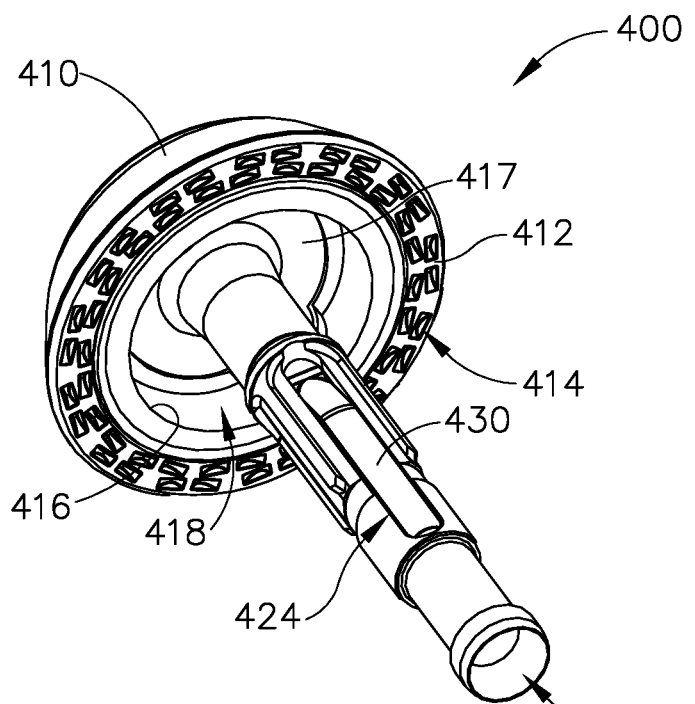
FIG. 4 depicts another perspective view of the anvil of FIG. 3.
Figure 5:
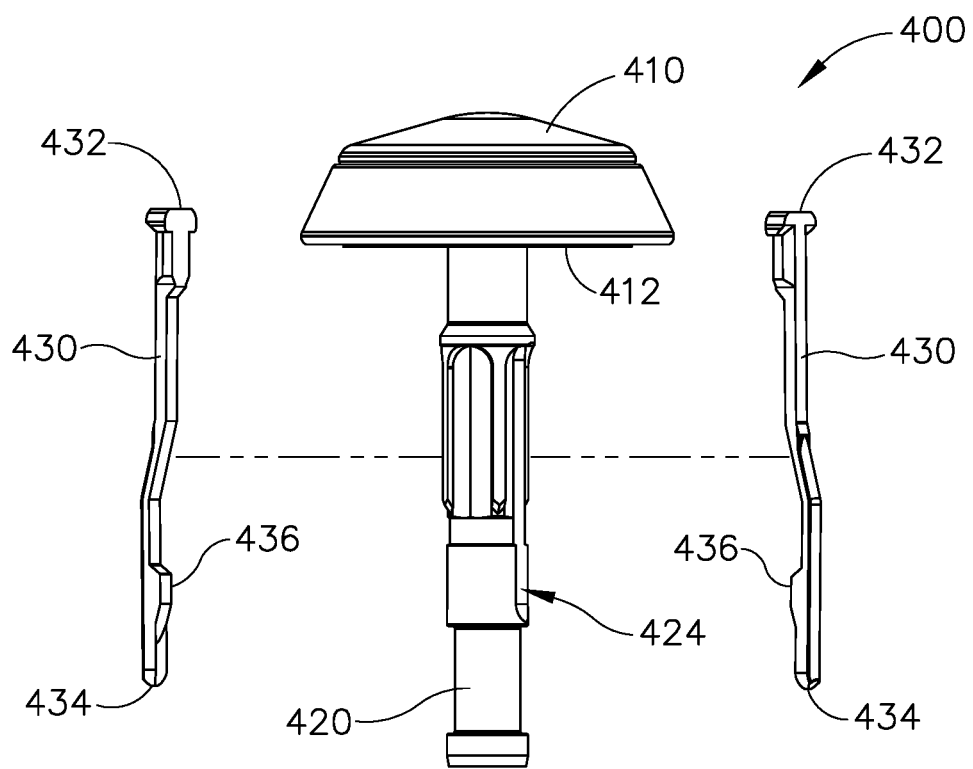
FIG. 5 depicts an exploded side elevational view of the anvil of FIG. 3.

As best seen in FIGS. 3-5, anvil (400) of the present example comprises a head (410) and a shank (420). Head (410) includes a proximal surface (412) that defines a plurality of staple forming pockets (414). Staple forming pockets (414) are arranged in two concentric annular arrays. In some other versions, staple forming pockets (414) are arranged in three or more concentric annular arrays. Staple forming pockets (414) are configured to deform staples as the staples are driven into staple forming pockets (414). For instance, each staple forming pocket (414) may deform a generally "U" shaped staple into a "B" shape as is known in the art. As best seen in FIG. 4, proximal surface (412) terminates at an inner edge (416), which defines an outer boundary of an annular recess (418) surrounding shank (420).

Shank (420) defines a bore (422) and includes a pair of pivoting latch members (430) positioned in bore (422). As best seen in FIG. 5, each latch member (430) includes a "T" shaped distal end (432), a rounded proximal end (434), and a latch shelf (436) located distal to proximal end (434). "T" shaped distal ends (432) secure latch members (430) within bore (422). Latch members (430) are positioned within bore (422) such that distal ends (434) are positioned at the proximal ends of lateral openings (424), which are formed through the sidewall of shank (420). Lateral openings (424) thus provide clearance for distal ends (434) and latch shelves (436) to deflect radially outwardly from the longitudinal axis defined by shank (420). However, latch members (430) are configured to resiliently bias distal ends (434) and latch shelves (436) to radially inwardly toward the longitudinal axis defined by shank (420). Latch members (430) thus act as retaining clips. This allows anvil (400) to be removably secured to a trocar (330) of stapling head assembly (300) as will be described in greater detail below. It should be understood, however, that latch members (436) are merely optional. Anvil (400) may be removably secured to a trocar (330) using any other suitable components, features, or techniques.

In addition to or in lieu of the foregoing, anvil (400) may be further constructed and operable in accordance with at least some of the teachings of U.S. Pat. Nos. 5,205,459; 5,271,544; 5,275,322; 5,285,945; 5,292,053; 5,333,773; 5,350,104; 5,533,661; and/or 8,910,847, the disclosures of which are incorporated by reference herein. Still other suitable configurations will be apparent to one of ordinary skill in the art in view of the teachings herein.

B. Exemplary Stapling Head Assembly

Figure 6:
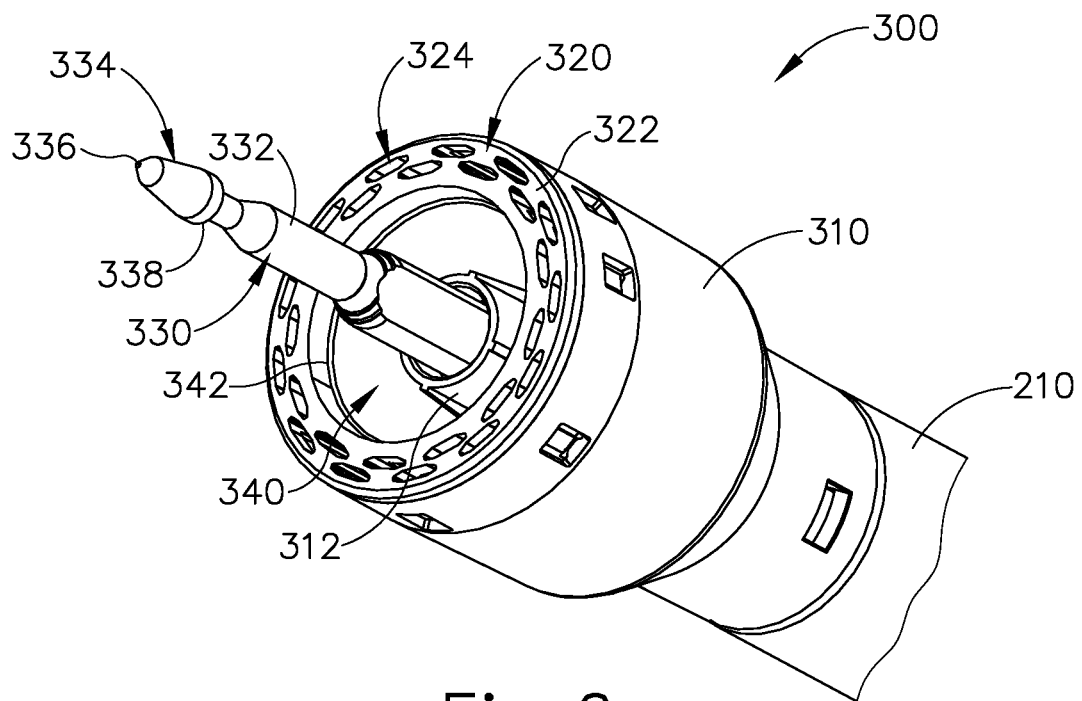
FIG. 6 depicts a perspective view of the stapling head assembly of the circular stapler of FIG. 1.
Figure 7:
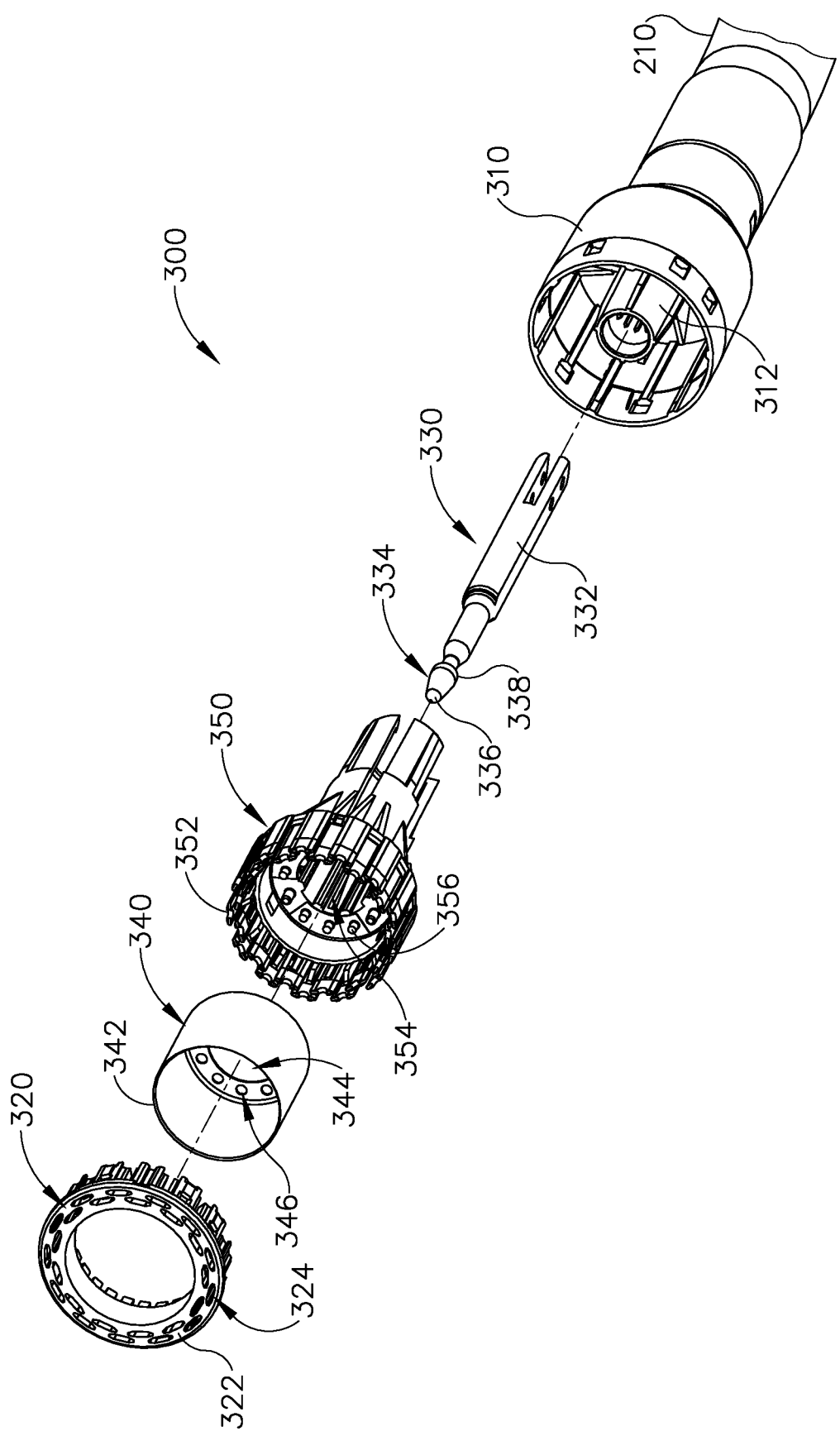
FIG. 7 depicts an exploded perspective view of the stapling head assembly of FIG. 6.

As best seen in FIGS. 6-7, stapling head assembly (300) of the present example is coupled to a distal end of shaft assembly (200) and comprises a tubular casing (310) housing a slidable staple driver member (350). A cylindraceous inner core member (312) extends distally within tubular casing (310). Tubular casing (310) is fixedly secured to an outer sheath (210) of shaft assembly (200), such that tubular casing (310) serves as a mechanical ground for stapling head assembly (300).

Trocar (330) is positioned coaxially within inner core member (312) of tubular casing (310). As will be described in greater detail below, trocar (330) is operable to translate distally and proximally relative to tubular casing (310) in response to rotation of knob (130) relative to casing (110) of handle assembly (100). Trocar (330) comprises a shaft (332) and a head (334). Head (334) includes a pointed tip (336) and an inwardly extending proximal surface (338). Shaft (332) thus provides a reduced outer diameter just proximal to head (334), with surface (338) providing a transition between that reduced outer diameter of shaft (332) and the outer diameter of head (334). While tip (336) is pointed in the present example, tip (336) is not sharp. Tip (336) will thus not easily cause trauma to tissue due to inadvertent contact with tissue. Head (334) and the distal portion of shaft (332) are configured for insertion in bore (422) of anvil (400). Proximal surface (338) and latch shelves (436) have complementary positions and configurations such that latch shelves (436) engage proximal surface (338) when shank (420) of anvil (400) is fully seated on trocar (330). Anvil (400) is thus secured to trocar (330) through a snap fit due to latch members (430).

Staple driver member (350) is operable to actuate longitudinally within tubular casing (310) in response to activation of motor (160) as will be described in greater detail below. Staple driver member (350) includes two distally presented concentric annular arrays of staple drivers (352). Staple drivers (352) are arranged to correspond with the arrangement of staple forming pockets (414) described above. Thus, each staple driver (352) is configured to drive a corresponding staple into a corresponding staple forming pocket (414) when stapling head assembly (300) is actuated. It should be understood that the arrangement of staple drivers (352) may be modified just like the arrangement of staple forming pockets (414) as described above. Staple driver member (350) also defines a bore (354) that is configured to coaxially receive core member (312) of tubular casing (310). An annular array of studs (356) project distally from a distally presented surface surrounding bore (354).

A cylindraceous knife member (340) is coaxially positioned within staple driver member (350). Knife member (340) includes a distally presented, sharp circular cutting edge (342). Knife member (340) is sized such that knife member (340) defines an outer diameter that is smaller than the diameter defined by the inner annular array of staple drivers (352). Knife member (340) also defines an opening that is configured to coaxially receive core member (312) of tubular casing (310). An annular array of openings (346) formed in knife member (340) is configured to complement the annular array of studs (356) of staple driver member (350), such that knife member (340) is fixedly secured to staple driver member (350) via studs (356) and openings (346). Other suitable structural relationships between knife member (340) and stapler driver member (350) will be apparent to those of ordinary skill in the art in view of the teachings herein.

A deck member (320) is fixedly secured to tubular casing (310). Deck member (320) includes a distally presented deck surface (322) defining two concentric annular arrays of staple openings (324). Staple openings (324) are arranged to correspond with the arrangement of staple drivers (352) and staple forming pockets (414) described above. Thus, each staple opening (324) is configured to provide a path for a corresponding staple driver (352) to drive a corresponding staple through deck member (320) and into a corresponding staple forming pocket (414) when stapling head assembly (300) is actuated. It should be understood that the arrangement of staple openings (322) may be modified just like the arrangement of staple forming pockets (414) as described above. It should also be understood that various structures and techniques may be used to contain staples within stapling head assembly (300) before stapling head assembly (300) is actuated. Such structures and techniques that are used to contain staples within stapling head assembly (300) may prevent the staples from inadvertently falling out through staple openings (324) before stapling head assembly (300) is actuated. Various suitable forms that such structures and techniques may take will be apparent to those of ordinary skill in the art in view of the teachings herein.

As best seen in FIG. 6, deck member (320) defines an inner diameter that is just slightly larger than the outer diameter defined by knife member (340). Deck member (320) is thus configured to allow knife member (340) to translate distally to a point where cutting edge (342) is distal to deck surface (322).

In addition to or in lieu of the foregoing, stapling head assembly (300) may be further constructed and operable in accordance with at least some of the teachings of U.S. Pat. Nos. 5,205,459; 5,271,544; 5,275,322; 5,285,945; 5,292,053; 5,333,773; 5,350,104; 5,533,661; and/or 8,910,847, the disclosures of which are incorporated by reference herein. Still other suitable configurations will be apparent to one of ordinary skill in the art in view of the teachings herein.

C. Exemplary Shaft Assembly

Figure 8:
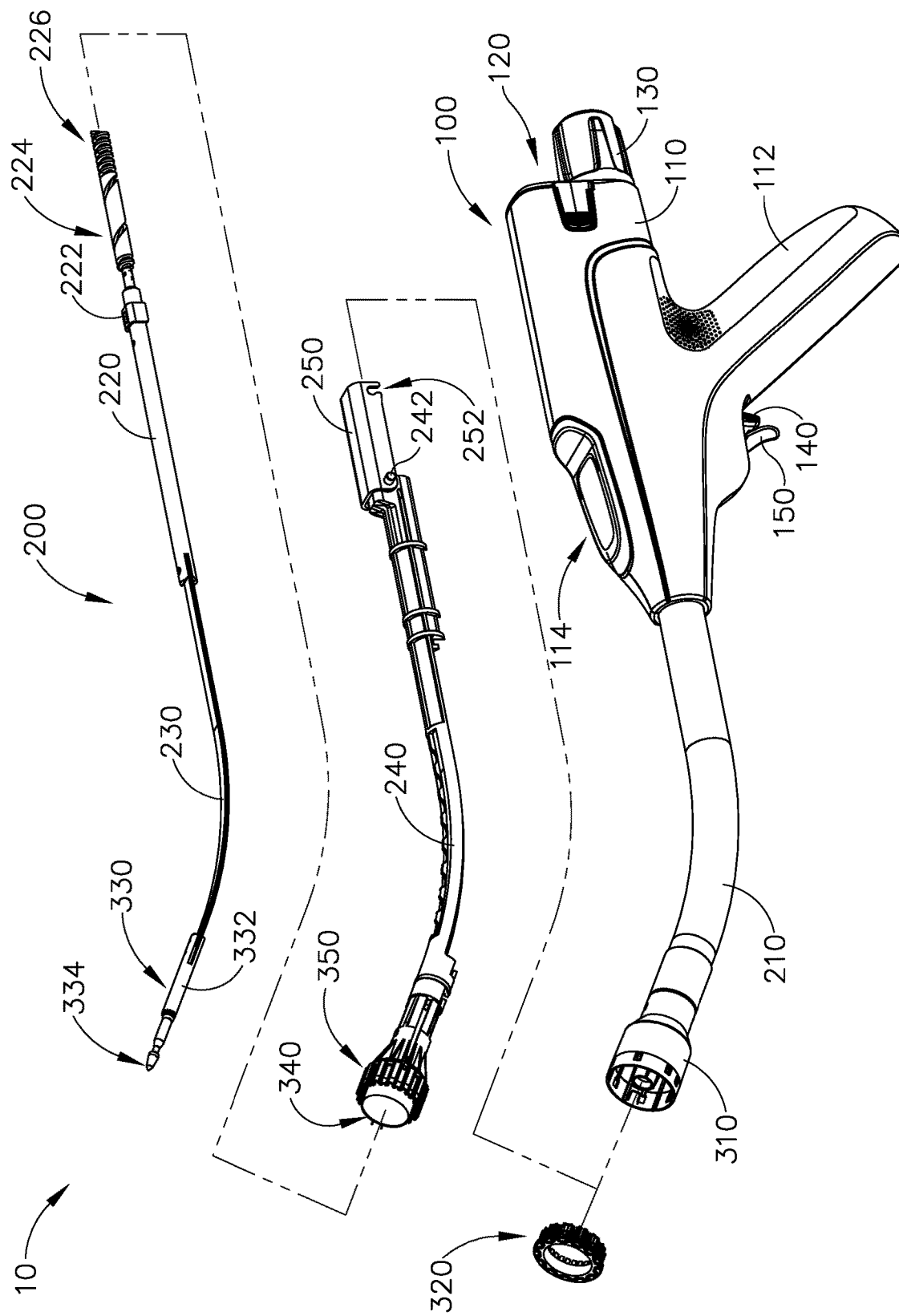
FIG. 8 depicts an exploded perspective view of the circular stapler of FIG. 1, with portions of the shaft assembly shown separately from each other.

FIG. 8 shows various components of shaft assembly (200), which couples components of stapling head assembly (300) with components of handle assembly (100). In particular, and as noted above, shaft assembly (200) includes an outer sheath (210) that extends between handle assembly (100) and tubular casing (310). In the present example, outer sheath (210) is rigid and includes a preformed curved section as noted above.

Shaft assembly (200) further includes a trocar actuation rod (220) and a trocar actuation band assembly (230). The distal end of trocar actuation band assembly (230) is fixedly secured to the proximal end of trocar shaft (332). The proximal end of trocar actuation band assembly (230) is fixedly secured to the distal end of trocar actuation rod (220). It should therefore be understood that trocar (330) will translate longitudinally relative to outer sheath (210) in response to translation of trocar actuation band assembly (230) and trocar actuation rod (220) relative to outer sheath (210). Trocar actuation band assembly (230) is configured to flex such that trocar actuation band assembly (230) may follow along the preformed curve in shaft assembly (200) as trocar actuation band assembly (230) is translated longitudinally relative to outer sheath (210). However, trocar actuation band assembly (230) has sufficient column strength and tensile strength to transfer distal and proximal forces from trocar actuation rod (220) to trocar shaft (332). Trocar actuation rod (220) is rigid. A clip (222) is fixedly secured to trocar actuation rod (220) and is configured to cooperate with complementary features within handle assembly (100) to prevent trocar actuation rod (220) from rotating within handle assembly (100) while still permitting trocar actuation rod (220) to translate longitudinally within handle assembly (100). Trocar actuation rod (220) further includes a coarse helical threading (224) and a fine helical threading (226). Details regarding the movement of trocar actuation rod (220) will be described in greater detail below.

Shaft assembly (200) further includes a stapling head assembly driver (240) that is slidably received within outer sheath (210). The distal end of stapling head assembly driver (240) is fixedly secured to the proximal end of staple driver member (350). The proximal end of stapling head assembly driver (240) is secured to a drive bracket (250) via a pin (242). It should therefore be understood that staple driver member (350) will translate longitudinally relative to outer sheath (210) in response to translation of stapling head assembly driver (240) and drive bracket (250) relative to outer sheath (210). Stapling head assembly driver (240) is configured to flex such that stapling head assembly driver (240) may follow along the preformed curve in shaft assembly (200) as stapling head assembly driver (240) is translated longitudinally relative to outer sheath (210). However, stapling head assembly driver (240) has sufficient column strength to transfer distal forces from drive bracket (250) to staple driver member (350). Details regarding the movement of drive bracket (250) will be described in greater detail below.

While not shown in FIG. 8, it should be understood that shaft assembly (200) may further include one or more spacer elements within outer sheath (210). Such spacer elements may be configured to support trocar actuation band assembly (230) and/or stapling head assembly driver (240) as trocar actuation band assembly (230) and/or stapling head assembly driver (240) translate through outer sheath (210). For instance, such spacer elements may prevent trocar actuation band assembly (230) and/or stapling head assembly driver (240) from buckling as trocar actuation band assembly (230) and/or stapling head assembly driver (240) translate through outer sheath (210). Various suitable forms that such spacer elements may take will be apparent to those of ordinary skill in the art in view of the teachings herein.

In addition to or in lieu of the foregoing, shaft assembly (200) may be further constructed and operable in accordance with at least some of the teachings of U.S. Pat. Nos. 5,205,459; 5,271,544; 5,275,322; 5,285,945; 5,292,053; 5,333,773; 5,350,104; 5,533,661; and/or 8,910,847, the disclosures of which are incorporated by reference herein. Still other suitable configurations will be apparent to one of ordinary skill in the art in view of the teachings herein.

D. Exemplary Actuator Handle Assembly

Figure 9:
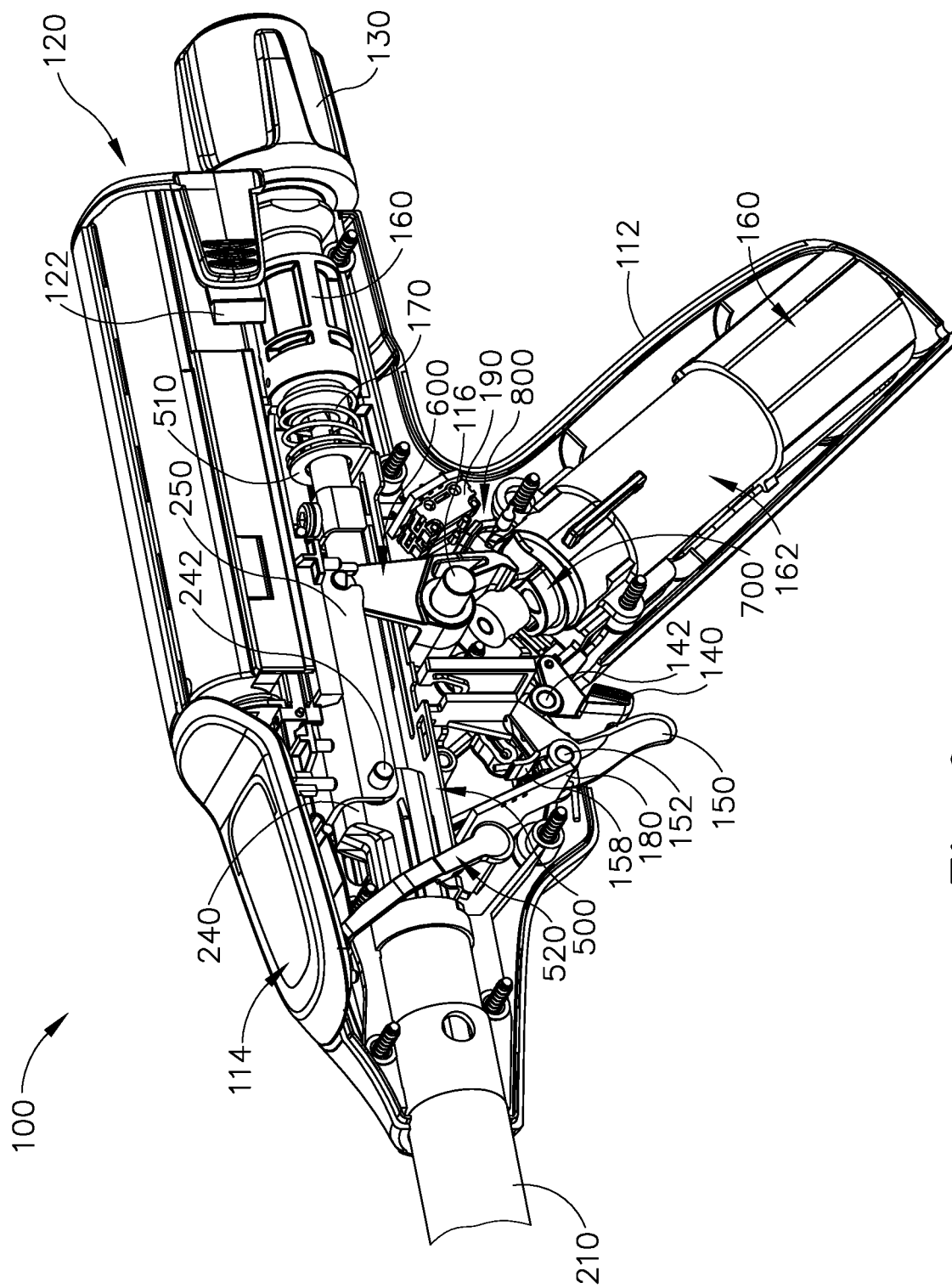
FIG. 9 depicts a perspective view of the handle assembly of the circular stapler of FIG. 1, with a housing half omitted to reveal internal components of the handle assembly.

As shown in FIG. 9, handle assembly (100) includes several components that are operable to actuate anvil (400) and stapling head assembly (300). Handle assembly (100) also includes components that are operable to selectively lock out triggers (140, 150) based on the position of anvil (400) relative to stapling head assembly (300). When triggers (140, 150) are locked out, firing trigger (150) is prevented from initiating actuation of stapling head assembly (300). Thus, trigger (150) is only operable to initiate actuation of stapling head assembly (300) when the position of anvil (400) relative to stapling head assembly (300) is within a predefined range. The components of handle assembly (100) that provide the foregoing operability will be described in greater detail below.

1. Exemplary Anvil Actuation Assembly

Knob (130) protrudes proximally from casing (110) of handle assembly and is rotatable relative to casing (110). As shown in FIG. 9, a nut (160) is secured to the distal end of knob (130). In the present example, nut (160) is fixedly secured to the distal end of knob (130) such that nut (160) will rotate unitarily with knob (130). Nut (160) and knob (130) are configured to cooperate with trocar actuation rod (220) to thereby translate trocar actuation rod (220) longitudinally relative to casing (110) in response to rotation of nut (160) and knob (130) relative to casing (110). As noted above, trocar (330) will translate longitudinally relative to outer sheath (210) in response to translation of trocar actuation rod (220) relative to outer sheath (210) and casing (110).

The proximal portion of trocar actuation rod (220) is positioned within handle assembly (100) to engage nut (160) and knob (130). In particular, trocar actuation rod (220) is positioned within handle assembly (100) such that coarse helical threading (224) will selectively engage a thread engagement feature (not shown) within the interior of nut (160); and such that fine helical threading (226) will selectively engage a thread engagement feature (not shown) within the interior of knob (130). In some versions, the thread engagement feature of nut (160) comprises an inwardly directed tab; while the thread engagement feature of knob (130) comprises a helical threading. Other suitable forms that such thread engagement features may take will be apparent to those of ordinary skill in the art in view of the teachings herein.

In the present example, when nut (160) and knob (130) are rotated relative to casing (110), trocar actuation rod (220)

travels proximally through a first range of longitudinal motion where coarse helical threading (224) is engaged with nut (160) to provide a relatively rapid rate of translation. Fine helical threading (226) is not engaged with knob (130) during this range of motion. When nut (160) and knob (130) are further rotated relative to casing (110) after trocar actuation rod (220) completes the first range of motion, trocar actuation rod (220) will continue to travel proximally through a second range of longitudinal motion where fine helical threading (226) is engaged with knob (130) to provide a relatively slow rate of translation. Thus, trocar actuation rod (220) will translate proximally through a sequence of rapid translation followed by slow translation, based on engagement between coarse helical threading (224) and nut (160) followed by engagement between fine helical threading (226) and knob (130).

It should be understood that when anvil (400) is coupled with trocar (330), rotation of knob (130) will provide corresponding translation of anvil relative to stapling head assembly (300). It should also be understood that knob (130) may be rotated in a first angular direction (e.g., clockwise) to retract anvil (400) toward stapling head assembly (300); and in a second angular direction (e.g., counterclockwise) to advance anvil (500) away from stapling head assembly (300). Knob (130) may thus be used to adjust the gap distance (d) between opposing surfaces (412, 322) of anvil (400) and stapling head assembly (300) until a suitable gap distance (d) has been achieved as shown in FIG. 21C and as described in greater detail below.

2. Exemplary Trigger Lockout Assembly

As noted above, knob may be used to adjust the gap distance (d) between opposing surfaces (412, 322) of anvil (400) and stapling head assembly (300). Setting an appropriate gap distance (d) before actuating stapling head assembly (300) may be critical to the success of an anastomosis. For instance, if the gap distance (d) is too great, the staples that are deployed at the anastomosis site may not be sufficiently formed by staple forming pockets (414). This may result in leakage at the anastomosis site, and in some cases may ultimately lead to the separation of the anatomical lumen sections that are joined at the anastomosis site. If the gap distance (d) is too small, the internal structure of the tissue compressed between surfaces (412, 322) may be damaged to the point where the structural integrity of the tissue is compromised. This may prevent the tissue from adequately holding the formed staples, which again may result in leakage or other failure of the anastomosis. It may therefore be desirable to provide the operator with some form of feedback indicating whether the gap distance (d) is within an appropriate range. It may also be desirable to prevent the operator from actuating stapling head assembly (300) unless the gap distance (d) is within an appropriate range.

Figure 10:
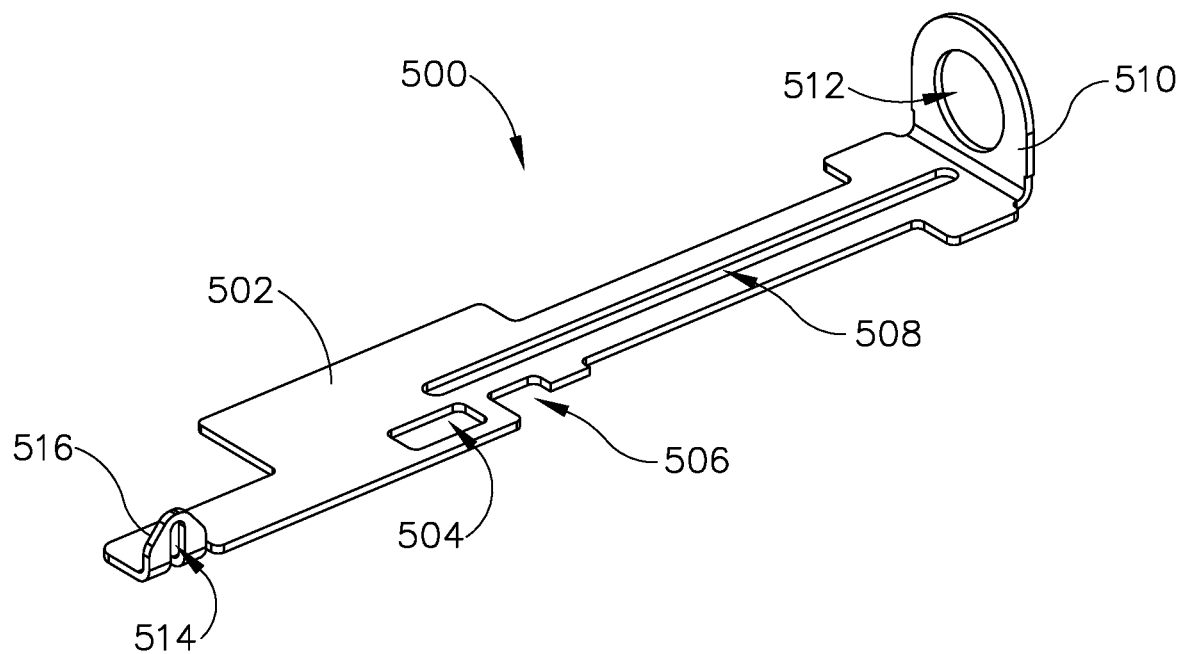
FIG. 10 depicts a perspective view of a bracket of the handle assembly of FIG. 9.

FIGS. 9-12E show components that provide feedback to the operator to indicate whether the gap distance (d) is within an appropriate range; and prevent the operator from actuating stapling head assembly (300) unless the gap distance (d) is within an appropriate range. As best seen in FIGS. 12B-12C, a bracket (500) is configured and positioned to move in response to movement of trocar actuation rod (220). As best seen in FIG. 10, bracket (500) includes a rigid body (502) that defines a first slot (504), a second slot (506), and a third slot (508). An upright feature (510) is positioned at the proximal end of body (502) and defines an opening (512). Trocar actuation rod (220) extends coaxially through opening (512). As shown in FIG. 9, a coil spring (170) is interposed between the proximal end of upright feature (510) and a rigid bulkhead feature that is defined by casing (110) and that forms a support journal for nut (160). The bulkhead is fixed within casing (110) and thereby provides a ground for the proximal end of coil spring (170), such that coil spring (170) resiliently imparts a distal bias to bracket (500) via upright feature (510). Bracket (500) further includes a laterally presented flange (516) at the distal end of body (502). Flange (516) defines a slot (514).

Figure 11:
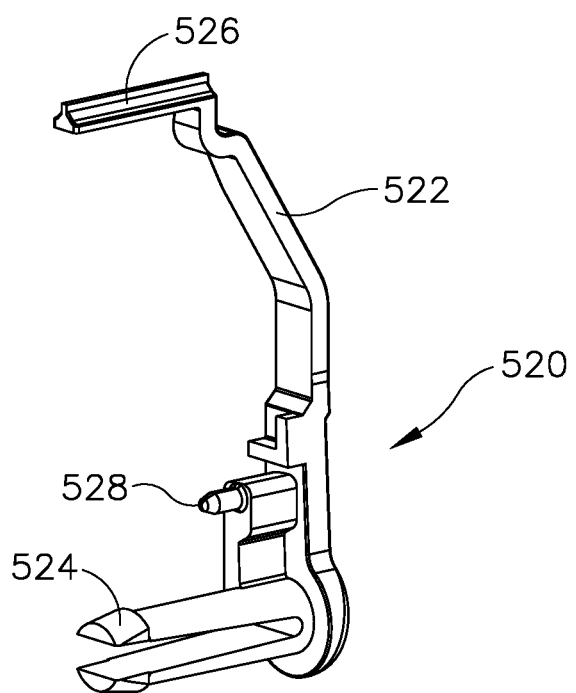
FIG. 11 depicts a perspective view of an indicator member of the handle assembly of FIG. 9.
Figure 12A:
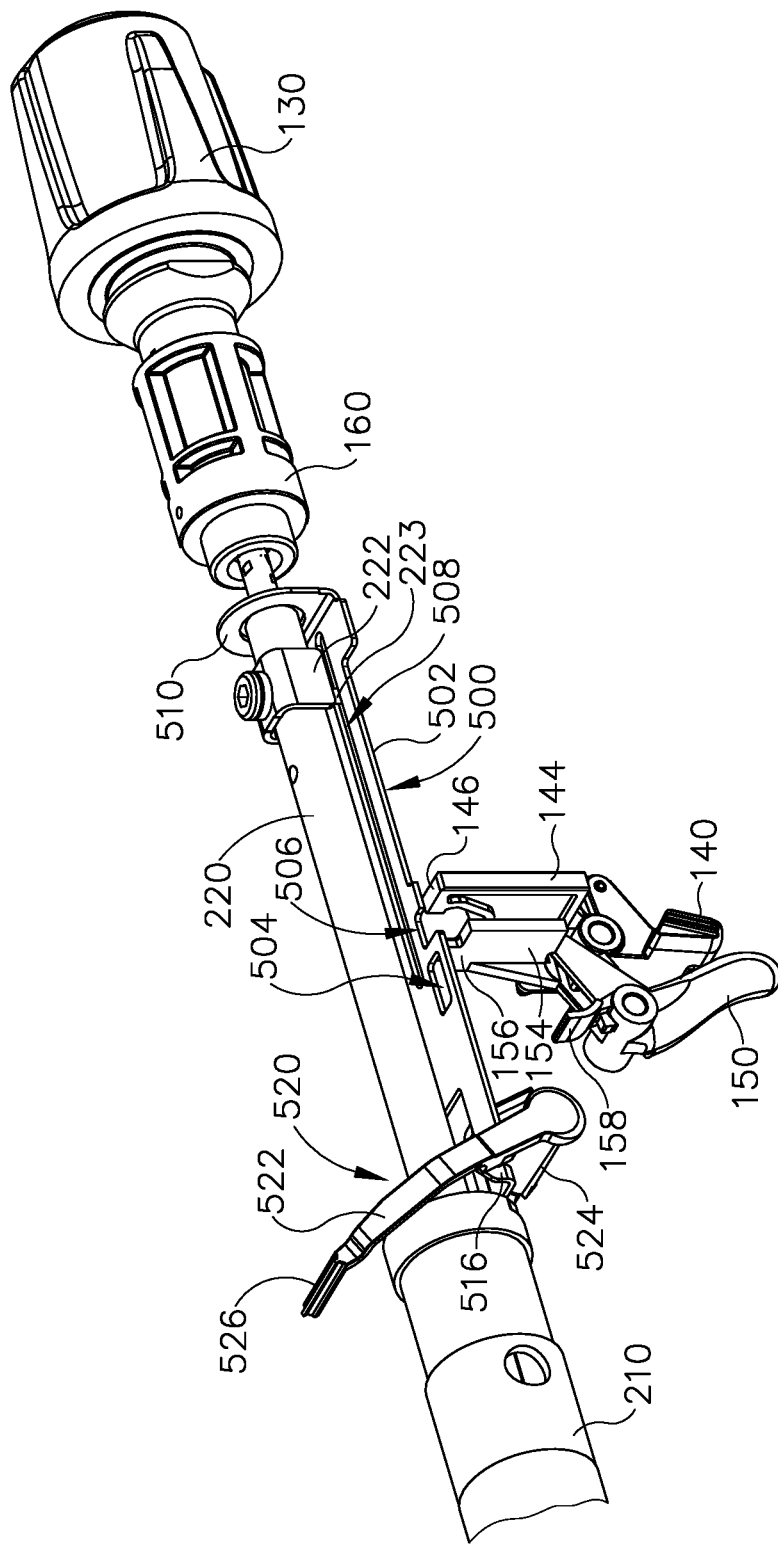
FIG. 12A depicts a perspective view of an anvil actuation assembly of the circular stapler of FIG. 1, an actuation rod in a first position.
Figure 12B:
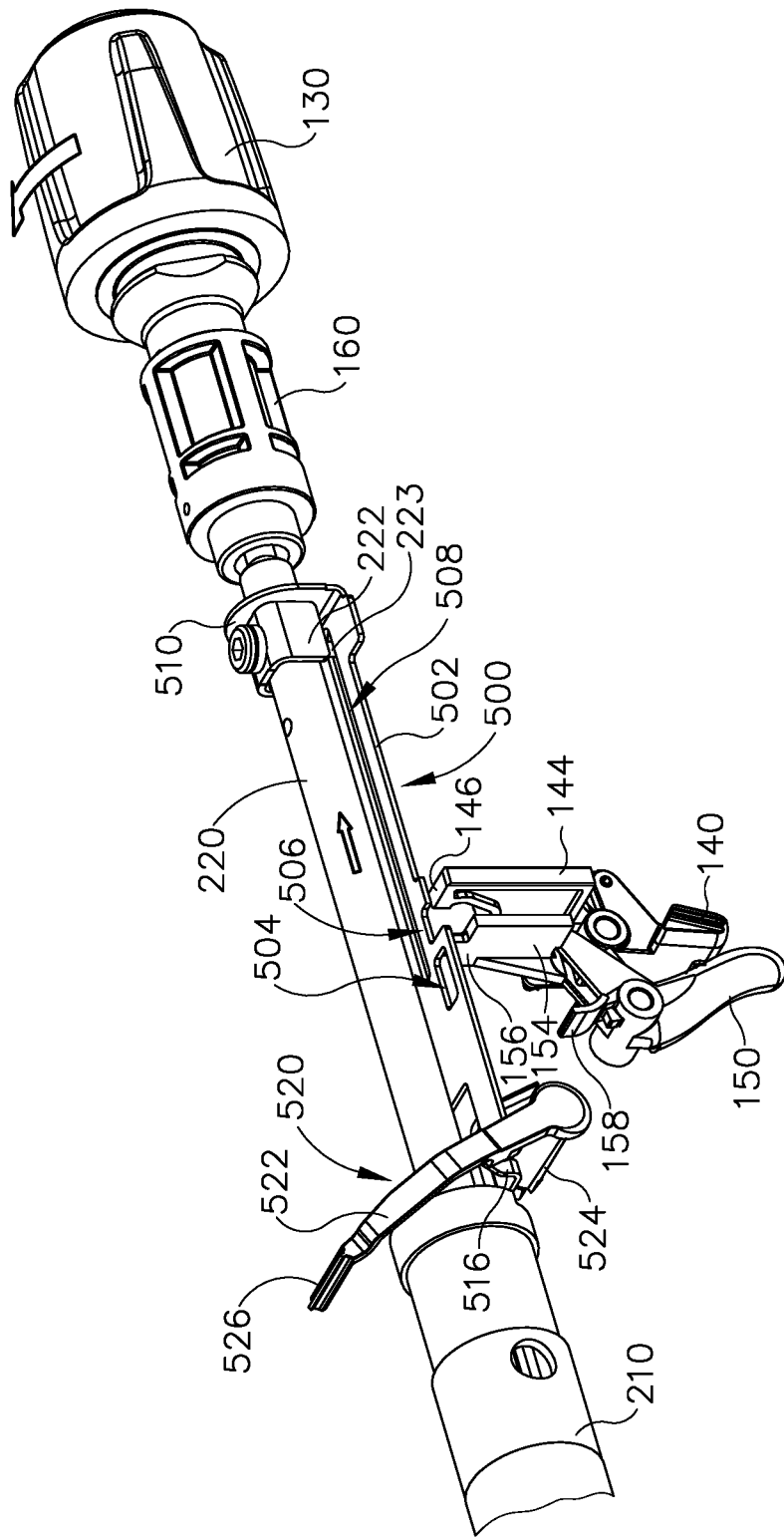
FIG. 12B depicts a perspective view of the anvil actuation assembly of FIG. 12A, with the actuation rod moved to a second position to engage the bracket of FIG. 10.
Figure 12C:
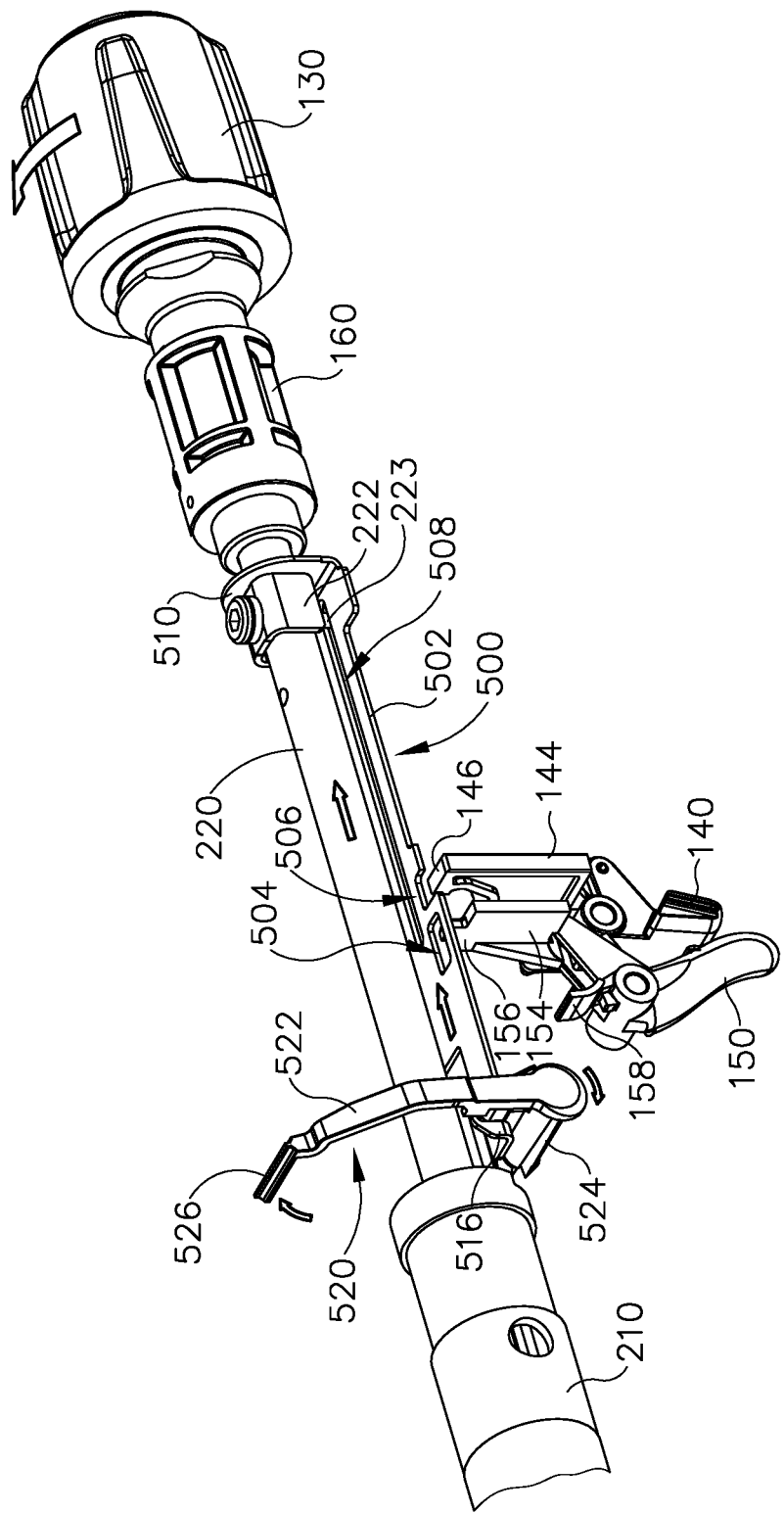
FIG. 12C depicts a perspective view of the anvil actuation assembly of FIG. 12A, with the actuation rod moved to a third position to retract the bracket of FIG. 10 proximally.

As best seen in FIGS. 12B-12C, an indicator member (520) is configured to pivot in response to translation of bracket (500). As best seen in FIG. 11, indicator member (520) comprises an upright arm (522), a snap pin (524) projecting laterally from a lower end of arm (522), an indicator needle (526) projecting laterally from an upper end of arm (522), and a coupling pin (528) projecting laterally from an intermediate region of arm (522). Snap pin (524) is configured to snap into a complementary recess provided by casing (110). Snap pin (524) thereby secures indicator member (520) to casing (110) yet permits indicator member (520) to pivot relative to casing (110) about the longitudinal axis of snap pin (524). Indicator needle (526) is positioned to be visible through window (114) of handle assembly (110) to thereby visually indicate the pivotal position of indicator member (520). Coupling pin (528) is slidably received in slot (514) of flange (516) of bracket (500). This engagement between indicator member (520), casing (110), and bracket (500) provides pivotal movement of indicator member (520) in response to translation of bracket (500).

Bracket (500) is configured to selectively prevent and permit actuation of triggers (140, 150). In particular, slots (504, 506) of bracket (500) are configured to selectively provide clearance for actuation of triggers (140, 150). As shown in FIGS. 12A-12E, safety trigger (140) is pivotably coupled with a first upright member (144). First upright member (144) is coupled with casing (110) such that first upright member (144) is configured to translate upwardly in response to pivoting of safety trigger (140) toward pistol grip (112). However, body (502) of bracket (500) is configured to prevent this movement of first upright member (144) and safety trigger (140) by engaging the upper end (146) of first upright member (144). Body (502) thus blocks movement of first upright member (144) and safety trigger (140) until bracket (500) is moved to a position where slot (506) is aligned with upper end (146) to thereby provide clearance for upward movement of first upright member (144). It should therefore be understood that safety trigger (140) cannot be pivoted toward pistol grip (112) until slot (506) is positioned over upper end (146).

Similarly, firing trigger (150) is pivotably coupled with a second upright member (154). Second upright member (154) is coupled with casing (110) such that second upright member (154) is configured to translate upwardly in response to pivoting of safety trigger (150) toward pistol grip (112). However, body (502) of bracket (500) is configured to prevent this movement of second upright member (154) and firing trigger (150) by engaging the upper end (156) of second upright member (154). Even if safety trigger (140) is pivoted out of the way to otherwise permit movement of firing trigger (150), body (502) blocks movement of second upright member (154) and firing trigger (150) until bracket (500) is moved to a position where slot (504) is aligned with upper end (156) to thereby provide clearance for upward movement of second upright member (154). It should therefore be understood that, even if safety trigger (140) is pivoted out of the way to otherwise permit movement of firing trigger (150), firing trigger (150) cannot be pivoted toward pistol grip (112) until slot (504) is positioned over upper end (156).

Third slot (508) is configured to receive a downwardly projecting boss (223) of clip (222), which is rigidly secured to trocar actuation rod (220). While casing (110) is configured to allow bracket (500) to translate longitudinally within casing (110), casing (110) includes rails, channels, and/or other features that prevent bracket (500) from rotating within casing (110). Thus, the positioning of boss (223) in slot (508) prevents clip (222) and trocar actuation rod (220) from rotating within casing (110). Boss (223) and slot (508) nevertheless allow bracket (500) to translate longitudinally within casing (110) as will be described in greater detail below.

FIGS. 12A-12E depict the above-described components at various stages of operation. In particular, in FIG. 12A, trocar actuation rod (220) is in a distal-most position, such that trocar (330) is in a distal-most position. At this stage, the operator may couple anvil (400) with trocar (330) by inserting trocar (330) into bore (422) until latch members (430) are secured to head (334) of trocar (330). The operator then rotates knob (130), which rotates nut (160). As knob (130) and nut (160) rotate, engagement between coarse helical threading (224) of trocar actuation rod (220) and the complementary feature of nut (160) causes trocar actuation rod (220) to retract proximally at a relatively rapid rate, such that trocar actuation rod (220) reaches the position shown in FIG. 12B. This provides proximal retraction of trocar actuation rod (220) provides retraction of trocar (330) and anvil (400). As trocar actuation rod (220) moves from the position shown in FIG. 12A to the position shown in FIG. 12B, bracket (500) remains stationary. This is due to the fact that clip (222) is spaced apart from upright feature (510) at the stage shown in FIG. 12A and does not engage upright feature (510) until trocar actuation rod (220) reaches the position shown in FIG. 12B.

After reaching the stage shown in FIG. 12B, the operator may continue rotating knob (130) and nut (160), which causes further proximal retraction of trocar actuation rod (220) as shown in FIG. 12C. This of course causes further proximal retraction of trocar (330) and anvil (400). As trocar actuation rod (220) moves from the position shown in FIG. 12B to the position shown in FIG. 12C, clip (222) bears against bracket (500), driving bracket (500) proximally. This proximal movement of bracket (500) causes indicator member (520) to pivot from the position shown in FIG. 12B to the position shown in FIG. 12C due to the positioning of pin (528) in slot (514) of flange (516).

As indicator member (520) pivots from the position shown in FIG. 12B to the position shown in FIG. 12C, the operator may observe the position of indicator needle (526) through window (114) of handle assembly (110). As noted above, a series of hash marks, colored regions, and/or other fixed indicators may be positioned adjacent to window (114) in order to provide a visual context for indicator needle (526), thereby facilitating operator evaluation of the position of needle (526) within window (114). It should be understood that the position of needle (526) within window (114) will be indicative of the longitudinal position of trocar (330) and anvil (400). The position of needle (526) within window (114) will thus indicate the gap distance (d) between opposing surfaces (412, 322) of anvil (400) and stapling head assembly (300). While observing the position of needle (526) within window (114), the operator may rotate knob (130) clockwise or counterclockwise to further retract or advance trocar (330) and anvil (400), thereby providing fine adjustment of the gap distance (d) until a desired gap distance (d) is reached within an appropriate range.

In order to provide fine control of the gap distance (d) adjustment at the stage shown in FIG. 12C, trocar actuation rod (220) will be at a longitudinal position where fine helical threading (226) is engaged with a complementary feature of knob (130) and coarse helical threading (224) is disengaged from the complementary feature of nut (160). In some versions, coarse helical threading (224) disengages nut (160) and fine helical threading (226) begins to engage knob (130) once trocar actuation rod (220) reaches the longitudinal position shown in FIG. 12B (i.e., when clip (222) first engages upright member (510)). In some other versions, the transition from engagement by coarse helical threading (224) to fine helical threading (226) occurs sometime between the stage shown in FIG. 12B and the stage shown in FIG. 12C. Other suitable stages at which the coarse-to-fine transition may occur will be apparent to those of ordinary skill in the art in view of the teachings herein. It should also be understood that some alternative versions of trocar actuation rod (220) may have just a single threading section, with the pitch of the threading being consistent along the length of the threading. In other words, trocar actuation rod (220) does not necessarily need to have two different sections of threading (224, 226) with different pitches.

At the stage shown in FIG. 12C, slot (506) is aligned with upper end (146) to thereby provide clearance for upward movement of first upright member (144). Similarly, slot (504) is aligned with upper end (156) to thereby provide clearance for upward movement of second upright member (154). In the present example, slots (504, 506) are sized and positioned such that slots (504, 506) only provide clearance for upward movement of upright members (144, 154) when the gap distance (d) is within a clinically acceptable range. By way of example only, a "clinically acceptable range" for the gap distance (d) may be between approximately 0.110 inches and approximately 0.040 inches. As another merely illustrative example, a "clinically acceptable range" for the gap distance (d) may be between approximately 0.110 inches and approximately 0.020 inches. Even when slots (504, 506) are positioned to provide clearance for upward movement of upright members (144, 154) as shown in FIG. 12C, safety trigger (140) will still block pivotal movement of firing trigger (150) about a pin (152) (FIG. 9) when safety trigger (140) is in the non-actuated position shown in FIG. 12C. Thus, in order to enable movement of firing trigger (150), the operator will need to first actuate safety trigger (140) about a pin (142) (FIG. 9) from the position shown in FIG. 12C to the position shown in FIG. 12D.

Figure 12D:
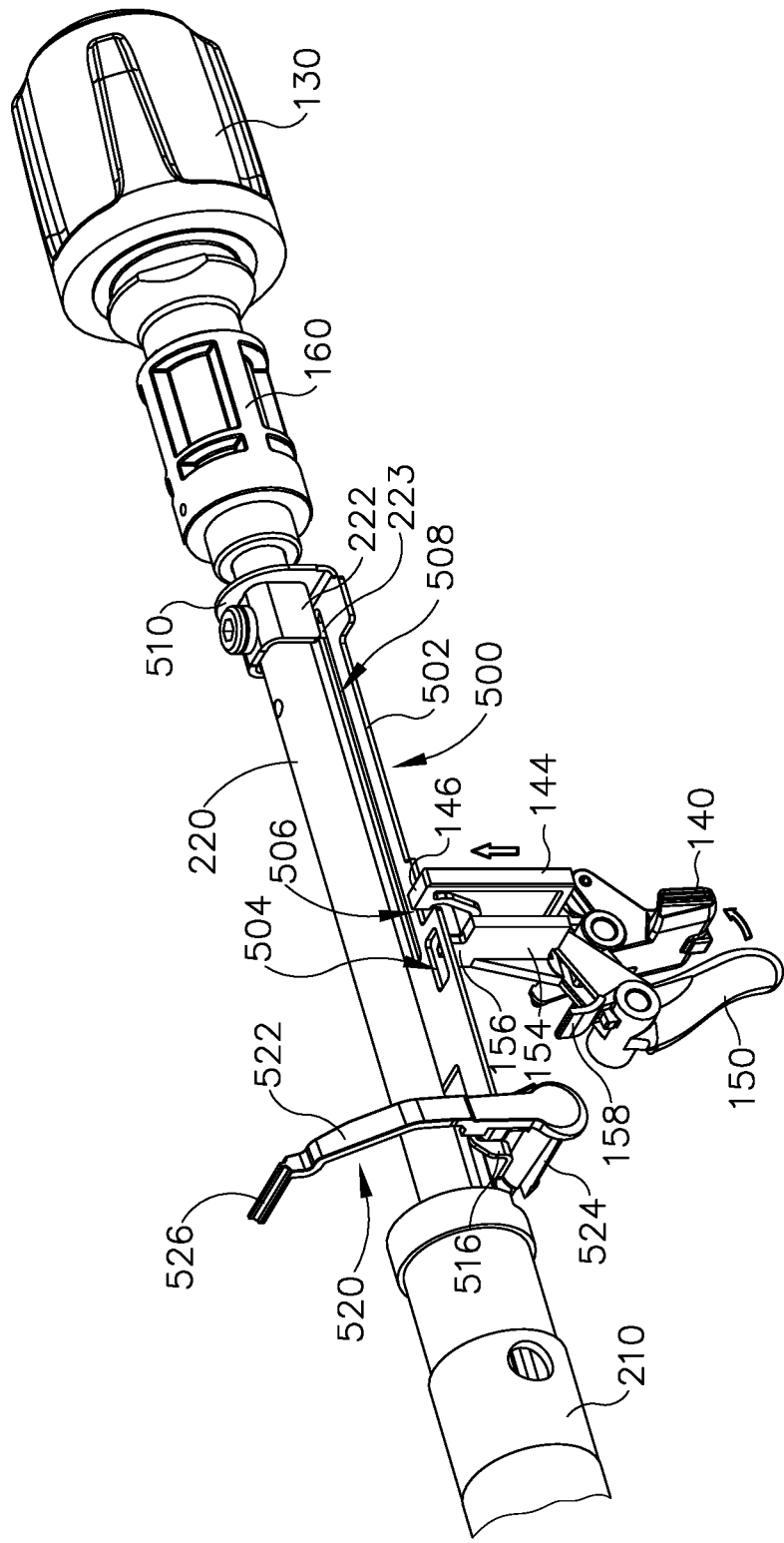
FIG. 12D depicts a perspective view of the anvil actuation assembly of FIG. 12A, with a safety trigger pivoted from a first position to a second position.

As shown in FIG. 12D, upper end (146) passes through slot (506) as safety trigger (140) is pivoted from the position shown in FIG. 12C to the position shown in FIG. 12D. It should be understood that this movement of upper end (146) would not be possible at the stages shown in FIGS. 12A-12B (when the gap distance (d) is too great) because body (502) would physically block upward movement of upright member (144), thereby physically blocking pivotal movement of safety trigger (140). In the present example, a cap (not shown) incorporated into knob (130) prevents knob (130) from rotating to a point where anvil (400) would be retracted too far proximally (such that the gap distance (d) is too small). In some other variations, even if knob (130) were to permit anvil (400) to be retracted too far proximally (such that the gap distance (d) is too small), body (502) would physically block upward movement of upright member (144), thereby physically blocking pivotal movement of safety trigger (140), in the event that the operator retracts trocar (330) and anvil (400) too far proximally (such that the gap distance (d) is too small). Regardless of whether body (502), knob (130), or some other feature prevents actuation when the gap distance (d) would be too small, it should be understood that instrument (10) permits actuation of safety trigger (140) only when the gap distance (d) is within the clinically acceptable range.

Figure 12E:
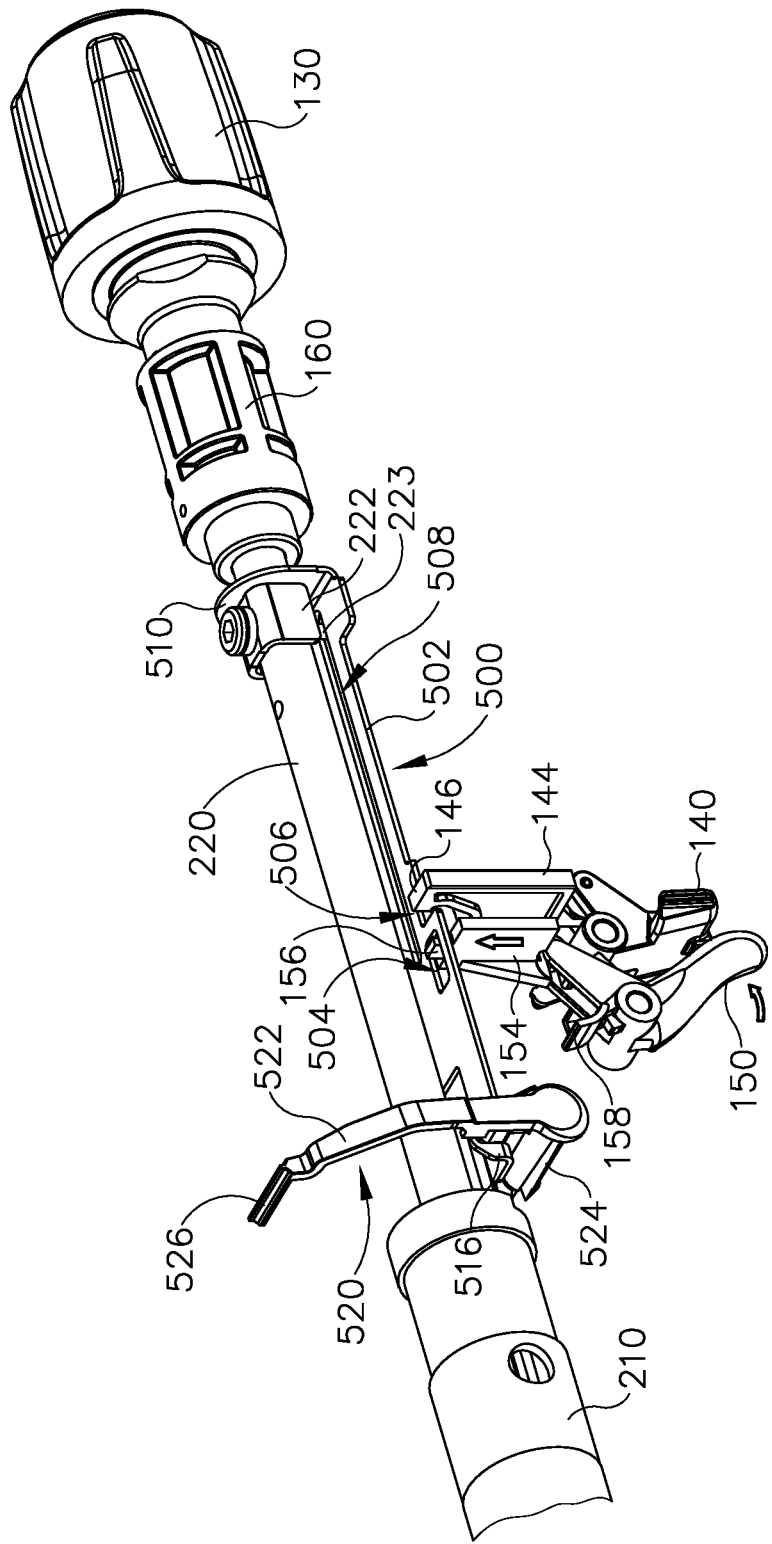
FIG. 12E depicts a perspective view of the anvil actuation assembly of FIG. 12A, with a firing trigger pivoted from a first position to a second position.
Figure 13:
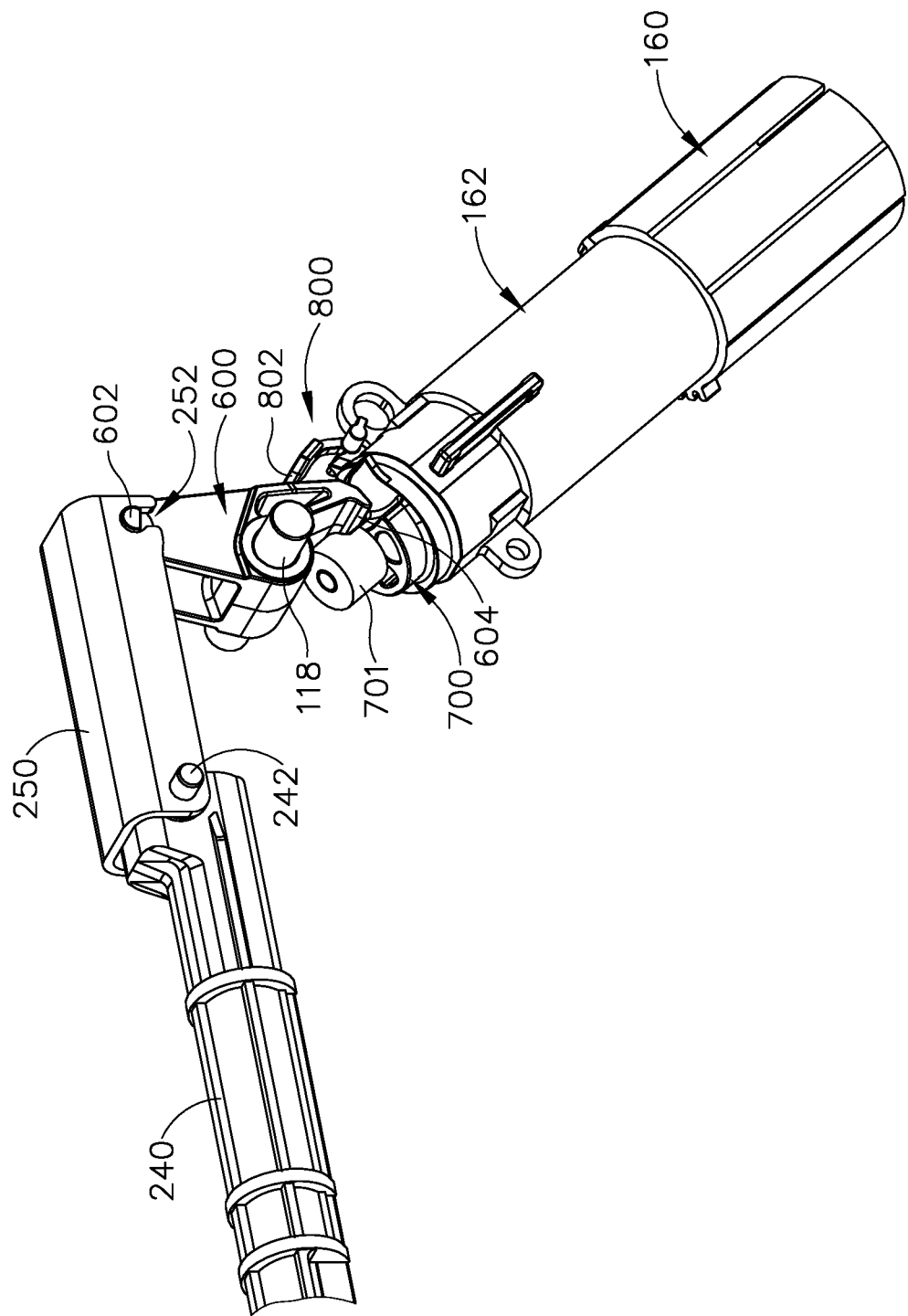
FIG. 13 depicts a perspective view of a stapling head actuation assembly of the circular stapler of FIG. 1.

As noted above, safety trigger (140) is configured to prevent actuation of firing trigger (150) until safety trigger (140) has been actuated. Once safety trigger (140) has been actuated, the operator may actuate firing trigger (150) from the position shown in FIG. 12D to the position shown in FIG. 12E. As shown in FIG. 12E, upper end (156) passes through slot (504) as firing trigger (150) is pivoted from the position shown in FIG. 12D to the position shown in FIG. 12E. It should be understood that, even in the complete absence of safety trigger (140), this movement of upper end (156) would not be possible at the stages shown in FIGS. 12A-12B (when the gap distance (d) is too great) because body (502) would physically block upward movement of upright member (154), thereby physically blocking pivotal movement of firing trigger (150). It should also be understood that body (502) would also physically block upward movement of upright member (154), thereby physically blocking pivotal movement of firing trigger (150), in the event that the operator retracts trocar (330) and anvil (400) too far proximally (such that the gap distance (d) is too small). Thus, even in the complete absence of safety trigger (140), firing trigger (150) may only be actuated when the gap distance (d) is within the clinically acceptable range.

Firing trigger (150) of the present example includes an integral actuation paddle (158). Paddle (158) pivots forwardly as firing trigger (150) pivots from the position shown in FIG. 12D to the position shown in FIG. 12E. Paddle (158) is configured to actuate a switch of a motor activation module (180), which is shown in FIG. 9, when firing trigger (150) pivots from the position shown in FIG. 12D to the position shown in FIG. 12E. Motor activation module (180) is in communication with battery pack (120) and motor (160), such that motor activation module (180) is configured to provide activation of motor (160) with electrical power from battery pack (120) in response to paddle (158) actuating the switch of motor activation module (180). Thus, motor (160) will be activated when firing trigger (150) is pivoted from the position shown in FIG. 12D to the position shown in FIG. 12E. This activation of motor (160) will actuate stapling head assembly (300) as described in greater detail below.

3. Exemplary Stapling Head Actuation Assembly

FIGS. 13-20D show various components that are operable to actuate stapling head assembly (300). These components include motor (160), a gearbox (162), a rotary cam member (700), a cam follower (600), drive bracket (250) and stapling head assembly driver (240). Gearbox (162) is coupled with a drive shaft of motor (160) and is further coupled with cam member (700). Activation of motor (160) thus causes rotation of cam member (700) via gearbox (162). Various suitable configurations that may be used for gearbox (162) will be apparent to those of ordinary skill in the art in view of the teachings herein. Cam member (700) is configured to interact with cam follower (160) to pivot cam follower (160) in two angular directions about a pin (118) as will be described in greater detail below. Pin (118) is coupled with casing (110). A bushing (701) provides rotary support to cam member (700) relative to casing (110).

Figure 14:
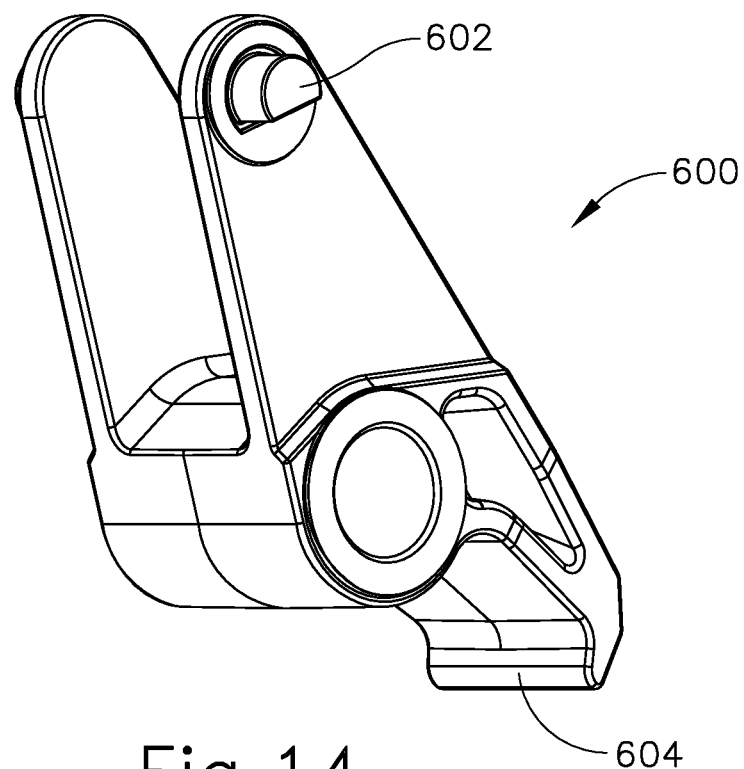
FIG. 14 depicts a perspective view of a cam follower of the stapling head actuation assembly of FIG. 13.
Figure 15:
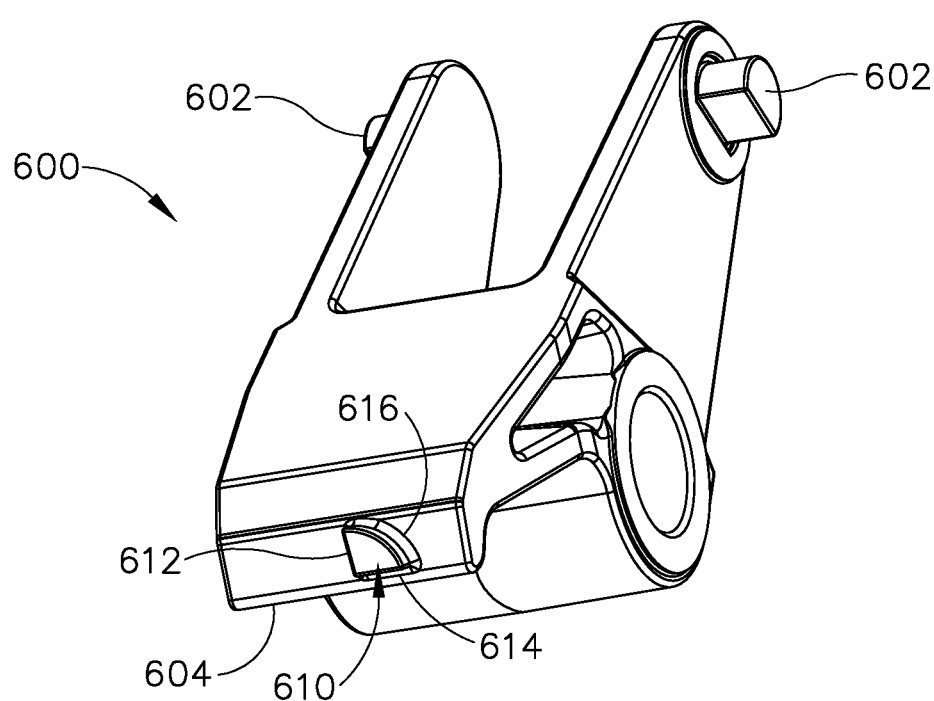
FIG. 15 depicts another perspective view of the cam follower of FIG. 14.

Cam follower (600) is pivotably coupled with drive bracket (250) via a pair of integral pins (602), which are received in complementary notches (252) of drive bracket (250). As shown in FIGS. 14-15, cam follower (600) includes a first bearing feature (604) and a second bearing feature (610). First bearing feature (604) consists of a rounded, horizontally extending surface. Second bearing feature (610) is shaped like a quarter-pie defined by a straight vertical surface (612), a horizontally extending surface (614), and a curved surface (616). Second bearing feature (610) projects proximally relative to first bearing feature (504).

Figure 16:
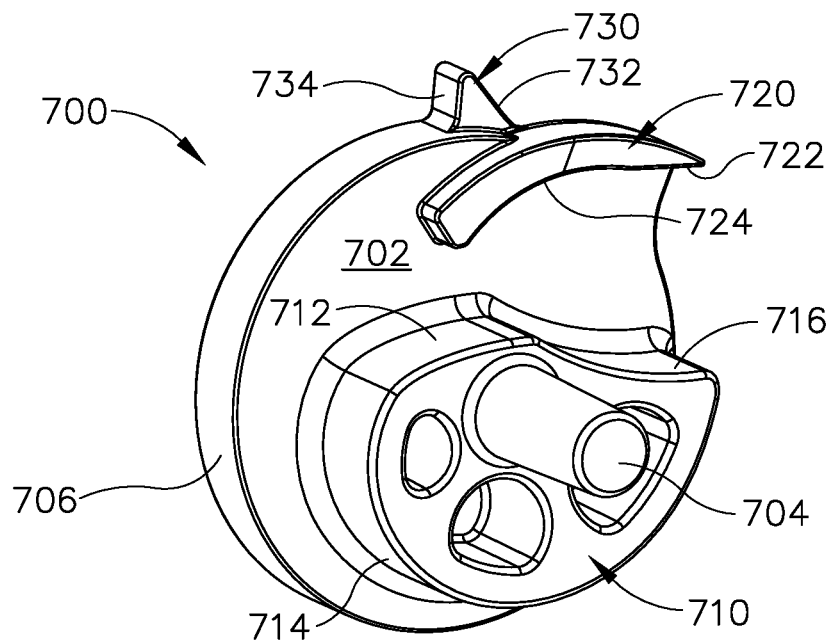
FIG. 16 depicts a perspective view of a rotary cam of the stapling head actuation assembly of FIG. 13.
Figure 17:
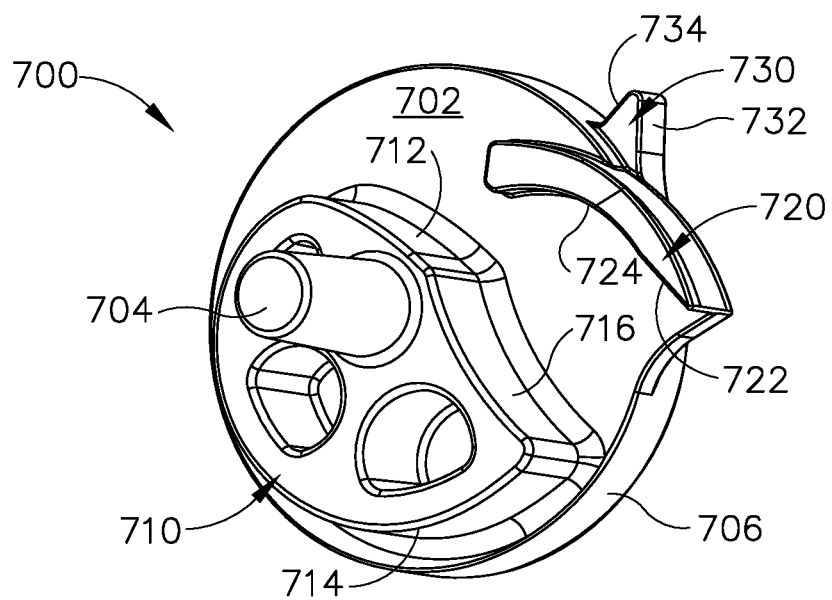
FIG. 17 depicts another perspective view of the rotary cam of FIG. 16.

FIGS. 16-17 show cam member (700) in greater detail. Cam member (700) comprises a distal face (702), a distally projecting post (704), and an outer circumferential surface (706). A first cam feature (710) and a second cam feature (720) project distally from distal face (702). Post (704) engages bushing (701). First cam feature (710) comprises a first surface region (712), a second surface region (714), and a third surface region (716). First surface region (712) is convexly defined by a relatively large radius of curvature, such that first surface region (712) is nearly flat. Second surface region (714) is convexly defined by a progressively increasing radius of curvature. Third surface region (716) is concavely defined by a relatively large radius of curvature. In addition to projecting distally from distal face (702), second cam feature (720) projects outwardly from outer circumferential surface (706). Second cam feature (720) includes a first surface region (722) and a second surface region (724). First surface region (722) is substantially flat while second surface region (724) is concavely curved. The origin of the radius of curvature for each curved surface region (712, 714, 716, 724) is offset from the center of post (704).

Figure 18A:
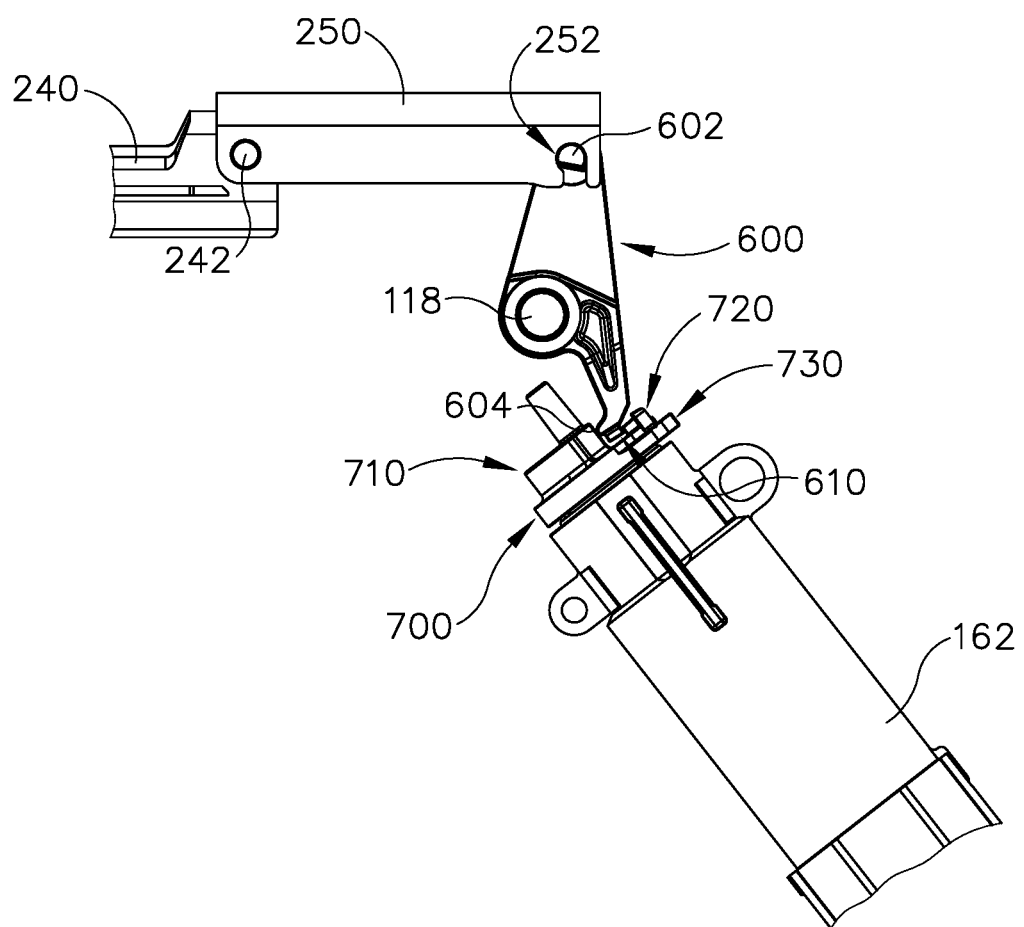
FIG. 18A depicts a side elevational view of the stapling head actuation assembly of FIG. 13, with the rotary cam in a first angular position and the cam follower in a first pivotal position.
Figure 18B:
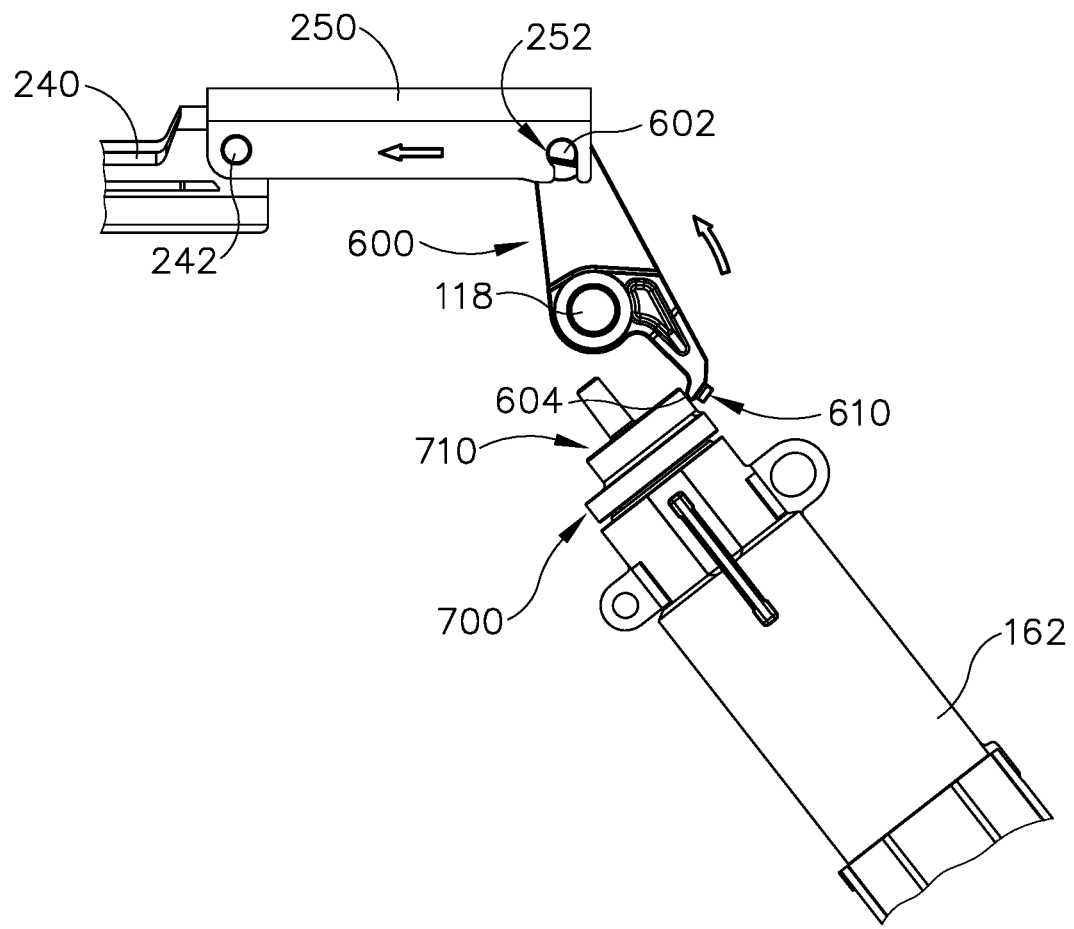
FIG. 18B depicts a side elevational view of the stapling head actuation assembly of FIG. 13, with the rotary cam in a second angular position and the cam follower in a second pivotal position.

FIGS. 18A-18B show the general interaction between cam follower (600) and first and second cam features (710, 720), though this interaction will be described in greater detail below with reference to FIGS. 20A-20D. As cam member (700) is rotated from the position shown in FIG. 18A to the position shown in FIG. 18B, first cam feature (710) bears against first bearing feature (604) of cam follower (600), causing cam follower to pivot about pin (118). In the view shown in FIGS. 18A-18B, cam follower (600) pivots counterclockwise as cam member (700) is rotated from the position shown in FIG. 18A to the position shown in FIG. 18B. As can be seen in the transition from FIG. 18A to FIG. 18B, this counterclockwise pivoting of cam follower (600) drives drive bracket (250) and stapling head assembly driver (240) distally, thereby actuating stapling head assembly (300). As cam member (700) continues to rotate in the same direction back toward the position shown in FIG. 18A, second cam feature (720) engages and bears against second bearing feature (610) of cam follower (600), causing cam follower (600) to pivot clockwise about pin (118). This clockwise pivoting of cam follower (600) about pin (118) retracts drive bracket (250) and stapling head assembly driver (240) proximally back toward the position shown in FIG. 18A.

Figure 19A:
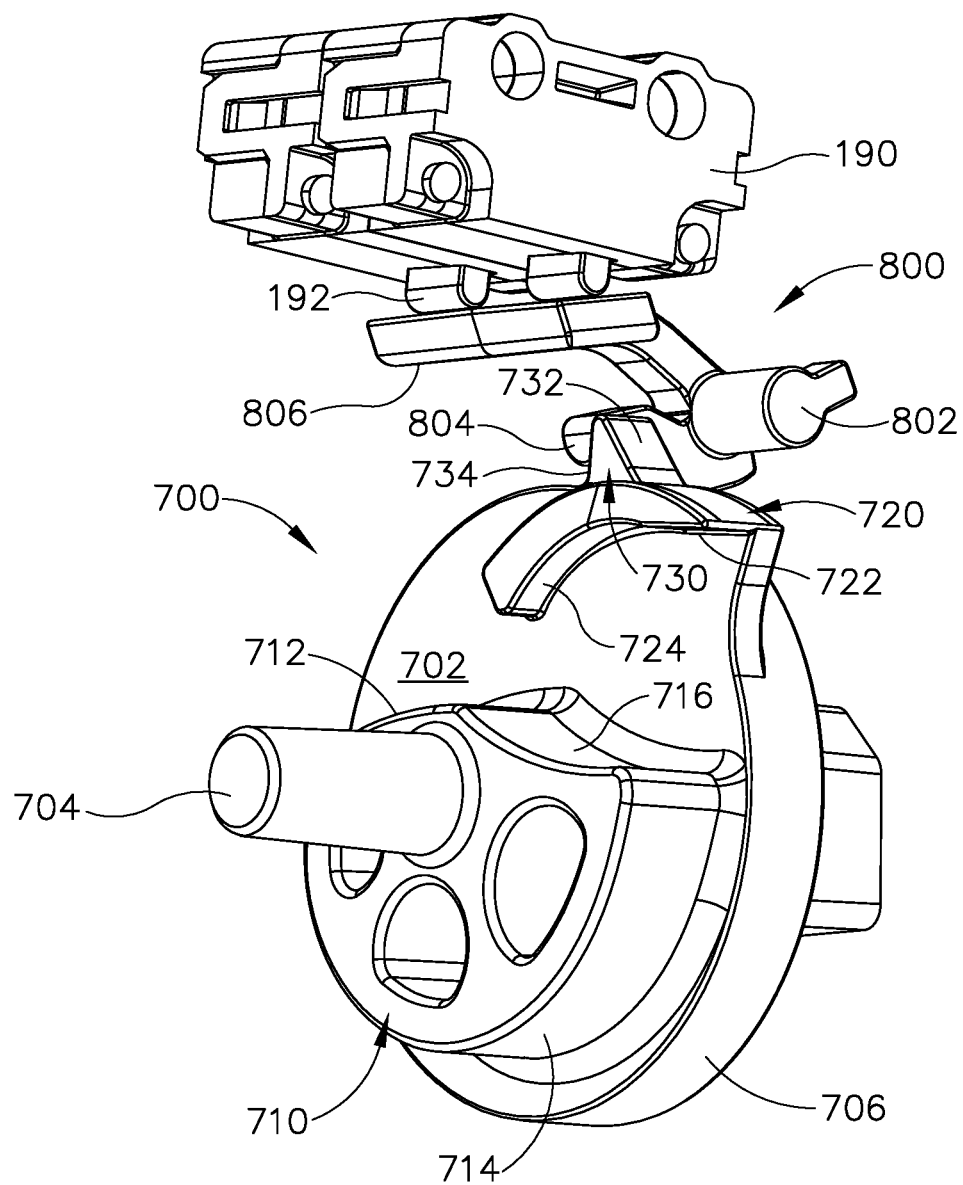
FIG. 19A depicts a perspective view of the rotary cam of FIG. 16, a rocker member, and a stop switch, with the rotary cam in a first angular position and the rocker member in a first pivotal position.
Figure 19B:
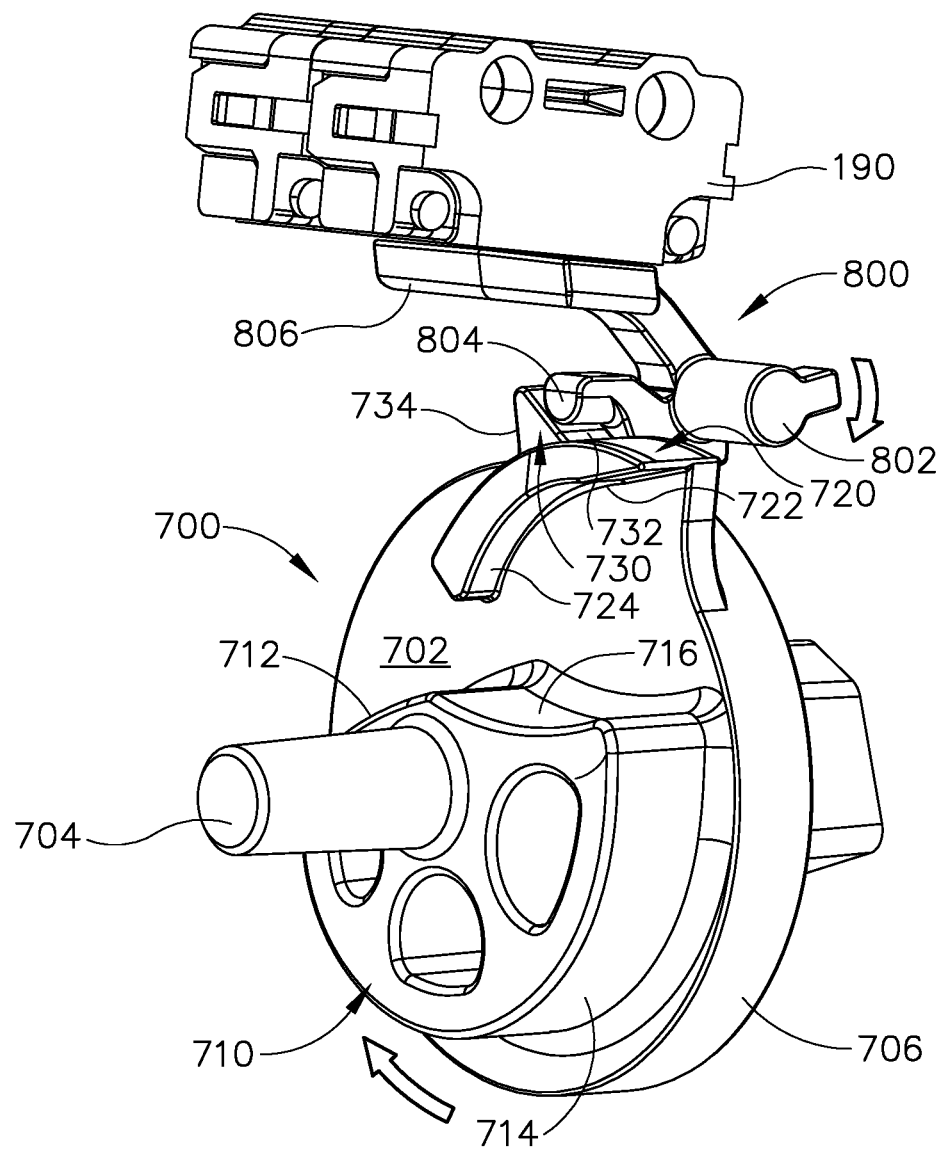
FIG. 19B depicts a perspective view of the rotary cam of FIG. 16, the rocker member of FIG. 19A, and the stop switch of FIG. 19A, with the rotary cam in a fourth angular position and the rocker member in a second pivotal position.

Referring back to FIGS. 16-17, a third cam feature (730) projects outwardly from outer circumferential surface (706). Third cam feature (730) comprises a first surface region (732) and a second surface region (734). First surface region (732) is flat and is oriented generally tangentially relative to outer circumferential surface (706). Second surface region (732) is also flat and is oriented radially outwardly relative to outer circumferential surface (706). Third cam feature (730) is configured to interact with a rocker member (800)

as shown in FIGS. 19A-19B. Rocker member (800) comprises an integral pin (802), a bearing member (804), and a paddle (806). Pin (802) is pivotably coupled with casing (110), such that rocker member (800) is pivotable within casing (110) about the longitudinal axis defined by pin (802). Bearing member (804) is configured to interact with third cam feature (730) as will be described in greater detail below. Paddle (806) is configured to actuate a pair of switch buttons (192) of a motor stop module (190) as will also be described in greater detail below.

FIG. 19A shows cam member (700) in the same position as shown in FIG. 18A. At this stage, second surface region (734) of third cam feature (730) is adjacent to bearing member (804) of rocker member (800). FIG. 19B shows cam member (700) in a position where cam member (700) has been rotated past the position shown in FIG. 18B and back toward the position shown in FIG. 18A. However, cam member (700) has not completed a full revolution. At the stage shown in FIG. 19B, first surface region (732) has engaged and borne against bearing member (804), thereby pivoting rocker member (800) about the longitudinal axis defined by pin (802). This has caused paddle (806) to actuate switch buttons (192) of motor stop module (190). Motor stop module (190) is configured to prevent motor (160) from further activation when switch buttons (192) have been actuated. In some versions, motor stop module (190) creates a short circuit when switch buttons (192) are actuated, thereby stopping further activation of motor (160). Also in some versions, motor stop module (190) couples battery pack (120) with a power sink, in addition to short circuiting motor (160), when switch buttons (192) are actuated. This may result in discharge of battery pack (120) in addition to stopping activation of motor (160) once an actuation stroke of stapling head assembly (300) has been completed. By way of example only, motor stop module (190) may be configured and operable in accordance with at least some of the teachings of U.S. Pub. No. 2015/0083774, issued as U.S. Pat. No. 9,907,552 on Mar. 6, 2018, the disclosure of which is incorporated by reference herein. Other suitable configurations will be apparent to those of ordinary skill in the art in view of the teachings herein.

Figure 20A:
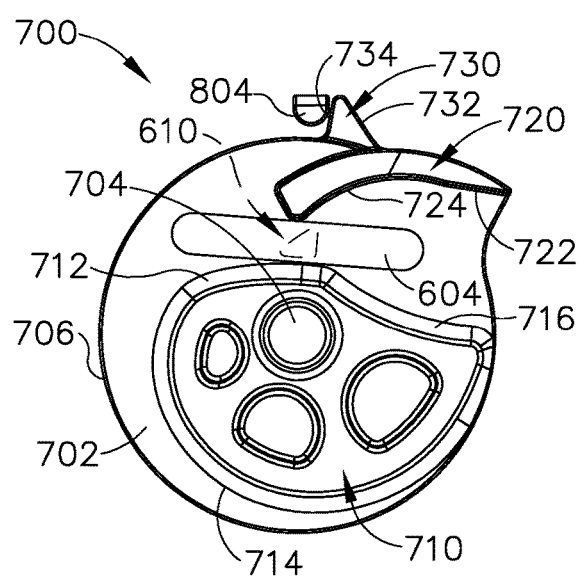
FIG. 20A depicts a schematic end view of the rotary cam of FIG. 16, the cam follower of FIG. 14, and the rocker member of FIG. 19A, with the rotary cam in the first angular position, the cam follower in the first pivotal position, and the rocker member in the first pivotal position.

FIGS. 20A-20D schematically depict the interaction between cam member (700), features of cam follower (600), and features of rocker member (800) as cam member (700) rotates. It should be understood that the rotation of cam member (700) throughout the stages shown in FIGS. 20A-20D is driven by motor (160) and gearbox (162). FIG. 20A shows cam member (700) in the same position as shown in FIGS. 18A and 19A. At this stage, first bearing feature (604) of cam follower (600) is positioned on first surface region (712) and bearing member (804) or rocker member (800) is adjacent to second surface region (734) of third cam feature (730). Also at this stage, knife member (340) and staple driver member (350) are in proximal positions, such that stapling head assembly (300) is in a non-actuated state. As cam member (700) is rotated to the position shown in FIG. 20B, second surface region (714) bears against bearing member (610), thereby driving bearing member (610) upwardly. This causes cam follower (600) to pivot about pin (118) to the position shown in FIG. 18B. Cam follower (600) thus drives knife member (340) and staple driver member (350) distally via drive bracket (250) and stapling head assembly driver (240). Stapling head assembly (300) is thus in an actuated state at the stage shown in FIG. 20B. In some versions, cam member (700) rotates through an angular range of approximately 270° in order to transition stapling head assembly (300) from the non-actuated state to the actuated state.

Figure 20B:
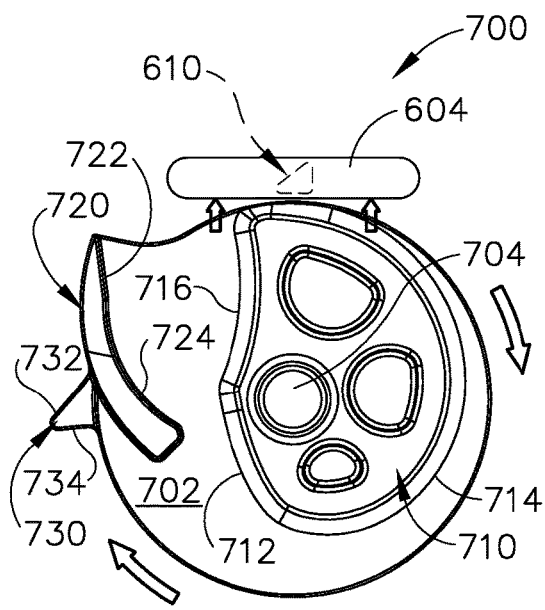
FIG. 20B depicts a schematic end view of the rotary cam of FIG. 16 and the cam follower of FIG. 14, with the rotary cam in the second angular position, the cam follower in the second pivotal position, and the rocker member of FIG. 19A in the first pivotal position.
Figure 20C:
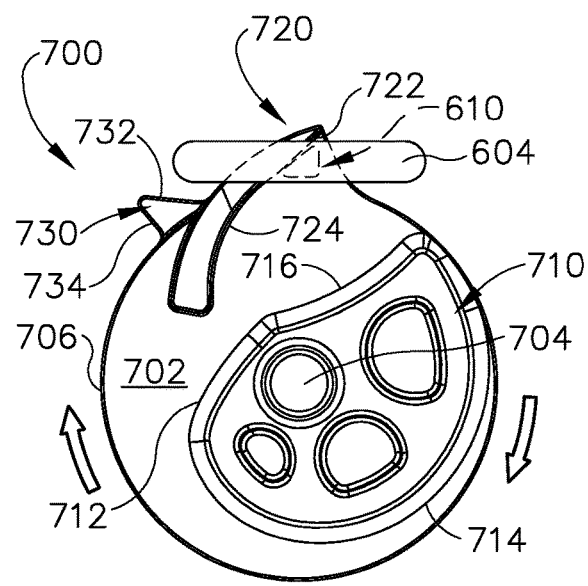
FIG. 20C depicts a schematic end view of the rotary cam of FIG. 16 and the cam follower of FIG. 14, with the rotary cam in a third angular position, the cam follower in the second pivotal position, and the rocker member of FIG. 19A in the first pivotal position.

After stapling head assembly (300) has been actuated, cam member (700) continues to rotate to the position shown in FIG. 20C. At this stage, first surface region (722) of second cam member (720) begins to engage curved surface (616) of second bearing feature (610) of cam follower (600). As cam member (700) continues to rotate to the position shown in FIG. 20D, second surface region (724) engages curved surface (616) of second bearing feature (610), driving second bearing feature (610) downwardly. This causes cam follower (600) to pivot about pin (118) back from the position shown in FIG. 18B toward the position shown in FIG. 18A. Cam follower (600) thus drives knife member (340) and staple driver member (350) proximally via drive bracket (250) and stapling head assembly driver (240). In addition, first surface region (732) has engaged and borne against bearing member (804), thereby pivoting rocker member (800) about the longitudinal axis defined by pin (802) at the stage shown in FIG. 20D. Rocker member (800) is thus in the same state in FIG. 20D as shown in FIG. 19B. Motor stop module (190) has thus been actuated at the stage shown in FIG. 20D.

It should be understood from the foregoing that cam member (700) is operable to drive knife member (340) and staple driver member (350) distally, then drive knife member (340) and staple driver member (350) proximally and actuate motor stop module (190) by rotating in a single angular direction through the range of motion shown in FIGS. 20A-20D. Other suitable ways in which knife member (340), staple driver member (350), and motor stop module (190) may be actuated will be apparent to those of ordinary skill in the art in view of the teachings herein.

E. Exemplary Anastomosis Procedure

Figure 21A:
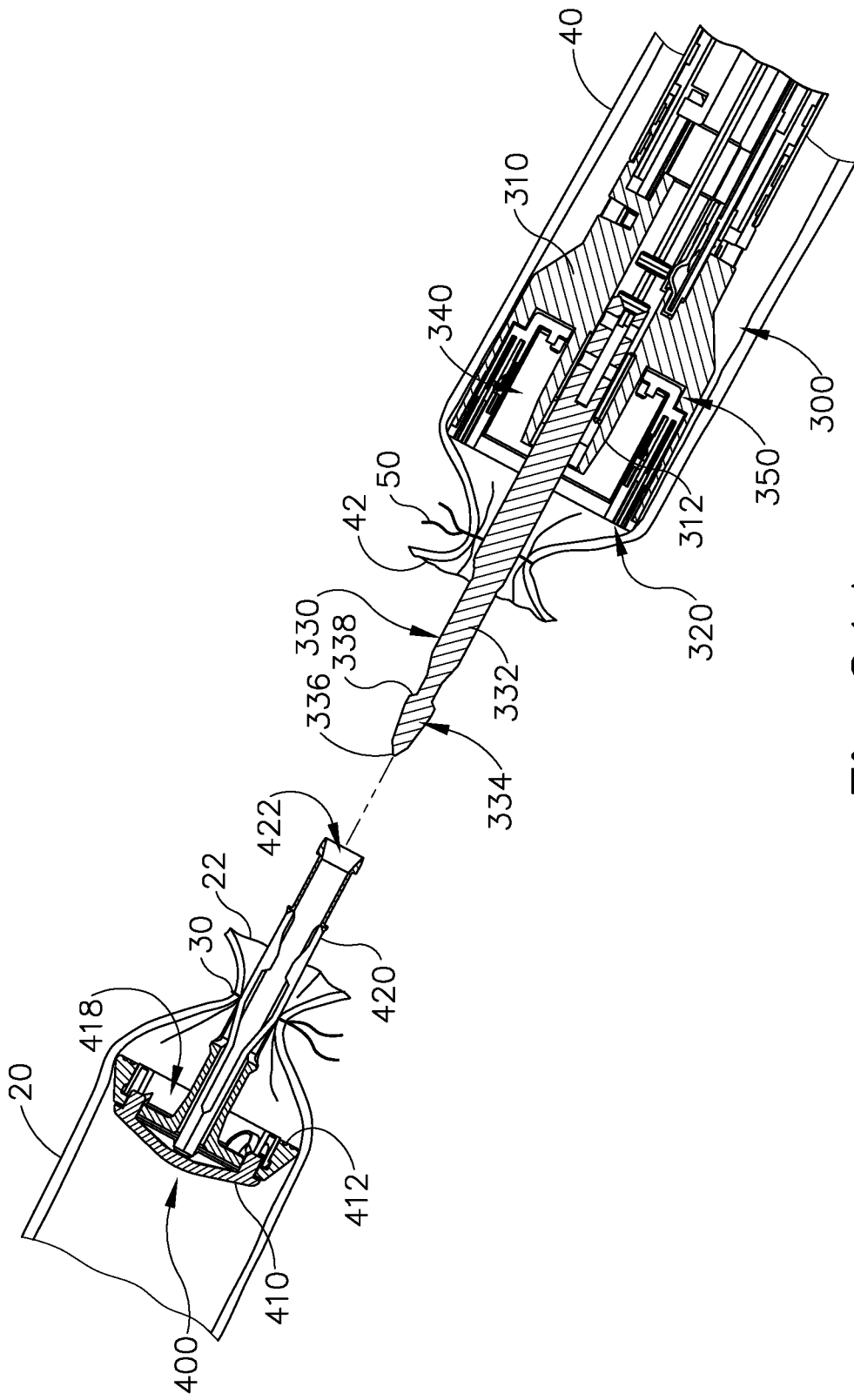
FIG. 21A depicts a cross-sectional side view of the anvil of FIG. 3 positioned within a first section of a digestive tract and the stapling head assembly of FIG. 6 positioned in a second section of the digestive tract, with the anvil separated from the stapling head assembly.
Figure 21B:
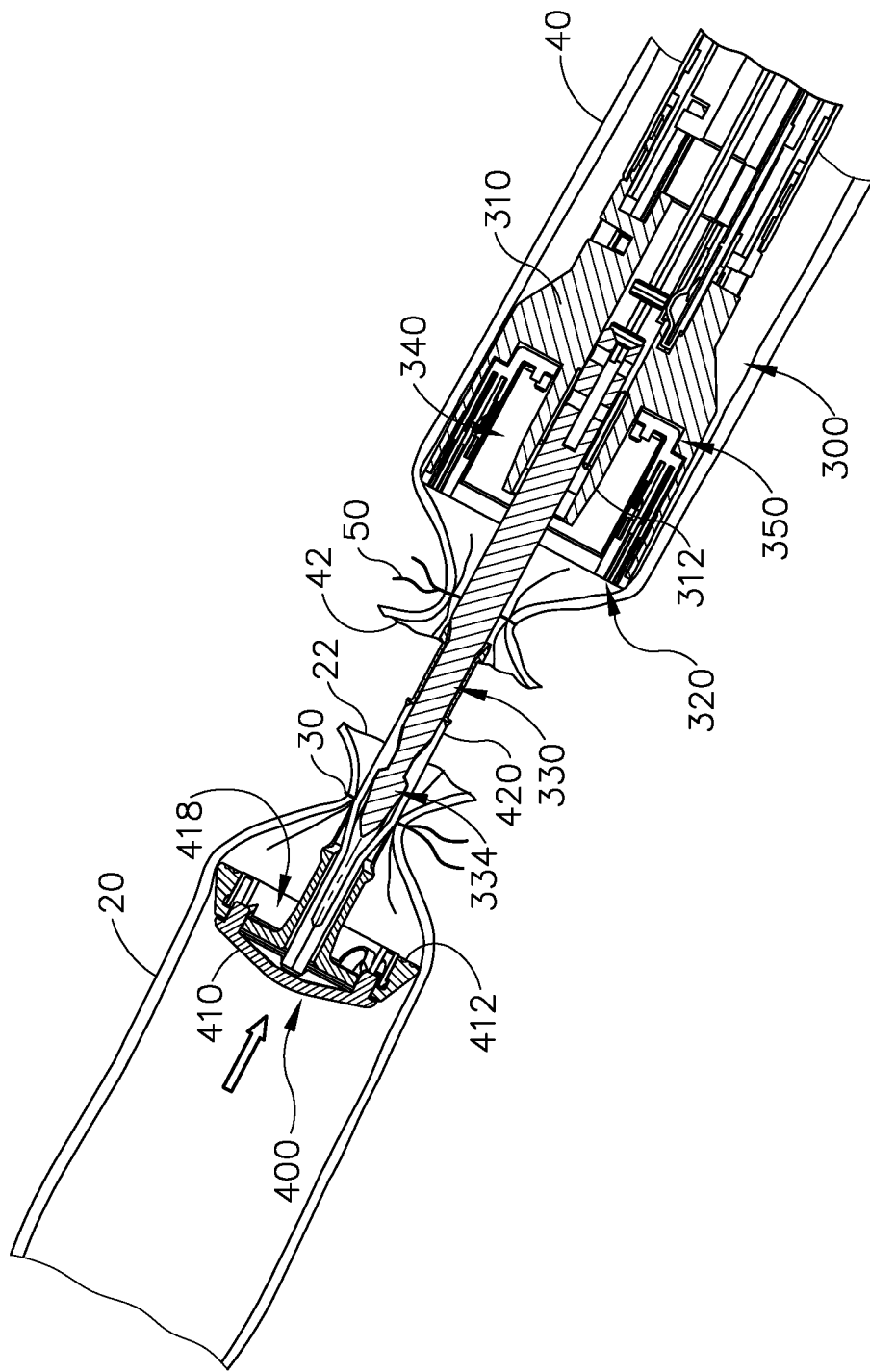
FIG. 21B depicts a cross-sectional side view of the anvil of FIG. 3 positioned within the first section of the digestive tract and the stapling head assembly of FIG. 6 positioned in the second section of the digestive tract, with the anvil secured to the stapling head assembly.
Figure 21C:
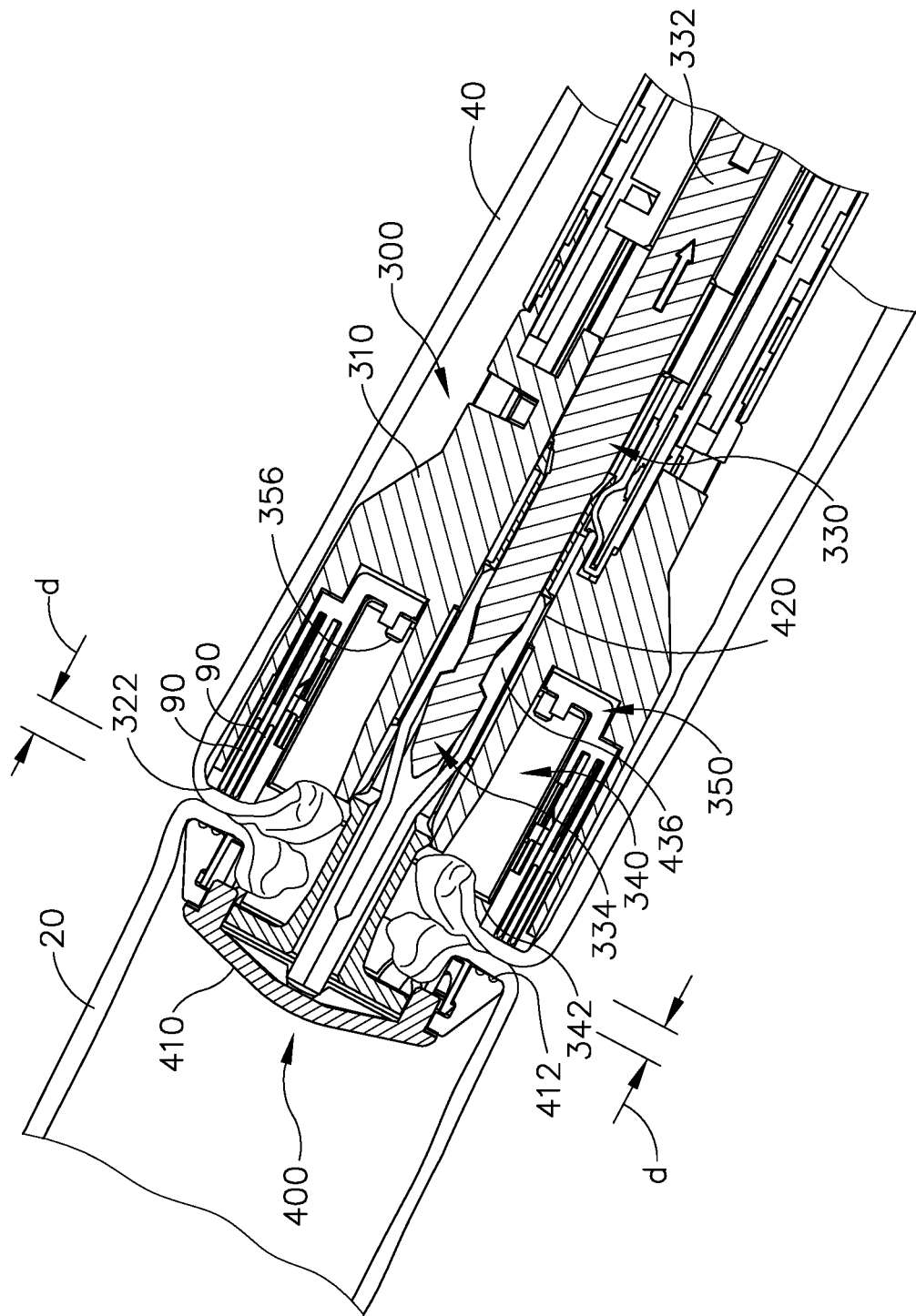
FIG. 21C depicts a cross-sectional side view of the anvil of FIG. 3 positioned within the first section of the digestive tract and the stapling head assembly of FIG. 6 positioned in the second section of the digestive tract, with the anvil retracted toward the stapling head assembly to thereby clamp tissue between the anvil and the stapling head assembly.

FIGS. 21A-21E show instrument (10) being used to form an anastomosis (70) between two tubular anatomical structures (20, 40). By way of example only, the tubular anatomical structures (20, 40) may comprise sections of a patient's esophagus, sections of a patient's colon, other sections of the patient's digestive tract, or any other tubular anatomical structures. As shown in FIG. 21A, anvil (400) is positioned in one tubular anatomical structure (20) and stapling head assembly (300) is positioned in another tubular anatomical structure (40). In versions where tubular anatomical structures (20, 40) comprise sections of a patient's colon, stapling head assembly (300) may be inserted via the patient's rectum. It should also be understood that the procedure depicted in FIGS. 21A-21E is an open surgical procedure, though the procedure may instead be performed laparoscopically. Various suitable ways in which instrument (10) may be used to form an anastomosis (70) in a laparoscopic procedure will be apparent to those of ordinary skill in the art in view of the teachings herein.

As shown in FIG. 21A, anvil (400) is positioned in tubular anatomical structure (20) such that shank (420) protrudes from the open severed end (22) of tubular anatomical structure (20). A purse-string suture (30) is provided about a mid-region of shank (420) to generally secure the position of anvil (400) in tubular anatomical structure (20). Similarly, stapling head assembly (300) is positioned in tubular anatomical structure (40) such that trocar (330) protrudes from the open severed end (42) of tubular anatomical structure (20). A purse-string suture (50) is provided about a mid-region of shaft (332) to generally secure the position of stapling head assembly (300) in tubular anatomical structure (40).

Next, anvil (400) is secured to trocar (330) by inserting trocar (330) into bore (422) as shown in FIG. 21B. Latch members (430) engage head (334) of trocar (330), thereby providing a secure fit between anvil (400) and trocar (330). The operator then rotates knob (130) while holding casing (110) stationary via pistol grip (112). This rotation of knob (130) causes trocar (330) and anvil (400) to retract proximally (as described above with reference to FIGS. 12A-12C). As shown in FIG. 21C, this proximal retraction of trocar (330) and anvil (400) compresses the tissue of tubular anatomical structures (20, 40) between surfaces (412, 322) of anvil (400) and stapling head assembly (300). The operator observes the position of needle (526) within window (114) to determine whether the gap distance (d) between opposing surfaces (412, 322) of anvil (400) and stapling head assembly (300) is appropriate; and makes any necessary adjustments via knob (130).

Once the operator has appropriately set the gap distance (d) via knob (130), the operator actuates safety trigger (140) (as shown in FIG. 12D) to enable actuation of firing trigger (150). The operator then actuates firing trigger (150) (as shown in FIG. 12D). This causes paddle (158) to actuate the switch of a motor activation module (180), thereby activating motor to rotate cam member (700) (as shown in FIGS. 20A-20D). This rotation of cam member (700) actuates stapling head assembly (300) by driving knife member (340) and staple driver member (350) distally as shown in FIG. 21D. As knife member (340) translates distally, cutting edge (342) of knife member (340) cooperates with inner edge (416) of anvil (400), thereby shearing excess tissue that is positioned within annular recess (418) of anvil (400) and the interior of knife member (340).

As shown in FIG. 4, anvil (400) of the present example includes a breakable washer (417) within annular recess (418). This washer (417) is broken by knife member (340) when the knife member (340) completes a full distal range of motion from the position shown in FIG. 21C to the position shown in FIG. 21D. The progressively increasing radius of curvature of second surface region may provide an increasing mechanical advantage as knife member (340) reaches the end of its distal movement, thereby providing greater force by which to break the washer (417). Of course, the breakable washer (417) may be omitted entirely in some versions. In versions where washer (417) is included, it should be understood that washer (417) may also serve as a cutting board for knife member (340) to assist in cutting of tissue. Such a cutting technique may be employed in addition to or in lieu of the above-noted shearing action between inner edge (416) and knife member (340).

As staple driver member (350) translates distally from the position shown in FIG. 21C to the position shown in FIG. 21D, staple driver member (350) drives staples (90) through the tissue of tubular anatomical structures (20, 40) and into staple forming pockets (414) of anvil (400). Staple forming pockets (414) deform the driven staples (90) into a "B" shape as is known in the art. The formed staples (90) thus secure the ends of tissue together.

Figure 21D:
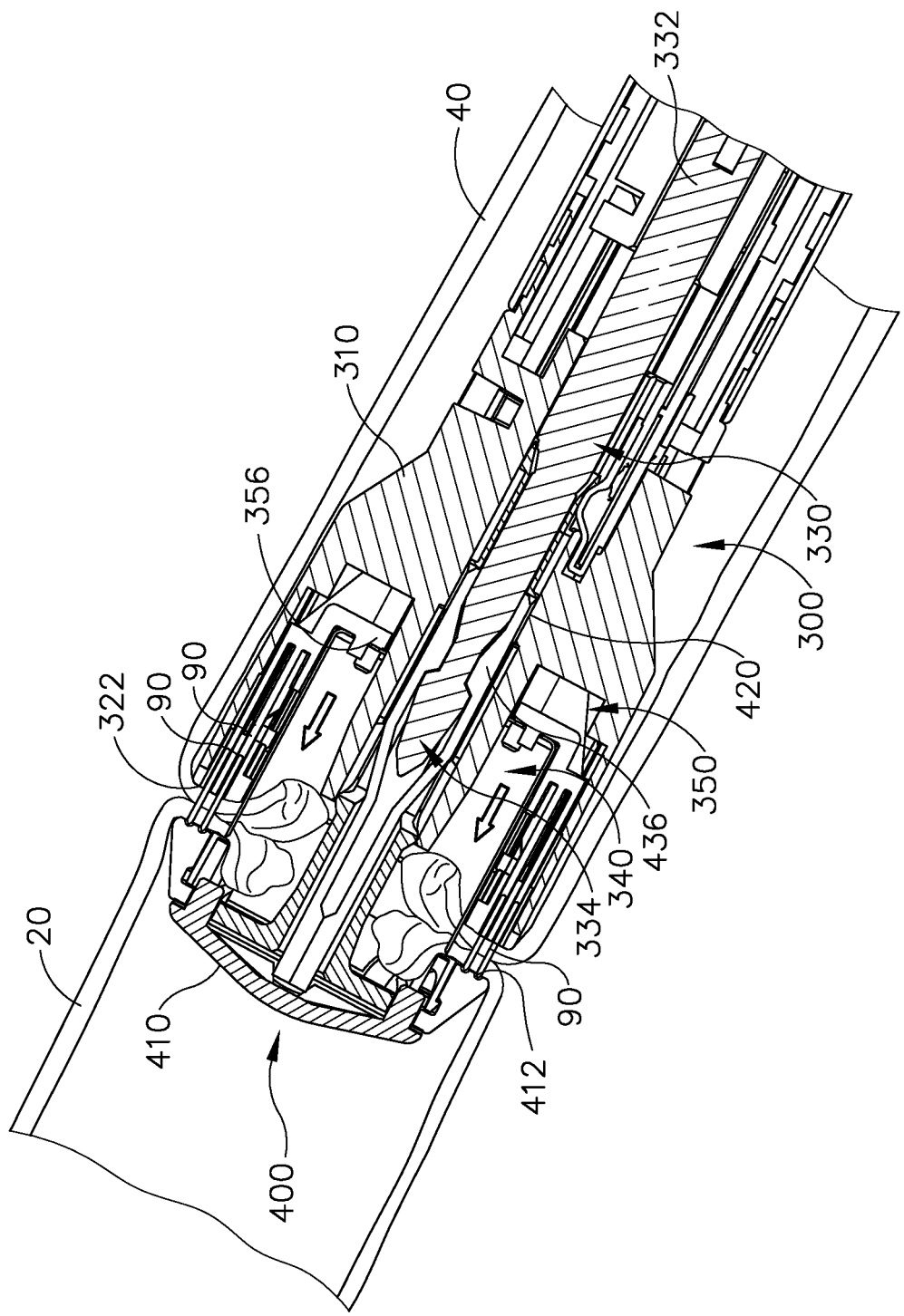
FIG. 21D depicts a cross-sectional side view of the anvil of FIG. 3 positioned within the first section of the digestive tract and the stapling head assembly of FIG. 6 positioned in the second section of the digestive tract, with the stapling head assembly actuated to sever and staple the clamped tissue.
Figure 21E:
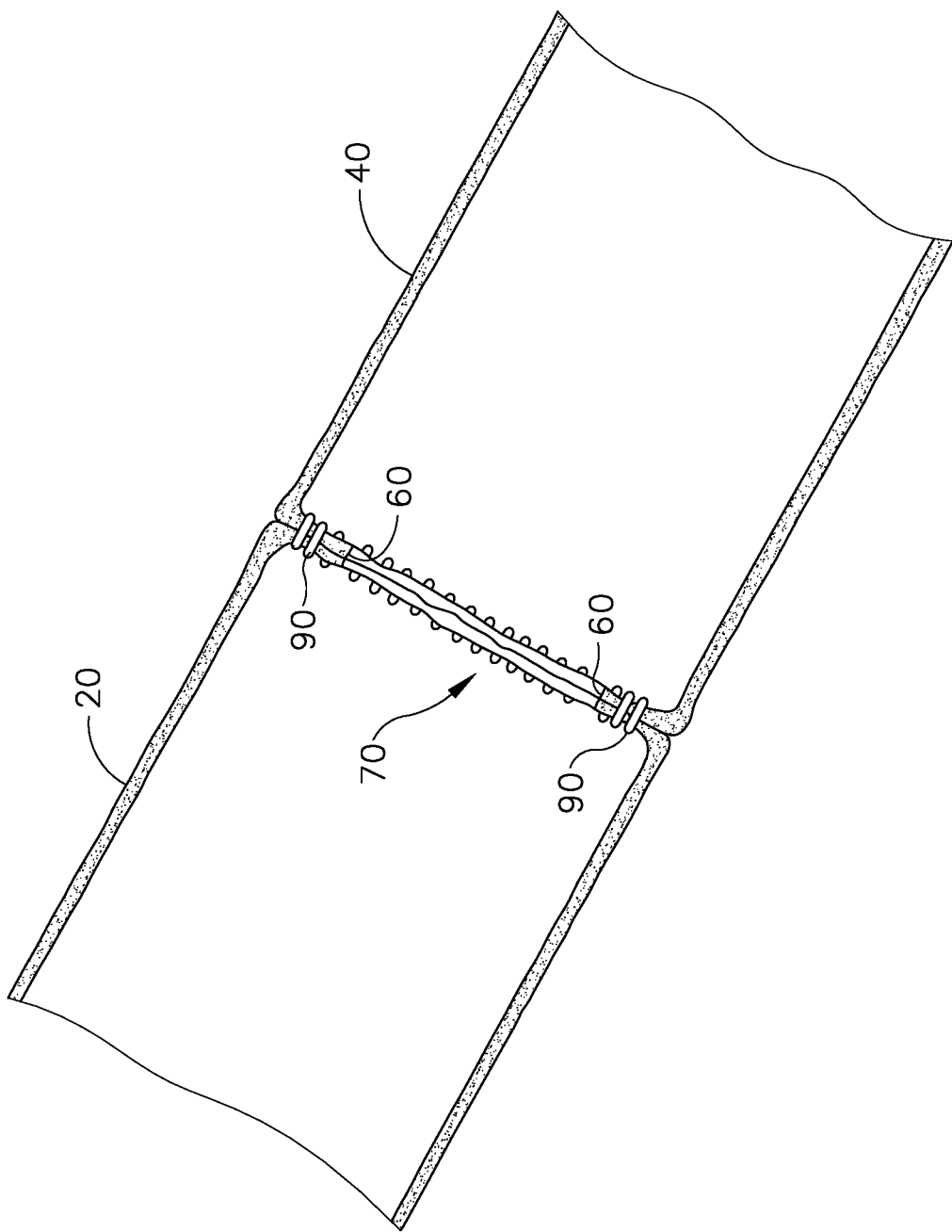
FIG. 21E depicts a cross-sectional side view of the first and second sections of the digestive tract of FIG. 21A joined together at an end-to-end anastomosis.

After the operator has actuated stapling head assembly (300) as shown in FIG. 21D, the operator rotates knob (130) to drive anvil (400) distally away from stapling head assembly (300), increasing the gap distance (d) to facilitate release of the tissue between surfaces (412, 322). The operator then removes instrument (10) from the patient, with anvil (400) still secured to trocar (330). Referring back to the example where the tubular anatomical structures (20, 40) comprise sections of a patient's colon, instrument (10) may be removed via the patient's rectum. With instrument (10) is removed, the tubular anatomical structures (20, 40) are left secured together by two annular arrays of staples (90) at an anastomosis (70) as shown in FIG. 21E. The inner diameter of the anastomosis (70) is defined by the severed edge (60) left by knife member (340).

II. Exemplary Methods for Resetting Instrument for Subsequent Firings

In some instances, it may be desirable to enable resetting of instrument (10) after firing. For example, it may be desirable to fire a single instrument (10) multiple times in a testing or quality control setting. As another merely illustrative example, it may be desirable to fire a single instrument (10) multiple times to demonstrate operation of instrument (10) in the context of a training exercise. In other situations, after instrument (10) has been used in a procedure, it may be desirable to reset instrument (10) before, during, or after instrument (10) is cleaned, sterilized, and/or otherwise reprocessed for subsequent re-use. The following examples provide techniques by which an already fired instrument (10) may be re-set for subsequent firing.

A. Exemplary Powered Reset of Manual Instrument Through Reversed Motor Rotation

Figure 22:
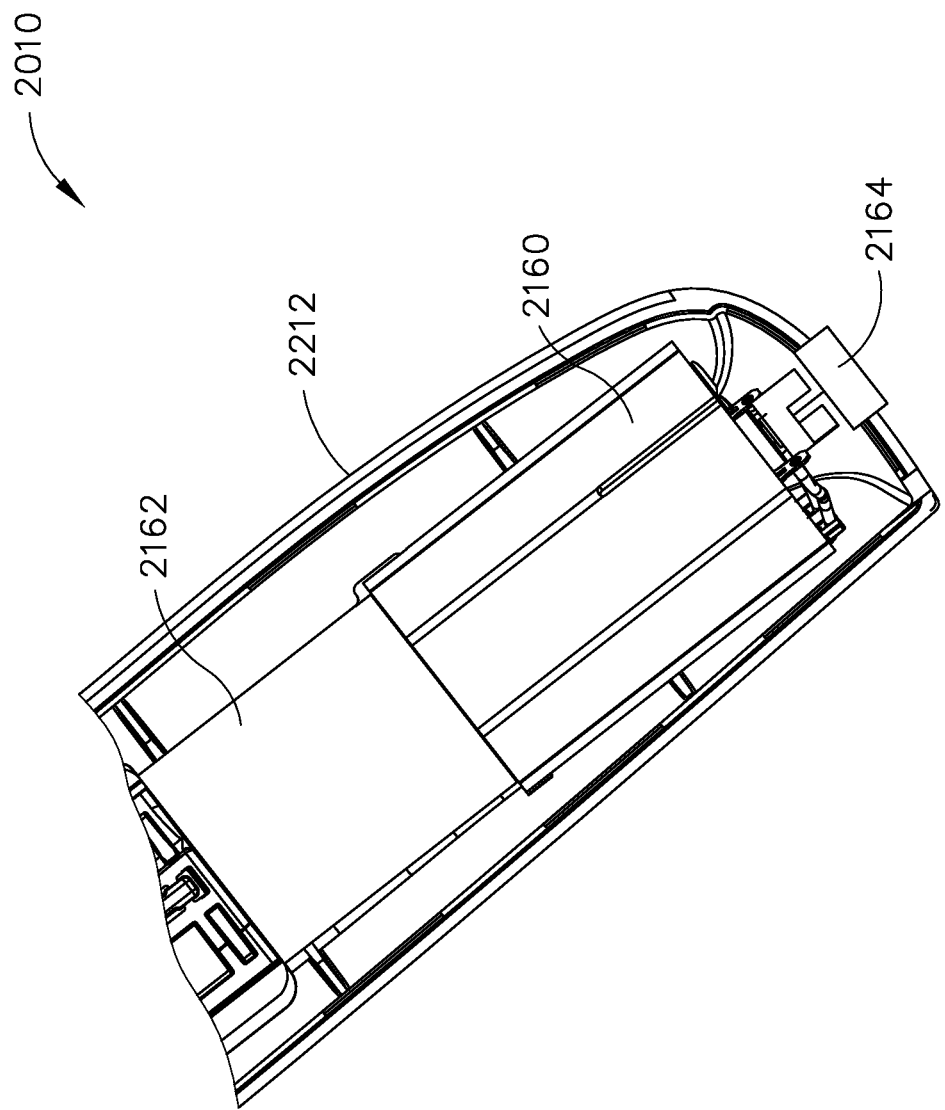
FIG. 22 depicts a detailed side view of a portion of an exemplary alternative circular stapler, shown with a portion of the body removed to show internal components.

FIG. 22 shows a pistol grip (2212) of an exemplary alternative instrument (2010), with a portion of the casing removed to show internal components. Instrument (2010) is configured to operate substantially similarly to instrument (10). Therefore, identical or substantially similar components are marked with the same reference numerals, without further discussion. It should be understood that any components and operabilities of instrument (2010) that are not described explicitly below may be the same as the components and operabilities of instrument (10) described above. Instrument (2010) includes a motor (2160) may be activated like motor (160) described above, such as by actuation of a firing trigger (not shown) that is configured to operate substantially similarly to firing trigger (150) of instrument (10). Moreover, instrument (2010) of the present example includes a safety trigger that is configured and operable like safety trigger (140) discussed above. Instrument (2010) also includes other features of the trigger lockout assembly discussed above and shown best in FIGS. 9-12E.

Instrument (2010) is different than instrument (10) in that instrument (2010) includes a switch (2164) that is in communication with motor (2160). Switch (2164) is operable to reverse the polarity of motor (2160) when switch (2164) is actuated. Thus, it will be understood that actuating switch (2164) changes the direction of rotation of motor (2160), gear box (2162), cam (700), and bushing (701), when motor (2160) is activated by actuation of a firing trigger, such as firing trigger (140) discussed above. Moreover, in order to allow for re-activation of motor (2160) after an actuation stroke of stapling head assembly (300) has been completed, instrument (2010) in some examples does not include a motor stop module, power sink, etc., or other features that prevent subsequent activation of motor (2160) once an actuation stroke of stapling head assembly (300) has been completed. In other examples, instrument (2010) may include such features that prevent re-activation of motor (2160), but such features may be configured to be disabled (i.e., such that they cannot prevent re-activation of motor (2160)).

In the present example, switch (2164) is located at the bottom of pistol grip (2212). In some versions, switch (2164) is exposed such that switch (2164) is accessible without having to disassemble instrument (2010). In some other versions, switch (2164) is positioned within pistol grip (2212) or elsewhere within instrument (2010) such that at least a portion of instrument (2010) must be disassembled in order to access switch (2164). As yet another merely illustrative example, switch (2164) may be recessed within pistol grip (2212) such that switch (2164) may be accessed with a tool inserted through a small opening in pistol grip (2212); yet such that switch (2164) is not conspicuous or easily accessible to the casual operator of instrument (2010). Other suitable ways in which switch (2164) may be positioned and accessible will be apparent to those of ordinary skill in the art in view of the teachings herein. Similarly, various suitable forms that switch (2164) may take will be apparent to those of ordinary skill in the art in view of the teachings herein.

Figure 23:
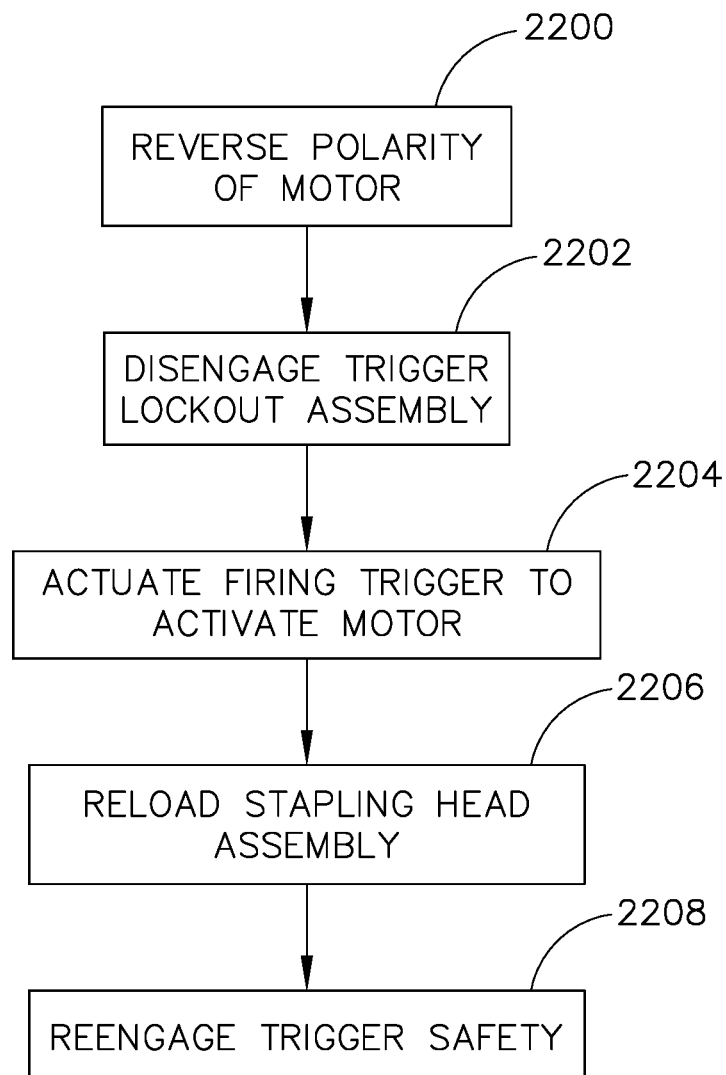
FIG. 23 depicts a flowchart showing steps of an exemplary method of resetting the circular stapler of FIG. 1 or FIG. 22.

FIG. 23 shows a first example of a method of resetting instrument (10, 2010) after firing, such as after an actuation stroke of stapling head assembly (300) of instrument (10, 2010). As shown, the method includes the step of reversing the polarity of motor (160, 2160) (block 2200). In some versions, reversing the polarity includes actuating switch (2164) of instrument (2010), thus reversing the polarity of motor (2160) as discussed above. Other suitable ways in which the polarity of motor (160, 2160) may be reversed will be apparent to those of ordinary skill in the art in view of the teachings herein. The method further includes the step of disengaging trigger lockout assembly (block 2202) as discussed above (e.g., by actuating safety trigger (140)) to allow for firing of trigger (150) and thus activation of motor (160, 2160). Once the trigger lockout assembly is disengaged, the operator may actuate firing trigger (140) to activate motor (160, 2160) (block 2204). Since the polarity of motor (160, 2160) is reversed at this stage, it should be understood that motor (160, 2160) and the associated drive components will move in a direction that is opposite to the direction of motion described above in the context of firing stapling head assembly (300).

FIGS. 25A-25D schematically depict the interaction between cam member (700), features of cam follower (600), and features of rocker member (800) as cam member (700) rotates in response to activation of motor (160, 2160) (block 2204) when the polarity of motor (160, 2160) is reversed. It should be understood that the rotation of cam member (700) throughout the stages shown in FIGS. 25A-25D is driven by motor (160) and gearbox (162). It should be further understood that the interaction between cam member (700), cam follower (600), and features of rocker member (800) occurs essentially in the opposite manner as shown in FIGS. 20A-20D and as described above. Particularly, cam (700) in FIG. 25A is in the same position relative to cam follower (600) and rocker member (800) shown in FIG. 20D; in FIG. 25B is in the same position relative to cam follower (600) and rocker member (800) as shown in FIG. 20C; in FIG. 25C is in the same position relative to cam follower (600) and rocker member (800) as shown in FIG. 20B; and in FIG. 25D is in the same position relative to cam follower (600) and rocker member (800) as shown in FIG. 20A. Of course, as noted above, in the present example, actuation of rocker member (800) does not result in the activation of a motor stop module and/or other features that prevent subsequent uses of instrument (10, 2010). Due to the reversed polarity of motor (160, 2160), activation of motor (160, 2160) causes rotation of cam (700) in an opposite rotational direction that occurred during the prior activation of motor (160, 2160) (e.g., FIGS. 20A-20D) to thereby rotate cam (700) from the position shown in FIG. 25A to the position shown in FIG. 25D.

As motor (160, 2160) is activated at a reversed polarity, cam (700) rotates from the position shown in FIG. 25A to the position in FIG. 25B. Third surface region (716) of first cam feature (710) bears against second bearing feature (610) of cam follower (600), driving second bearing feature (610) upwardly. This causes cam follower (600) to pivot about pin (118) from the position shown in FIG. 18A toward the position shown in FIG. 18B. As cam member (700) is rotated further to the position shown in FIG. 25C, second surface region (714) bears against bearing member (610), such that cam follower (60)) reaches the position shown in FIG. 18B. Cam follower (600) thus drives knife member (340) and staple driver member (350) distally via drive bracket (250) and stapling head assembly driver (240), transitioning stapling head assembly (300) back to the actuated position at the stage shown in FIG. 25C.

As cam (700) rotates further, first bearing feature (604) of cam follower (600) eventually reaches first surface region (712) of cam (700). Second surface region (724) of second cam feature (720) engages second bearing feature (610) of cam follower (600). This causes cam follower (600) to pivot about pin (118) back from the position shown in FIG. 18B toward the position shown in FIG. 18A. Cam follower (600) thus drives knife member (340) and staple driver member (350) proximally via drive bracket (250) and stapling head assembly driver (240). Therefore, first bearing feature (604) of cam follower (600) is again positioned on first surface region (712) and bearing member (610) or rocker member (800) is adjacent to second surface region (734) of third cam feature (730). Also at this stage, knife member (340) and staple driver member (350) are in proximal positions, such that stapling head assembly (300) is returned to a non-actuated state. In some versions, a resilient member (e.g., a coil spring engaged with linearly translating components of the drive assembly such as stapling head assembly driver (240) and/or drive bracket (250); and/or a torsion spring engaged with cam follower (600); etc.) provides a bias to assist in returning cam follower (600) from the position shown in FIG. 25C and FIG. 18B to the position shown in FIG. 25D and FIG. 18A.

It should be understood from the foregoing that rotating cam (700) in an opposite manner of that shown in FIGS. 20A-20D, as shown in FIGS. 25A-D, results in resetting of instrument (10, 2010). With instrument (10, 2010) reset in this fashion, stapling head assembly (300) is in a non-actuated state; and cam (700) and cam follower (600) are in a pre-firing state. Returning back to FIG. 24, at this stage the operator may then reload stapling head assembly (300) with staples (90) (block 2206), and reengage the trigger lockout assembly (block 2208) to prevent undesired firing of instrument (10, 2010) until instrument (10, 2010) is in a state and position where it is ready to be intentionally fired.

B. Exemplary Manual Reset of Instrument

Figure 24:
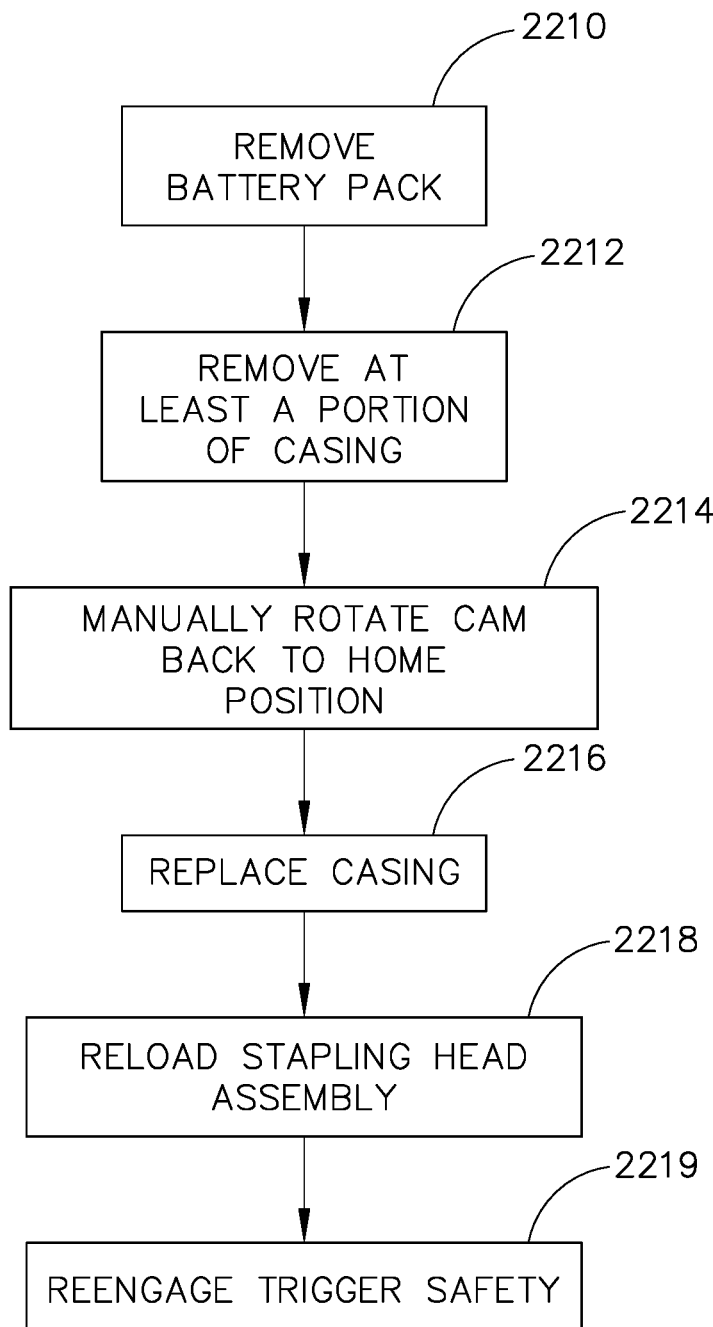
FIG. 24 depicts a flowchart showing steps of an exemplary alternative method of resetting the circular stapler of FIG. 1 or FIG. 22.

In addition to or in lieu of the method described above, an operator may reset instrument (10, 2010) for subsequent firings without activating motor (160, 2160) at all. For instance, FIG. 24 shows another exemplary method of resetting instrument (10, 2010). In this example, the operator may remove battery pack (e.g., battery pack (120)) (block 2210) and remove at least a portion of casing (110) to expose certain internal components of instrument (10, 2010), such as cam (700) (block 2212). Once cam (700) is exposed, the operator may manually rotate cam (700) from the position shown in FIG. 25A (which may be referred to herein as the "fired position") to the position shown in FIG. 25D (which may be referred to herein as the "home position") (block 2214). The user may manually rotate cam (700) by hand or by some sort of tool or device, such as a wrench, screwdriver, or other tool that is configured to provide a rotational force on cam (700). Moreover, cam (700) may include features to enable the use of such tools or devices. Various suitable forms that such features and tools may take will be apparent to those of ordinary skill in the art in view of the teachings herein.

It will be understood that when cam (700) is manually rotated in reverse, the interaction between cam (700), cam follower (600), and rocker member (800), as well as stapling head assembly (300), will be substantially identical to the interaction between cam (700) and such components with motor-driven reversed rotation of cam (700) as described with respect to FIG. 23. Manually rotating cam (700) in an opposite manner of that shown in FIGS. 20A-20D, thus provides the movement shown in FIGS. 25A-25D, resulting in resetting of instrument (10, 2010) as described above. It will be further understood that the operator must subject cam (700) to a sufficient level of rotational force that overcomes the resistance from other components such as cam follower (600), rocker member (800), and stapling head assembly (300), etc.), in order to rotate cam (700) in reverse. Once cam (700) has been manually rotated to the position shown in FIG. 25D, the operator then replaces casing (110) (block 2216), reloads stapling head assembly (300) with staples (90) (block 2218), and reengages the trigger lockout assembly (block 2219) to prevent undesired firing of instrument (10, 2010) until instrument (10, 2010) is in a state and position where it is ready to be intentionally fired.

Figure 26:
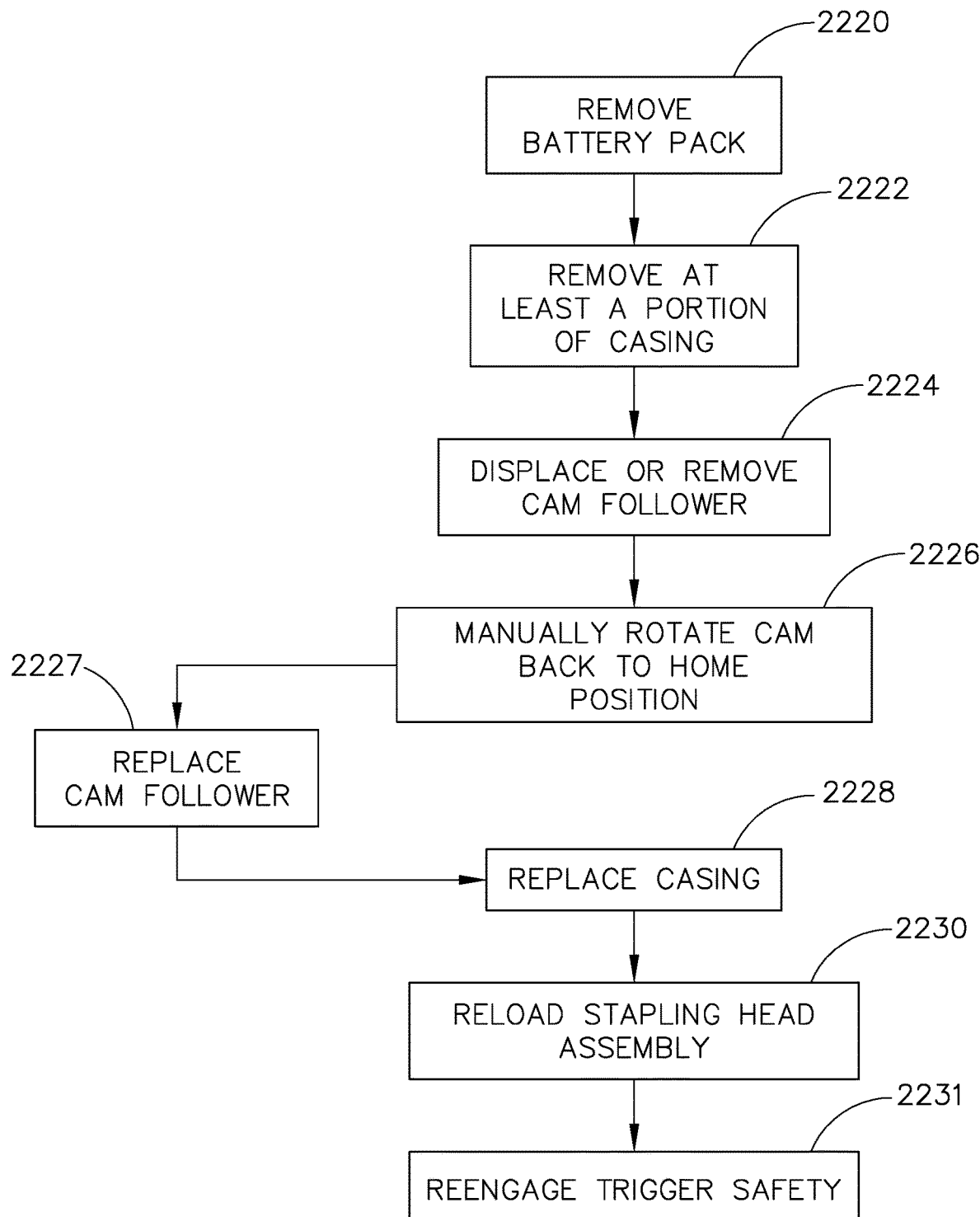
FIG. 26 depicts a flowchart showing steps of another exemplary alternative method of resetting the circular stapler of FIG. 1 or FIG. 22.

FIG. 26 shows another exemplary method of resetting instrument (10, 2010) for subsequent firings without activating motor (160, 2160). The method shown in FIG. 26 may be performed in addition to or in lieu of other methods for resetting instrument (10, 2010). As shown, the operator removes battery pack (120) (block 2220) and removes at least a portion of casing (110) (block 2222) to expose certain internal components of instrument (10, 2010), such as cam (700). Once cam (700) is exposed, the operator displaces or removes cam follower (600) (block 2224) such that cam (700) may be more easily moved from the position shown in FIGS. 20D and 25A to the position shown in FIGS. 20A and 25D (block 2226) without substantially interacting with cam follower (600), stapling head assembly (300), and other components. The operator may manually rotate cam (700) by hand or by some sort of tool or device, such as a wrench, screwdriver, or other tool that is configured to provide a rotational force on cam (700). Moreover, cam (700) may include features to enable the use of such tools or devices.

Once cam (700) has been manually rotated from the fired position back to the home position, the operator may replace cam follower (600) (block 2227) such that cam follower (600) is re-engaged with cam (700). The operator then replaces casing (110) (block 2228), reloads stapling head assembly (300) with staples (90) (block 2230), and reengages the trigger lockout assembly (block 2231) to prevent undesired firing of instrument (10, 2010) until instrument (10, 2010) is in a state and position where it is ready to be intentionally fired.

Figure 27:
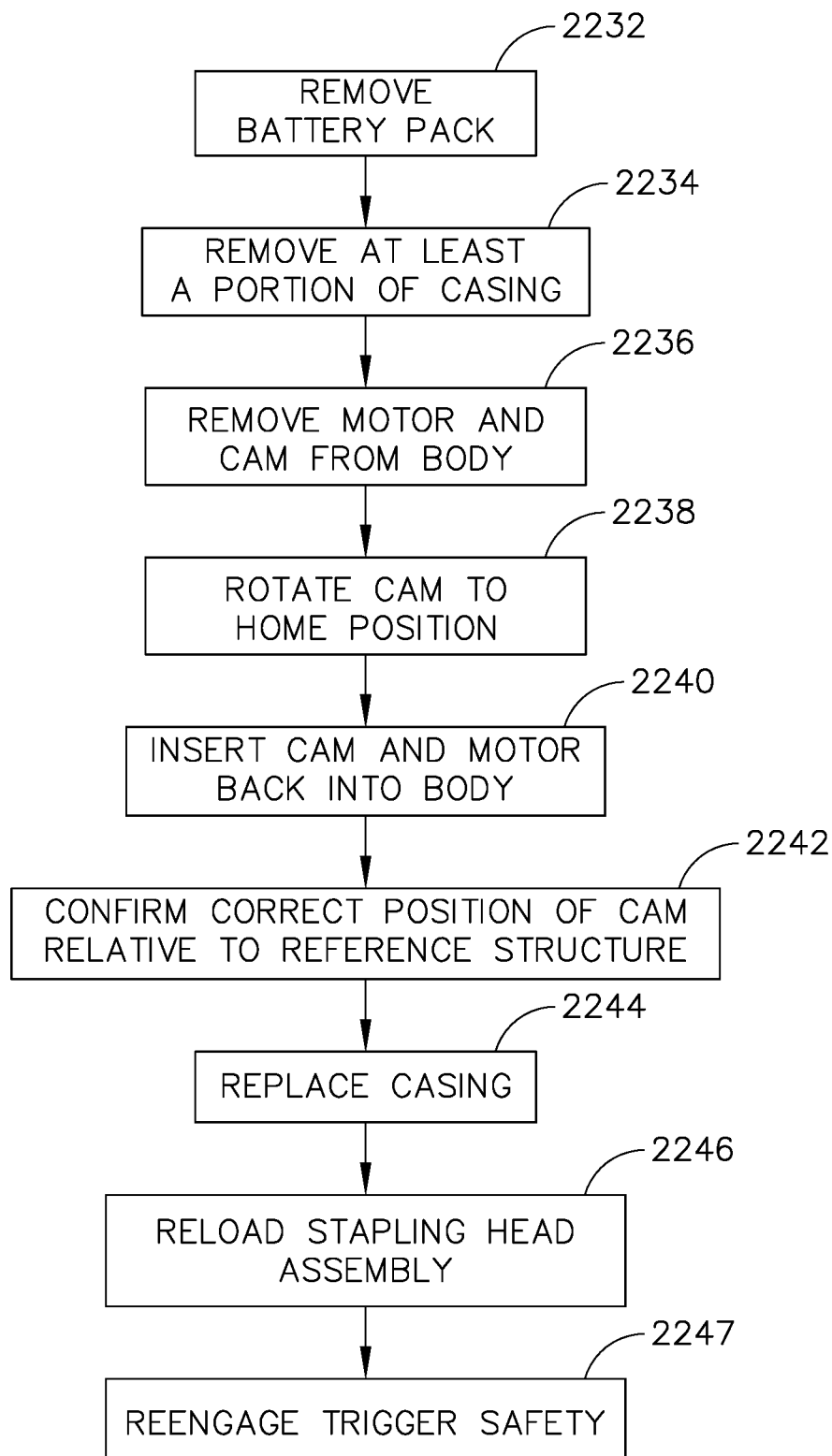
FIG. 27 depicts a flowchart showing steps of another exemplary alternative method of resetting the circular stapler of FIG. 1 or FIG. 22.

FIG. 27 shows another exemplary method of resetting instrument (10, 2010) for subsequent firings without activating motor (160, 2160). The method shown in FIG. 26 may be performed in addition to or in lieu of other methods for resetting a surgical instrument. As shown, the operator removes battery pack (120) (block 2232) and removes at least a portion of casing (110) (block 2234) to expose certain internal components of instrument (10, 2010), such as cam (700). The operator then removes motor (160, 2160), gear box (162, 2162), and cam (700) from handle assembly (200) (block 2236). Once these components are removed from handle assembly (200), the operator rotates cam (700) back to the home position shown in FIGS. 20A and 25D (block 2238). In this regard, motor (160, 2160), gear box (162), and/or cam (700) may include a marking that is angularly positioned to indicate the home position of cam (700) relative to the motor (160, 2160) and/or gear box (162).

Once cam (700) has been manually repositioned to the home position, the operator then inserts cam (700), motor (160, 2160), and gear box (162) back into handle assembly (200) (block 2240) and confirms the correct position of cam (700) relative to a reference structure (block 2242). For instance, the operator may confirm the correct position of third cam feature (730) relative to bearing member (804). If the position of cam (700) is not proper (e.g., as shown in FIGS. 20A and 25D), the operator may further adjust the position of cam (700). Once the proper positioning of cam (700) has been confirmed, the operator replaces casing (110) (block 2244), reloads stapling head assembly (300) with staples (90) (block 2246), and reengages the trigger lockout assembly (block 2247) to prevent undesired firing of instrument (10, 2010) until instrument (10, 2010) is in a state and position where it is ready to be intentionally fired. In some alternative examples, the operator may remove cam (700) and not remove motor (160, 2160) and/or gear box (162). The operator may then replace cam (700) relative to other structures of instrument (10, 2010), in the position shown in FIGS. 20A and 25D.

It should be understood that after any of the processes shown in FIGS. 23-24 and 26-27 are complete, instrument (10, 2010) may again be used to perform an anastomosis procedure such as the procedure shown in FIGS. 21A-21E and described above. In other words, a reset instrument (10, 2010) may be used just like a version of instrument (10, 2010) that had never been used before.

C. Exemplary Powered Reset of Manual Instrument Through Continued Motor Rotation In the examples described above, motor stop module (190) is configured to create a short circuit and thereby prevent motor (160) from further activation after paddle (806) actuates switch buttons (192) at the end of an actuation stroke (as illustrated in FIGS. 20A-20D). Some such versions may be configured and operable in accordance with at least some of the teachings of U.S. Pub. No. 2015/0083774, issued as U.S. Pat. No. 9,907,552 on Mar. 6, 2018, the disclosure of which is incorporated by reference herein. As also noted above, some such versions may allow the actuation drivetrain for stapling head assembly (300) to be returned to a home position (i.e., the state shown in FIGS. 20A and 25D) by reversing the polarity of the drive circuit to thereby cause motor (160) to rotate in the reverse direction (as illustrated in FIGS. 25A-25D).

Some alternative drive circuits may provide a different configuration and method to stop motor (160) at the end of an actuation stroke. For instance, some alternative drive circuits may provide a polarity reversal in the drive circuit (instead of providing a short circuit) at the end of an actuation stroke, to thereby brake motor (160) at the end of the actuation stroke. By way of example only, such a circuit may be constructed and operable in accordance with at least some of the teachings of U.S. Pub. No. 2017/0258471, entitled "Methods and Systems for Performing Circular Stapling," published Sep. 14, 2017, issued as U.S. Pat. No. 10,709,452 on Jul. 14, 2020, the disclosure of which is incorporated by reference herein. In versions where the polarity is automatically reversed at the end of the actuation stroke, a different technique may be warranted for returning the actuation drivetrain for stapling head assembly (300) to the home position (i.e., the state shown in FIGS. 20A and 25D).

An example of a circuit (2600) providing braking of motor (160) through polarity reversal is shown in FIGS. 29A-29H, in which motor stop module (190) has been modified to become a motor stop module (2690). Motor stop module (2690) includes switch buttons (192) just like motor stop module (190). Motor stop module (2690) may also be configured and positioned just like motor stop module (190), such that switch buttons (192) are actuated by paddle (806) at the end of an actuation stroke as shown in FIGS. 19A-19D. As described in greater detail below, switch buttons (192) are configured to provide drive circuit (2600) with a first polarity state (FIGS. 29A-29B and FIGS. 20A-20C) until switch buttons (192) are actuated by paddle (806) at the end of an actuation stroke; then with a second polarity state (FIGS. 29C-29F, FIG. 20D, and FIG. 30A) while switch buttons (192) are being actuated by paddle (806); and then with the first polarity state again (FIGS. 29G-29H and FIG. 30B) after switch buttons (192) are no longer being actuated by paddle (806).

Figure 28:
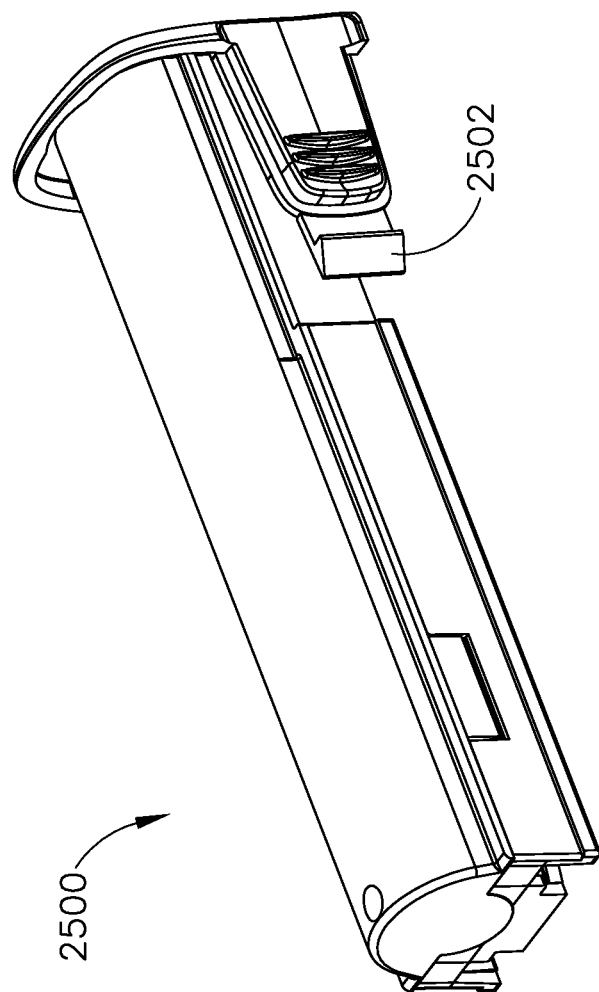
FIG. 28 depicts a perspective view of an exemplary alternative battery pack that may be used to reset the circular stapler of FIG. 1.

FIG. 28 shows an exemplary battery pack (2500) that may be used in instrument (10) after the completion of an actuation stroke, to return the actuation drivetrain for stapling head assembly (300) to the home position, when instrument includes a drive circuit like circuit (2600) shown in FIGS. 29A-29H. Battery pack (2500) is configured to fit in socket (116) just like battery pack (120). Battery pack (2500) also includes latches (2502), just like latches (122), that releasably retain battery pack (2500) in socket (116). Battery pack (2500) is different from battery pack (120) only in that battery pack (2500) is provided with a polarity that is the reverse of the polarity of battery pack (120).

FIGS. 29A-29H show circuit (2600) at various states of operation. Circuit (2600) includes motor stop module (2690), a pair of battery terminals (2620, 2622), motor (160), and firing switch (2610). Circuit (2600) also includes various transistors, diodes, LEDs, and a capacitor, among other conventional components. Various kinds of components, characteristics of such components, and arrangements of such components, that may be incorporated into circuit (2600) will be apparent to those of ordinary skill in the art in view of the teachings herein. Battery terminals (2620, 2622) of the present example are configured to couple with corresponding terminals of battery pack (120) when battery pack (120) is fully seated in socket (116); and with corresponding terminals of battery pack (2500) when battery pack (2500) is fully seated in socket (116). Motor (160) is the same motor (160) described above, such that motor (160) is operable to rotate cam member (700). Firing switch (2610) is coupled with firing trigger (150) such that paddle (158) causes firing switch (2610) to reach a closed state when trigger (150) is actuated; and such that firing switch (2610) is in an open state whenever trigger (150) is not being actuated (e.g., firing switch (2610) may return to an open state after a depressed trigger (150) has been released).

Figure 29A:
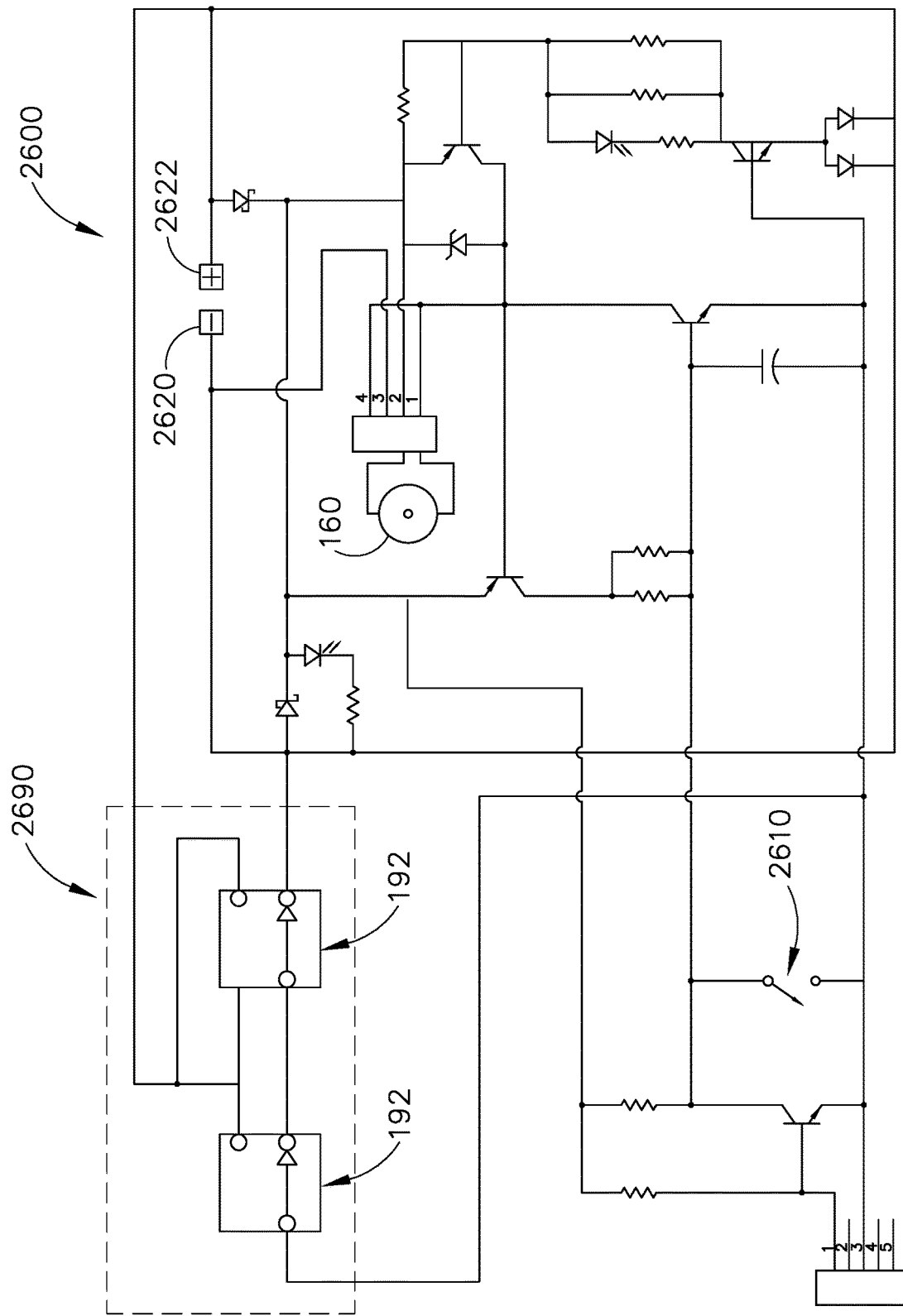
FIG. 29A depicts an exemplary control circuit that may be incorporated into the circular stapler of FIG. 1, with the battery pack of FIG. 2 inserted in the stapler, with a firing switch in an open state, and with a pair of stop switches in a first polarity state.
Figure 29B:
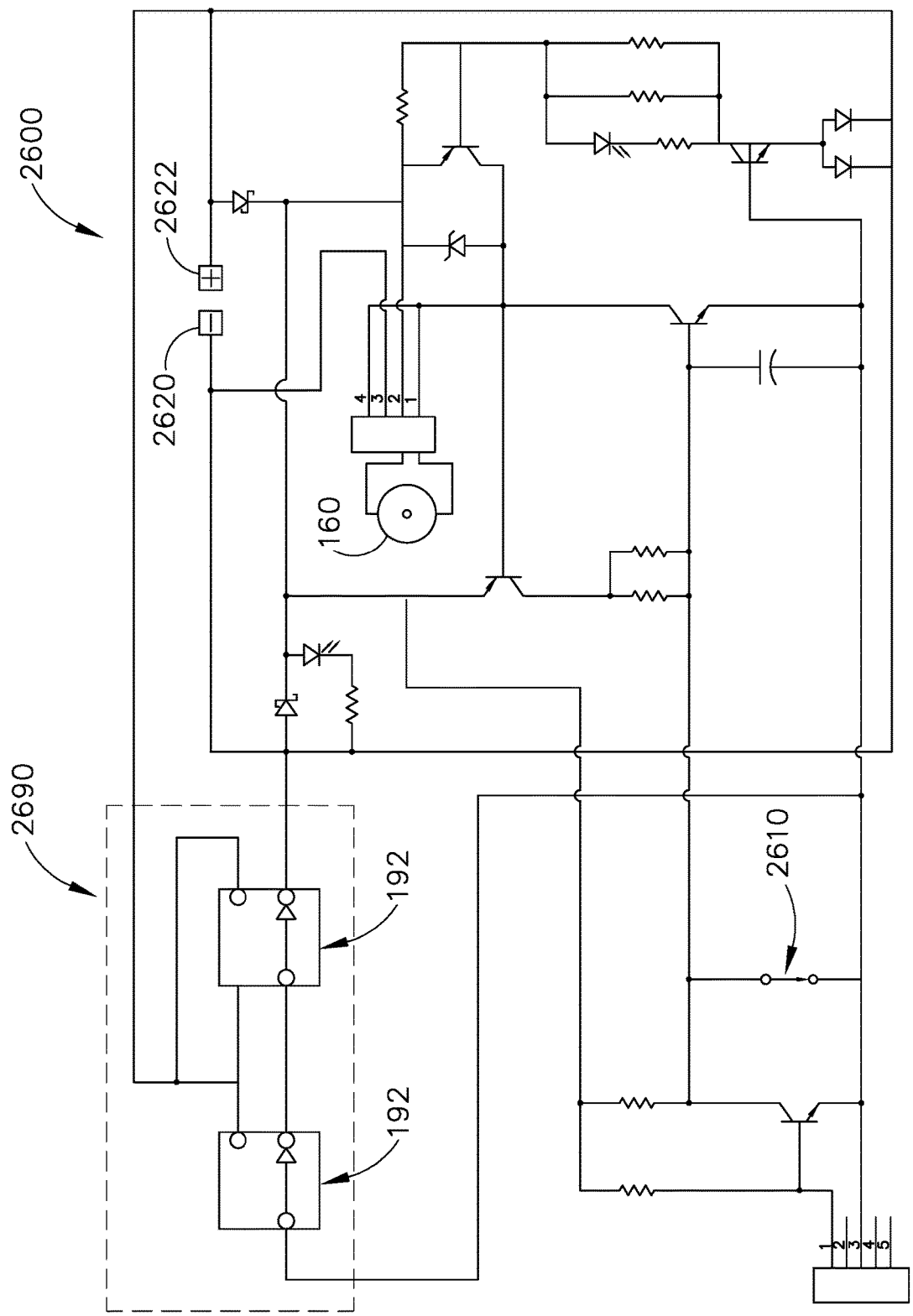
FIG. 29B depicts the control circuit of FIG. 29A, with the battery pack of FIG. 2 inserted in the stapler, with the firing switch in a closed state, and with the pair of stop switches in the first polarity state.
Figure 29C:
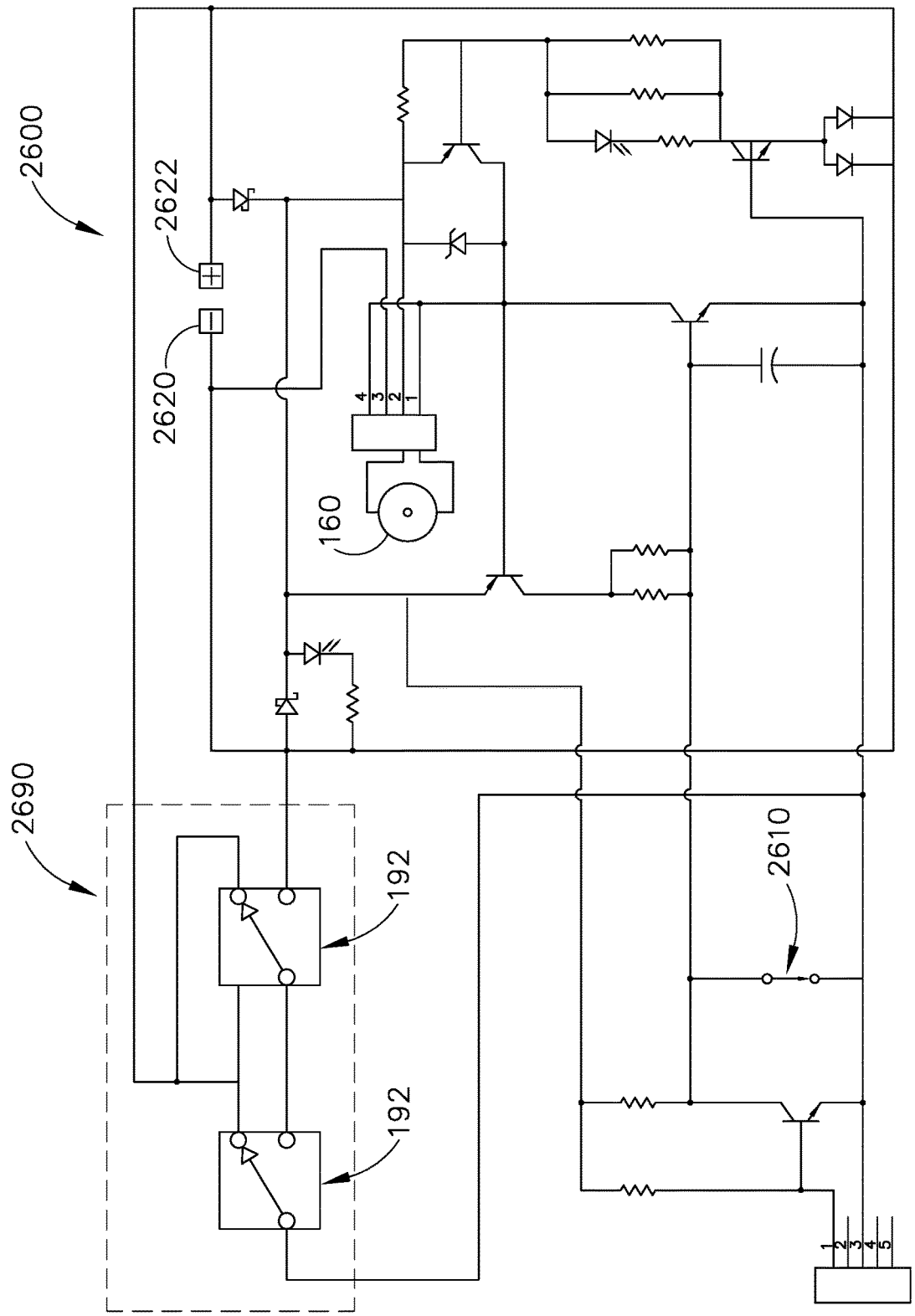
FIG. 29C depicts the control circuit of FIG. 29A, with the battery pack of FIG. 2 inserted in the stapler, with the firing switch in the closed state, and with the pair of stop switches in a second polarity state.

FIG. 29A shows circuit (2600) in a state where instrument (10) is in an initial, ready-to use state. At this stage, battery pack (120) is disposed in socket (116), cam member (700) is in the position shown in FIG. 20A, firing trigger (150) is in a non-actuated state, and motor stop module (2690) is providing a first polarity state. FIG. 29B shows circuit (2600) after the operator has actuated trigger (150), thereby transitioning firing switch (2610) from an open state to a closed state. As a result, motor (160) is activated to rotate cam member (700) in a first angular direction, such that cam member (700) rotates through the stages shown in FIGS. 20A-20C.

Figure 20D:
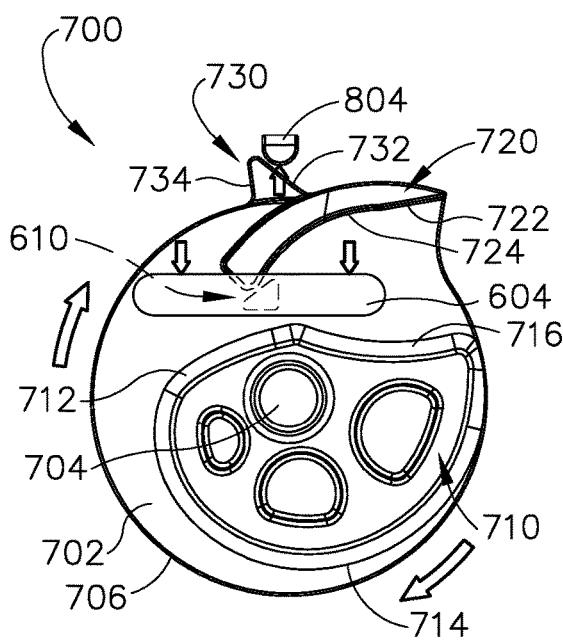
FIG. 20D depicts a schematic end view of the rotary cam of FIG. 16, the cam follower of FIG. 14, and the rocker member of FIG. 19A, with the rotary cam in a fourth angular position, the cam follower in a third pivotal position, and the rocker member in a second pivotal position.
Figure 29D:
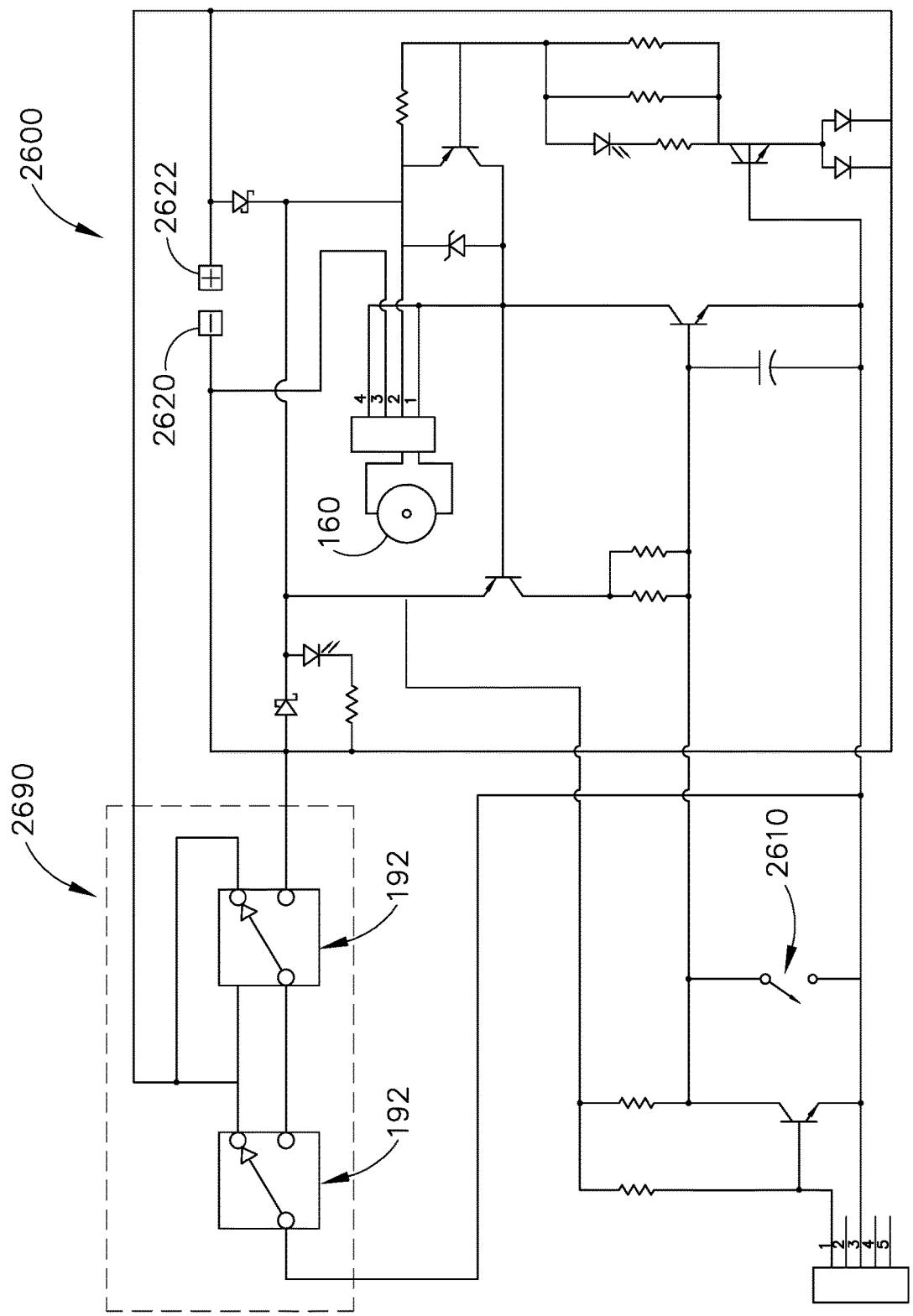
FIG. 29D depicts the control circuit of FIG. 29A, with the battery pack of FIG. 2 inserted in the stapler, with the firing switch in the open state, and with the pair of stop switches in the second polarity state.

As cam member (700) rotates through a full drive stroke, cam member (700) eventually reaches the position shown in FIG. 20D, where third cam feature (730) engages bearing member (804). As third cam feature (730) drives bearing member (804) upwardly, paddle (806) is driven to actuate switch buttons (192), thereby causing switch buttons (192) to transition to the state shown in FIG. 29C. Circuit (2600) is this transitioned to the second polarity state. Upon reaching the second polarity state, motor (160) is no longer activated, such that cam member (700) stops rotating, even if the operator continues to actuate firing trigger (150) to hold firing switch (2610) in a closed state. FIG. 29D shows circuit (2600) in a state where the operator has released firing trigger (150), thereby opening firing switch (2610), after completion of the actuation stroke.

While firing switch (2610) is shown as being in a closed state during the entire actuation stroke of cam member (700), and not returning to the open state until after the actuation stroke is completed, some versions of circuit (2600) may still complete the full actuation stroke of cam member (700) even if the operator releases firing trigger (150), thereby opening firing switch (2610), before the full actuation stroke of cam member (700) is completed. By way of example only, such functionality may be provided in accordance with at least some of the teachings of U.S. Pub. No. 2015/0083774, issued as U.S. Pat. No. 9,907,552 on Mar. 6, 2018, the disclosure of which is incorporated by reference herein.

Figure 29E:
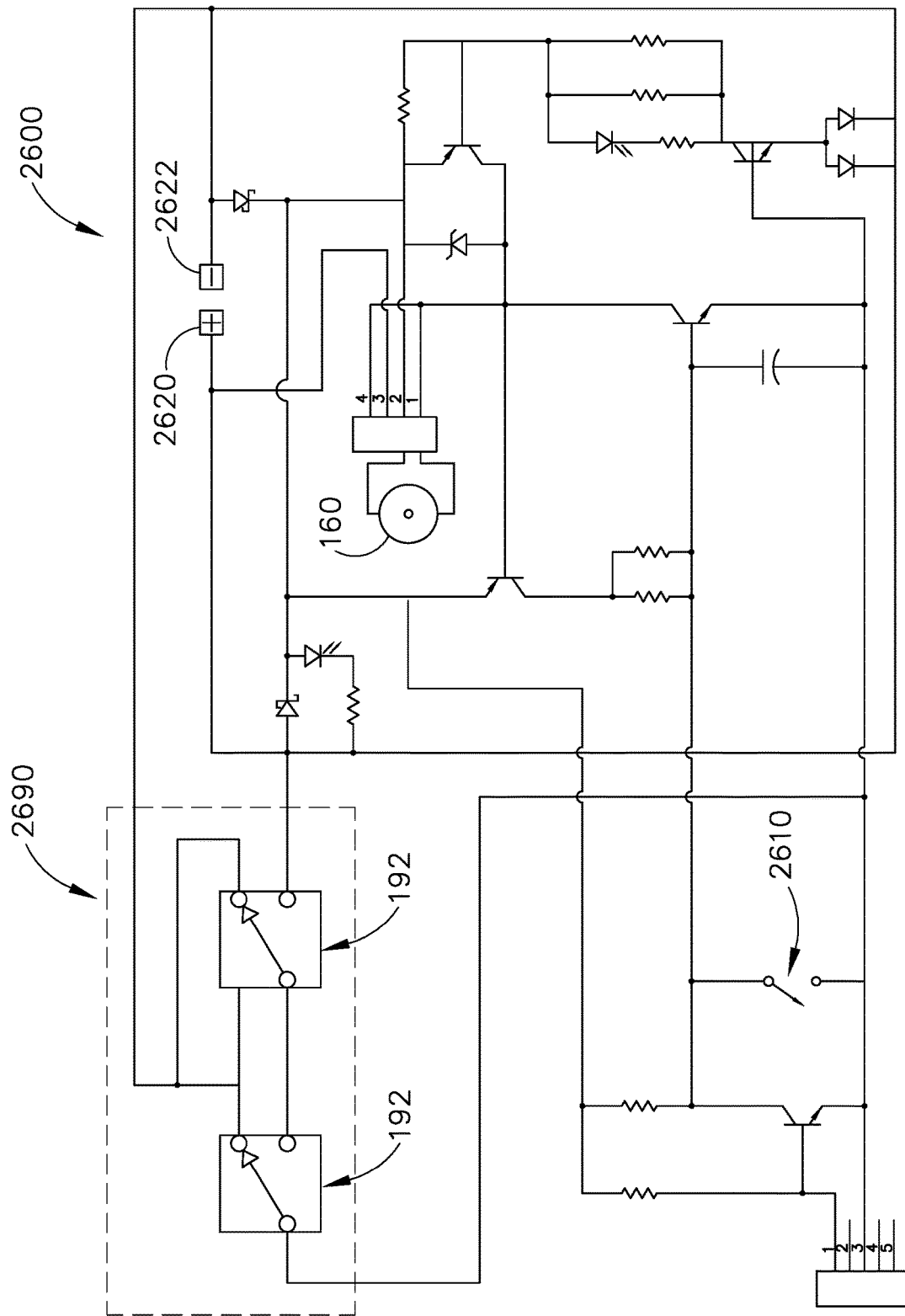
FIG. 29E depicts the control circuit of FIG. 29A, with the battery pack of FIG. 28 inserted in the stapler, with the firing switch in the open state, and with the pair of stop switches in the second polarity state.
Figure 29F:
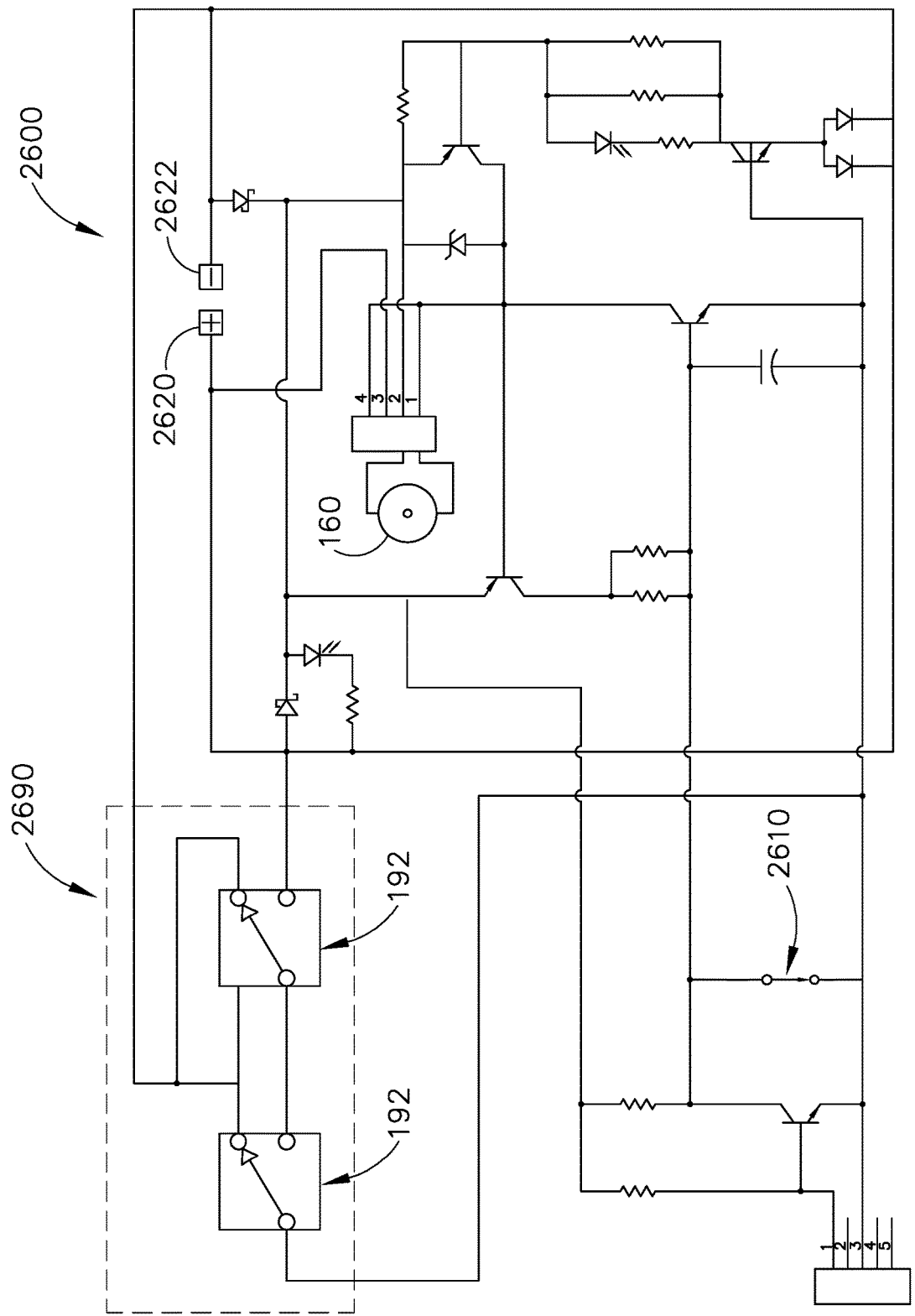
FIG. 29F depicts the control circuit of FIG. 29A, with the battery pack of FIG. 28 inserted in the stapler, with the firing switch in the closed state, and with the pair of stop switches in the second polarity state.

After reaching the state shown in FIG. 29D, the operator may wish to return the actuation assembly to the home state, to thereby allow the actuation assembly to run through another full actuation stroke (e.g. to demonstrate operation of the product in a training context, etc.). To that end, FIG. 29E shows circuit (2600) in a state where the operator has removed battery pack (120) and replaced battery pack (120) with battery pack (2500). Thus, the polarity at terminals (2620, 2622) is now reversed. With the polarity of circuit (2600) being in the second state (based on the state of switch buttons (192)), and with battery pack (2500) being inserted in socket (116), the operator may again actuate firing trigger (150) to close firing switch (2610) again, as shown in FIG. 29F. This causes motor (160) to activate again. Unlike earlier described examples where the rotation direction of cam member (700) is reversed to return to a home position, in the present example motor (160) rotates cam member (700) in the same first angular direction that was used during the actuation stroke shown in FIGS. 20A-20D.

Figure 30A:
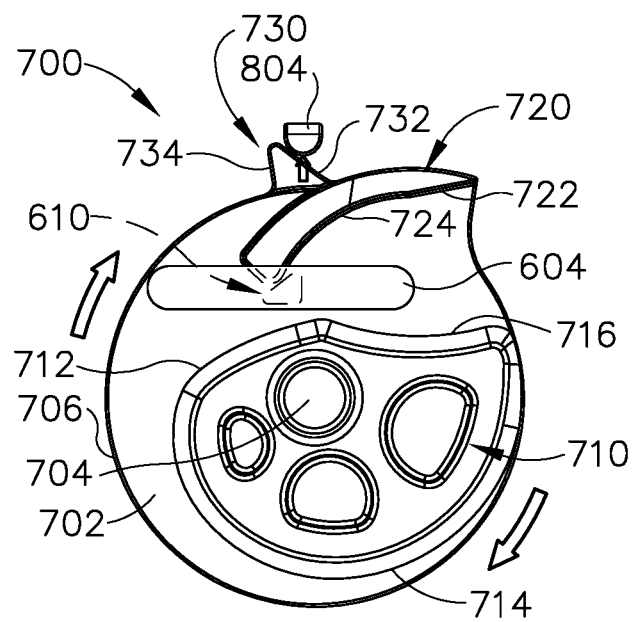
FIG. 30A depicts a schematic end view of the rotary cam of FIG. 16, the cam follower of FIG. 14, and the rocker member of FIG. 19A, with the rotary cam in the fourth angular position, the cam follower in the third pivotal position, and the rocker member in the second pivotal position.
Figure 30B:
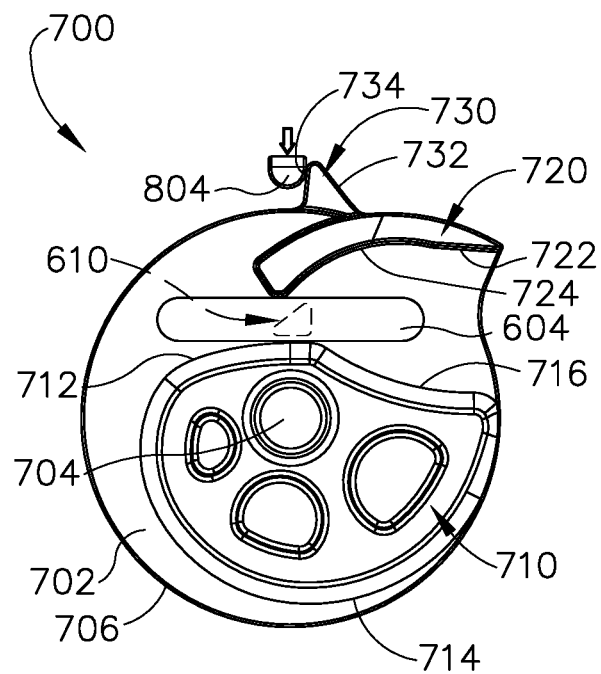
FIG. 30B depicts a schematic end view of the rotary cam of FIG. 16, the cam follower of FIG. 14, and the rocker member of FIG. 19A, with the rotary cam in the first angular position, the cam follower in the first pivotal position, and the rocker member in the first pivotal position.

FIGS. 30A-30B show cam member (700) rotating through a range of motion to transition cam member (700) from the fully actuated position (FIG. 30A) to the home position (FIG. 30B). The fully actuated position shown in FIG. 30A is the same as the fully actuated position shown in FIG. 20D. Also, the home position shown in FIG. 30B is the same as the home position shown in FIG. 20A. As cam member (700) rotates from the position shown in FIG. 30A to the position shown in FIG. 30B, bearing member (804) continues to ride along first surface region (732) of third cam feature (732) until bearing member (804) finally clears first surface region (732), such that bearing member (804) eventually snaps back down to the position shown in FIG. 30B. During this motion, bearing member (804) and/or some other portion of rocker member (800) may deform to allow bearing member (804) to ride over the peak of first surface region (732). Also during this motion, paddle (806) holds switch buttons (192) in an actuated state until bearing member (804) finally clears the peak of first surface region (732).

Figure 29G:
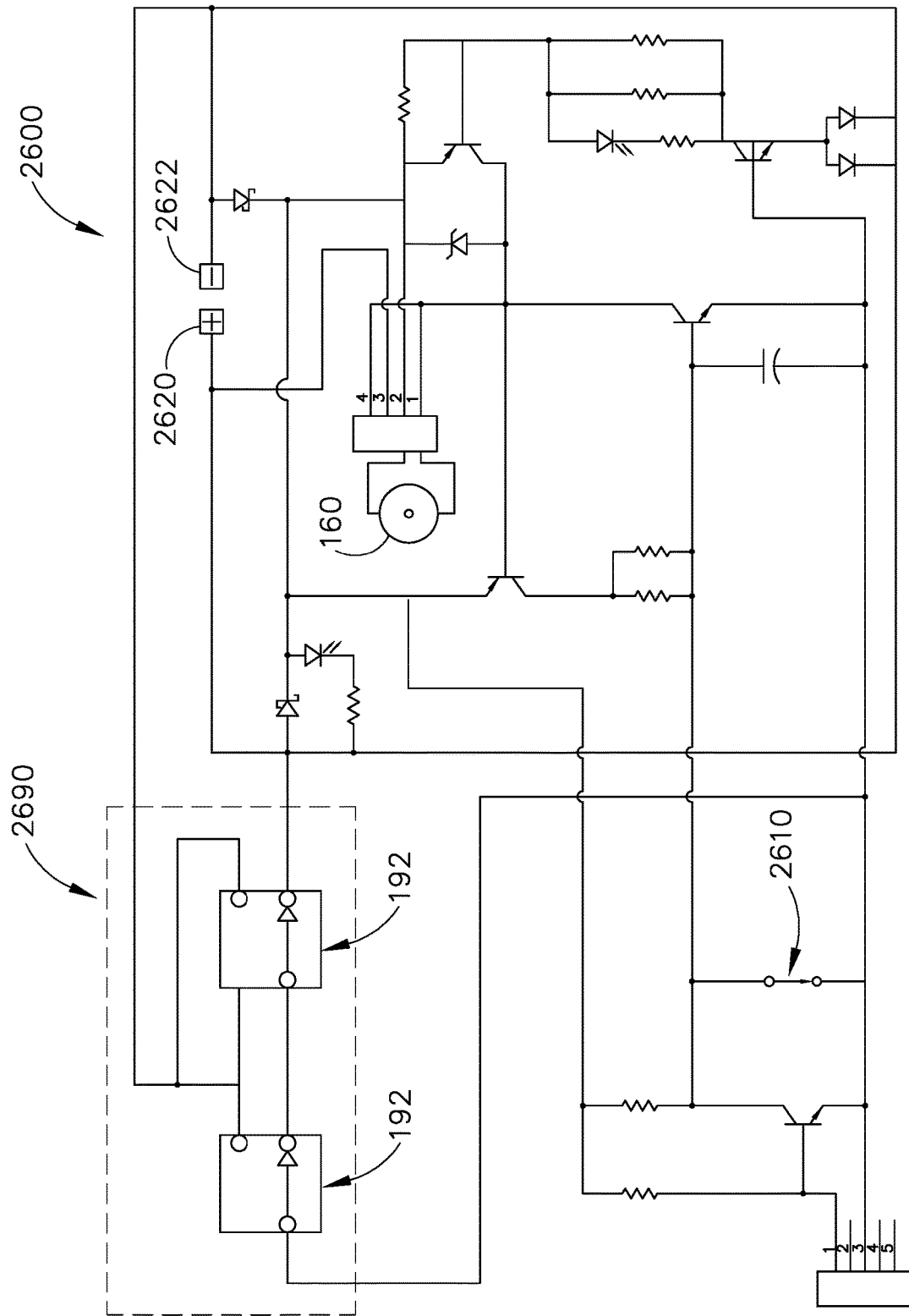
FIG. 29G depicts the control circuit of FIG. 29A, with the battery pack of FIG. 28 inserted in the stapler, with the firing switch in the closed state, and with the pair of stop switches in the first polarity state.
Figure 29H:
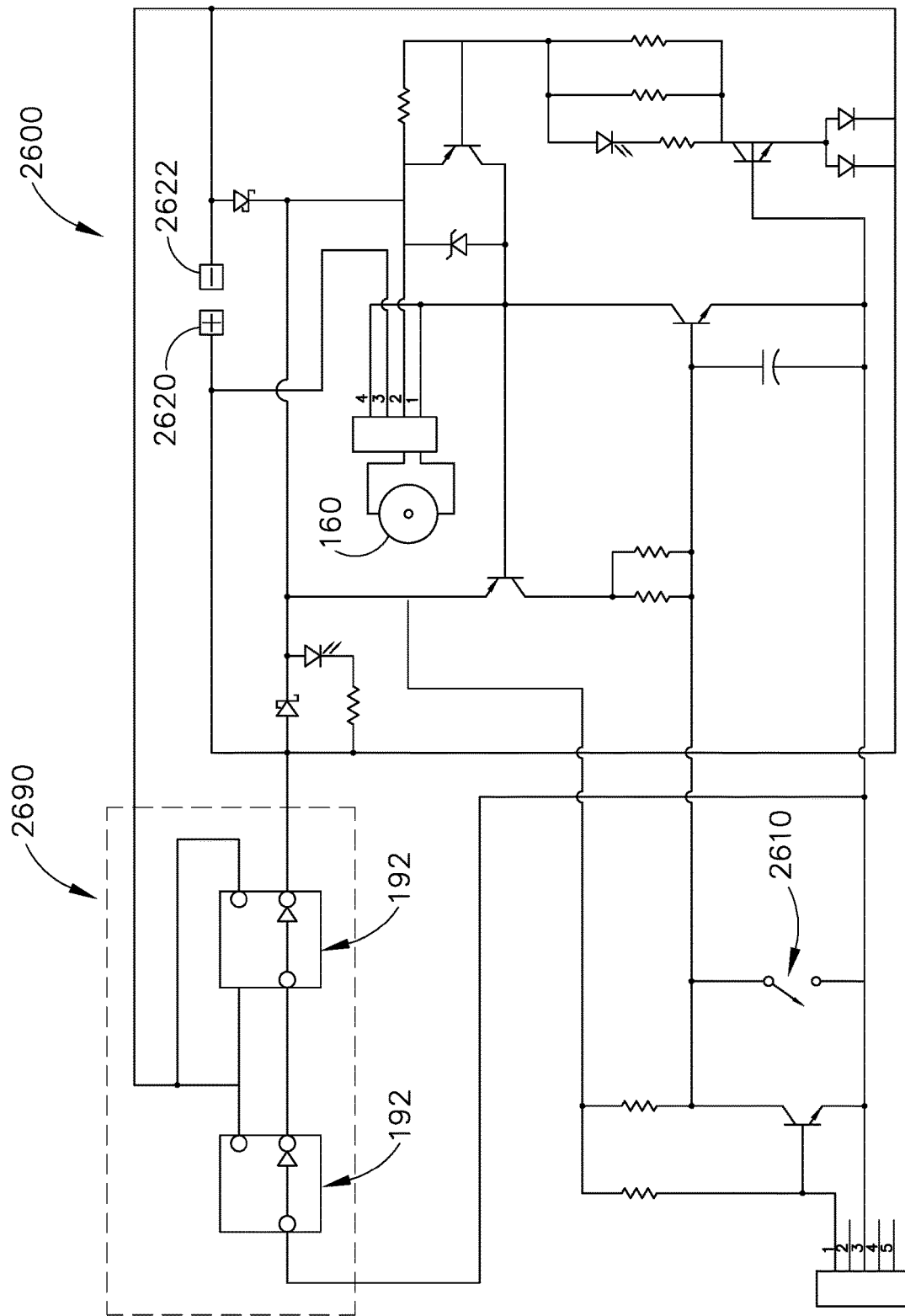
FIG. 29H depicts the control circuit of FIG. 29A, with the battery pack of FIG. 28 inserted in the stapler, with the firing switch in the open state, and with the pair of stop switches in the first polarity state.

FIG. 29F shows circuit (2600) as cam member (700) travels through the range of motion shown in FIGS. 30A-30B; and FIG. 29G shows circuit (2600) after cam bearing member (804) has cleared the peak of first surface region (732) such that paddle (806) is no longer holding buttons (192) in an actuated state. As shown in FIG. 29G, switch buttons (192) thereby return circuit (2600) to the first polarity state. Upon this transition back to the first polarity state, motor (160) is no longer activated. The operator then releases firing trigger (150), thereby resulting in firing switch (2610) returning to the open state as shown in FIG. 29H. As noted above, some versions of circuit (2600) may include a latching feature that maintains activation of motor (160) until switch buttons (192) return circuit (2600) to the first polarity state, even if the operator releases firing trigger (150) and thereby opens firing switch (2610) before cam member (700) completes the full range of travel depicted in FIGS. 30A-30B.

After reaching the state shown in FIG. 29H, cam member (700) is returned to the home position (FIGS. 20A and 30B), circuit (2600) is back in the first polarity state (due to the states of switch buttons (192)), and firing switch (2610) is back in the open state. The operator may then remove battery pack (2500) from socket (116) and insert battery pack (120) in socket (116), thereby returning circuit (2600) back to the sate shown in FIG. 29A. The operator may then repeat the sequence described above with reference to FIGS. 29A-29H as many times as desired.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

A method for resetting an apparatus configured for stapling tissue, the apparatus comprising: (a) a stapling head assembly, wherein the stapling head assembly comprises: (i) an annularly arranged array of staples, and (ii) a knife with an annular cutting edge that is configured to cut tissue; (b) a shaft assembly coupled to the stapling head assembly; (c) a body coupled to the shaft assembly, wherein the body comprises: (i) a motor, and (ii) a cam member configured to rotate in response to activation of the motor, wherein the cam member is rotatable in a first direction from a home position to a fired position to actuate the stapling head assembly to thereby drive the staples and the knife through tissue; (d) a circuit in electrical communication with the motor; wherein the method comprises: (a) providing an apparatus including the cam member in the fired position; (b) changing the polarity of the circuit; and (c) activating the motor such that the cam member rotates from the fired position to the home position.

EXAMPLE 2

The method of Example 1, wherein the cam member rotates less than 360 degrees when rotating between the home position and fired position.

EXAMPLE 3

The method of any one or more of Examples 1 through 2, wherein the cam member rotates through a first range of motion to transition from the home position to the fired position, wherein the cam member rotates through a second range of motion to transition from the fired position to the home position.

EXAMPLE 4

The method of Example 3, wherein the cam member rotates in a first angular direction during the first range of motion, wherein the cam member continues to rotate in the first angular direction during the second range of motion.

EXAMPLE 5

The method of Example 4, wherein the cam member rotates through a 360 degrees of angular motion during a single combination of the first and second ranges of motion.

EXAMPLE 6

The method of Example 3, wherein the cam member rotates in a first angular direction during the first range of motion, wherein the cam member rotates in a second angular direction during the second range of motion, wherein the second angular direction is opposite to the first angular direction.

EXAMPLE 7

The method of any one or more of Examples 1 through 6, wherein the circuit further comprises at least one polarity switch, wherein changing the polarity of the circuit comprises actuating the at least one polarity switch.

EXAMPLE 8

The method of Example 7, wherein the cam member is configured to actuate the at least one polarity switch.

EXAMPLE 9

The method of any one or more of Examples 1 through 8, wherein the apparatus further comprises a trigger, wherein the motor is configured to activate in response to actuation of the trigger, wherein the method further comprises actuating the trigger.

EXAMPLE 10

The method of any one or more of Examples 1 through 9, wherein a first battery pack is used to activate the motor to drive the cam member from the home position to the fired position, wherein a second battery pack is used to activate the motor to drive the cam member from the fired position to the home position, wherein the first battery pack has a first polarity, wherein the second battery pack has a second polarity that is opposite to the first polarity.

EXAMPLE 11

The method of Example 10, the method further comprising: (a) removing the first battery pack from a socket in the body; and (b) inserting the second battery pack in the socket in the body; wherein the act of activating the motor such that the cam member rotates from the fired position to the home position is performed while the second battery, pack is in the socket in the body.

EXAMPLE 12

The method of any one or more of Examples 1 through 11, further comprising cleaning the instrument.

EXAMPLE 13

The method of any one or more of Examples 1 through 12, further comprising reloading the stapling head assembly with staples.

EXAMPLE 14

The method of any one or more of Examples 1 through 13, further comprising packaging the instrument in a container.

EXAMPLE 15

The method of any one or more of Examples 1 through 14, further comprising using the reset instrument in a surgical procedure.

EXAMPLE 16

The method of Example 15, wherein using the reset instrument in a surgical procedure further comprises using the reset instrument in an anastomosis procedure.

EXAMPLE 17

A method for resetting an apparatus configured for stapling tissue, the apparatus comprising: (a) a stapling head assembly, wherein the stapling head assembly comprises: (i) an annularly arranged array of staples, and (ii) a knife with an annular cutting edge that is configured to cut tissue; (b) a shaft assembly coupled to the stapling head assembly; and (c) a body coupled to the shaft assembly, wherein the body comprises: a socket, (ii) a motor, and (iii) a cam member configured to rotate in response to activation of the motor, wherein the cam member is rotatable in a first direction from a home position to a fired position to actuate the stapling head assembly to thereby drive the staples and the knife through tissue, wherein the cam member is further rotatable in the first direction from the fired position to the home position; wherein the method comprises: (a) providing an apparatus including the cam member in the fired position, wherein a first battery having a first polarity was positioned in the socket and was used to activate the motor to thereby drive the cam member in the first direction from the home position to the fired position; (b) inserting a second battery in the socket, wherein the second battery has a second polarity opposite to the first polarity; and (c) activating the motor with the second battery to thereby drive the cam member in the first direction from the fired position to the home position.

EXAMPLE 18

The method of Example 17, wherein the apparatus further comprises at least one polarity switch, wherein the polarity switch is positioned to place the circuit in a first polarity state when the cam member is provided in the fired position, wherein the polarity switch is actuated to place the circuit in a second polarity state when the cam member completes a range of travel from the fired position to the home position in response to activating the motor with the second battery.

EXAMPLE 19

A surgical kit, the surgical kit comprising: (a) a stapling instrument the stapling instrument comprising: (i) a stapling head assembly, wherein the stapling head assembly comprises: (A) an annularly arranged array of staples, and (B) a knife with an annular cutting edge that is configured to cut tissue, (ii) a shaft assembly coupled to the stapling head assembly, (iii) a body coupled to the shaft assembly, wherein the body comprises: (A) a motor, and (B) a cam member configured to rotate in response to activation of the motor, wherein the cam member is rotatable in a first direction from a home position to a fired position to actuate the stapling head assembly to thereby drive the staples and the knife through tissue, wherein the cam member is further rotatable in the first direction from the fired position to the home position, and (iv) a circuit in electrical communication with the motor, wherein the circuit is configured to transition between a first polarity state and a second polarity state, wherein the motor is configured to drive the cam member from the home position to the fired position when the circuit is in the first polarity state, wherein the cam member is further configured to drive the cam member from the fired position to the home position when the circuit is in the second polarity state; (b) a first battery pack configured to activate the motor when the circuit is in the first polarity state, wherein the first battery pack has a first polarity associated with the first polarity state of the circuit; and (c) a second battery pack configured to activate the motor when the circuit is in the second polarity state, wherein the second battery pack has a second polarity associated with the second polarity state of the circuit.

EXAMPLE 20

The surgical instrument of Example 19, wherein the body further defines a socket, wherein the socket is configured to removably receive the first battery pack, wherein the socket is further configured to removably receive the second battery pack.

IV. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

At least some of the teachings herein may be readily combined with one or more teachings of U.S. Pat. No. 7,794,475, entitled "Surgical Staples Having Compressible or Crushable Members for Securing Tissue Therein and Stapling Instruments for Deploying the Same," issued Sep. 14, 2010, the disclosure of which is incorporated by reference herein; U.S. Pub. No. 2014/0151429, entitled "Trans-Oral Circular Anvil Introduction System with Dilation Feature," published Jun. 5, 2014, issued as U.S. Pat. 9,572,573 on Feb. 21, 2017, the disclosure of which is incorporated by reference herein; U.S. Pub. No. 2014/0144968, entitled "Surgical Staple with Integral Pledget for Tip Deflection," published May 29, 2014, issued as U.S. Pat. No. 9,289,207 on Mar. 22, 2016, the disclosure of which is incorporated by reference herein; U.S. Pub. No. 2014/0158747, entitled "Surgical Stapler with Varying Staple Widths along Different Circumferences," published Jun. 12, 2014, now abandoned, the disclosure of which is incorporated by reference herein; U.S. Pub. No. 2014/0144969, entitled "Pivoting Anvil for Surgical Circular Stapler," published May 29, 2014, issued as U.S. Pat. No. 9,498,222 on Nov. 22, 2016, the disclosure of which is incorporated by reference herein; U.S. Pub. No. 2014/0151430, entitled "Circular Anvil Introduction System with Alignment Feature," published Jun. 5, 2014, issued as U.S. Pat. No. 9,724,100 on Aug. 8, 2017, the disclosure of which is incorporated by reference herein; U.S. Pub. No. 2014/0166717, entitled "Circular Stapler with Selectable Motorized and Manual Control, Including a Control Ring," published Jun. 19, 2014, issued as U.S. Pat. No. 9,532,783 on Jan. 3, 2017, the disclosure of which is incorporated by reference herein; U.S. Pub. No. 2014/0166728, entitled "Motor Driven Rotary Input Circular Stapler with Modular End Effector," published Jun. 19, 2014, issued as U.S. Pat. No. 9,597,081 on Mar. 21, 2017, the disclosure of which is incorporated by reference herein; and/or U.S. Pub. No. 2014/0166718, entitled "Motor Driven Rotary Input Circular Stapler with Lockable Flexible Shaft," published Jun. 19, 2014, issued as U.S. Pat. No. 9,463,022 on Oct. 11, 2016, the disclosure of which is incorporated by reference herein. Various suitable ways in which such teachings may be combined will be apparent to those of ordinary skill in the art.

While the examples herein have been provided in the context of a circular stapling instrument, it should be understood that the various teachings herein may be readily applied to various other kinds of surgical instruments. By way of example only, the various teachings herein may be readily applied to linear stapling devices (e.g., endocutters). For instance, various teachings herein may be readily combined with various teachings of U.S. Pub. No. 2012/0239012, entitled "Motor-Driven Surgical Cutting Instrument with Electric Actuator Directional Control Assembly," published Sep. 20, 2012, issued as U.S. Pat. No. 8,453,914 on Jun. 4, 2013, the disclosure of which is incorporated by reference herein, and/or U.S. Pub. No. 2010/0264193, entitled "Surgical Stapling Instrument with An Articulatable End Effector," published Oct. 21, 2010, issued as U.S. Pat. No. 8,408,439 on Apr. 2, 2013, the disclosure of which is incorporated by reference herein, as will be apparent to those of ordinary skill in the art. As another merely illustrative example, the various teachings herein may be readily applied to a motorized electrosurgical device. For instance, various teachings herein may be readily combined with various teachings of U.S. Pub. No. 2012/0116379, entitled "Motor Driven Electrosurgical Device with Mechanical and Electrical Feedback," published May 10, 2012, issued as U.S. Pat. No. 9,161,803 on Oct. 20, 2015, the disclosure of which is incorporated by reference herein, as will be apparent to those of ordinary skill in the art. Other suitable kinds of instruments in which the teachings herein may be applied, and various ways in which the teachings herein may be applied to such instruments, will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method for resetting an apparatus configured for stapling tissue, the apparatus comprising:
    (a) a stapling assembly;
    (b) a body coupled with the stapling assembly, wherein the body comprises:
        (i) a motor, and
        (ii) a cam member configured to rotate in response to activation of the motor, wherein the cam member is rotatable in a first direction from a home position to a fired position to actuate the stapling assembly to thereby drive one or more staples through tissue; and
    (c) a circuit in electrical communication with the motor; wherein the method comprises:
    (a) providing the cam member in the fired position;
    (b) reversing the polarity of the circuit; and
    (c) after reversing the polarity of the circuit, actuating a user input feature to thereby activate the motor such that the cam member rotates from the fired position to the home position.

2. The method of claim 1, wherein the cam member rotates less than 360 degrees when rotating between the home position and fired position.

3. The method of claim 1, wherein the cam member rotates through a first range of motion to transition from the home position to the fired position, wherein the cam member rotates through a second range of motion to transition from the fired position to the home position.

4. The method of claim 3, wherein the cam member rotates in a first angular direction during the first range of motion, wherein the cam member continues to rotate in the first angular direction during the second range of motion.

5. The method of claim 4, wherein the cam member rotates through a full 360 degrees of angular motion during a single combination of the first and second ranges of motion.

6. The method of claim 3, wherein the cam member rotates in a first angular direction during the first range of motion, wherein the cam member rotates in a second angular direction during the second range of motion, wherein the second angular direction is opposite to the first angular direction.

7. The method of claim 1, wherein the circuit further comprises at least one polarity switch, wherein changing the polarity of the circuit comprises actuating the at least one polarity switch in response to rotation of the cam member.

8. The method of claim 1, wherein the apparatus further comprises a trigger, wherein the motor is configured to activate in response to actuation of the trigger, wherein the method further comprises actuating the trigger.

9. The method of claim 1, wherein a first battery pack is used to activate the motor to drive the cam member from the home position to the fired position, wherein a second battery pack is used to activate the motor to drive the cam member from the fired position to the home position, wherein the first battery pack has a first polarity, wherein the second battery pack has a second polarity that is opposite to the first polarity.

10. The method of claim 9, the method further comprising:
    (a) removing the first battery pack from a socket in the body; and
    (b) inserting the second battery pack in the socket in the body;
    wherein the act of activating the motor such that the cam member rotates from the fired position to the home position is performed while the second battery pack is in the socket in the body.

11. The method of claim 1, further comprising cleaning the instrument.

12. The method of claim 1, further comprising reloading the stapling assembly with staples.

13. The method of claim 1, further comprising packaging the apparatus in a container.

14. The method of claim 1, further comprising using the apparatus in a surgical procedure.

15. The method of claim 14, wherein using the apparatus in a surgical procedure further comprises using the apparatus in an anastomosis procedure.

16. The method of claim 1, wherein the cam member comprises a first cam feature and a second cam feature, wherein the body further comprises a cam follower, wherein the method further comprises:
    (a) driving the cam follower in a first direction with the first cam feature to thereby actuate the staples and a knife distally; and
    (b) driving the cam follower in a second direction with the second cam feature to thereby retract the knife proximally, wherein the second direction is opposite the first direction.

17. A method for setting an apparatus configured for stapling tissue, the apparatus comprising:
    (a) a stapling assembly, wherein the stapling assembly includes one or more staples;
    (b) a body coupled with the stapling assembly, wherein the body includes:
        (i) a motor, and
        (ii) a cam member configured to rotate in response to activation of the motor, wherein the cam member is rotatable in a first direction from a home position to a fired position to actuate the stapling assembly to thereby drive the one or more staples through tissue;
    wherein the method comprises:
    (a) providing the cam member in the fired position, wherein a first battery having a first polarity was used to activate the motor to thereby drive the cam member in the first direction from the home position to the fired position;
    (b) decoupling the motor from the first battery;
    (c) coupling the motor with a second battery, wherein the second battery has a second polarity opposite to the first polarity; and
    (d) activating the motor with the second battery to thereby drive the cam member in the first direction from the fired position to the home position.

18. The method of claim 17, wherein the apparatus further comprises a trigger, wherein the motor is configured to activate in response to actuation of the trigger, wherein the method further comprises actuating the trigger.

19. A method of operating an apparatus having a stapling assembly configured for stapling tissue, the method comprising:

(a) activating a motor of the apparatus to rotate a cam member of the apparatus in a first direction from a home position to a fired position to thereby actuate the stapling assembly;
(b) deactivating the motor when the cam member reaches the fired position;
(c) reversing a polarity of the apparatus; and
(d) after reversing the polarity of the apparatus and while the cam member is in the fired position, reactivating the motor to further rotate the cam member in the first direction from the fired position to the home position.

20. The method of claim 19, wherein the step of activating the motor comprises powering the motor with a first power source having a first polarity, wherein the step of reactivating the motor comprises powering the motor with a second power source having a second polarity opposite the first polarity.

\* \* \* \* \*